(12) United States Patent
Beaton et al.

(10) Patent No.: US 8,263,588 B2
(45) Date of Patent: Sep. 11, 2012

(54) GONADOTROPIN-RELEASING HORMONE RECEPTOR ANTAGONISTS AND METHODS RELATING THERETO

(75) Inventors: Graham Beaton, Poway, CA (US); Mi Chen, San Diego, CA (US); Timothy Richard Coon, Carlsbad, CA (US); Todd Ewing, San Diego, CA (US); Wanlong Jiang, San Diego, CA (US); Jinghua Yu, San Marcos, CA (US); Willy Moree, San Diego, CA (US); Warren Wade, San Diego, CA (US); Liren Zhao, San Diego, CA (US); Yun-fei Zhu, San Diego, CA (US); Martin Rowbottom, San Diego, CA (US); Neil Ashweek, San Diego, CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 253 days.

(21) Appl. No.: 12/594,815

(22) PCT Filed: Apr. 4, 2008

(86) PCT No.: PCT/US2008/059442
§ 371 (c)(1),
(2), (4) Date: Mar. 26, 2010

(87) PCT Pub. No.: WO2008/124614
PCT Pub. Date: Oct. 16, 2008

(65) Prior Publication Data
US 2010/0184741 A1 Jul. 22, 2010

Related U.S. Application Data

(60) Provisional application No. 60/910,619, filed on Apr. 6, 2007.

(51) Int. Cl.
*C07D 213/61* (2006.01)
*C07D 213/84* (2006.01)
*C07D 401/12* (2006.01)
*C07D 403/12* (2006.01)
*A61K 31/435* (2006.01)
*A61P 35/00* (2006.01)

(52) U.S. Cl. .......... 514/211.09; 514/213.01; 514/230.5; 514/269; 514/311; 514/314; 540/552; 540/593; 544/105; 544/315; 546/165

(58) Field of Classification Search .......... 540/552, 540/593; 544/105, 315; 546/165; 514/211.09, 514/213.01, 230.5, 269, 311, 314
See application file for complete search history.

(56) References Cited

U.S. PATENT DOCUMENTS

| 4,826,833 | A | 5/1989 | Chen | 514/192 |
|---|---|---|---|---|
| 5,082,849 | A | 1/1992 | Huang et al. | 514/314 |
| 5,612,356 | A | 3/1997 | Yoshimura et al. | 514/338 |
| 5,614,532 | A | 3/1997 | Carling et al. | 514/312 |
| 5,783,522 | A | 7/1998 | Schaefer et al. | 504/294 |
| 5,872,116 | A | 2/1999 | Dorn et al. | 514/227.5 |
| 6,074,989 | A | 6/2000 | Andree et al. | 504/243 |
| 6,258,822 | B1 | 7/2001 | Geyer et al. | 514/275 |
| 6,310,107 | B1 | 10/2001 | Kato et al. | 516/654 |
| 6,319,931 | B1 | 11/2001 | Kroemer et al. | 514/307 |
| 6,635,657 | B1 | 10/2003 | Beight et al. | 514/318 |
| 6,699,994 | B1 | 3/2004 | Babu et al. | 546/306 |
| 2003/0013719 | A1 | 1/2003 | Peukert et al. | 514/252.02 |
| 2004/0186148 | A1 | 9/2004 | Shankar et al. | 514/357 |
| 2004/0260080 | A1 | 12/2004 | Hovinen et al. | 536/25.32 |
| 2005/0182053 | A1 | 8/2005 | Chen et al. | 514/232.5 |
| 2005/0215548 | A1 | 9/2005 | Wang et al. | 514/235.2 |
| 2006/0270686 | A1 | 11/2006 | Kelly et al. | 514/255.05 |
| 2007/0117797 | A1 | 5/2007 | Goble et al. | 514/230.5 |
| 2007/0259919 | A1 | 11/2007 | Rheinheimer et al. | 514/334 |
| 2009/0069301 | A1 | 3/2009 | Milburn et al. | 514/218 |
| 2009/0325900 | A1 | 12/2009 | Ohno et al. | 514/63 |
| 2010/0152207 | A1 | 6/2010 | Beaton et al. | 514/260.1 |

FOREIGN PATENT DOCUMENTS

EP 0 708 756 B1 6/2005

(Continued)

OTHER PUBLICATIONS

International Preliminary Report on Patentability and Written Opinion dated Oct. 15, 2009; PCT/US2008/059442; International Filing Date: Apr. 4, 2008; 9 pages.

*Primary Examiner* — Bruck Kifle
(74) *Attorney, Agent, or Firm* — Seed IP Law Group PLLC

(57) ABSTRACT

GnRH receptor antagonists are disclosed which have utility in the treatment of a variety of sex-hormone related conditions in both men and women. The compounds of this invention have the structure: wherein $R_{1a}$, $R_{1b}$, $R_{1c}$, $R_{1d}$, $R_2$, $R_{2a}$, and A are as defined herein, including stereoisomers, esters, solvates, and pharmaceutically acceptable salts thereof. Also disclosed are compositions containing a compound of this invention in combination with a pharmaceutically acceptable carrier, as well as methods relating to the use thereof for antagonizing gonadotropin-releasing hormone in a subject in need thereof.

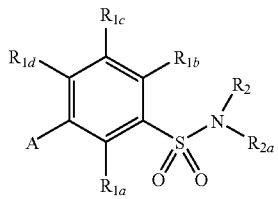

(I)

18 Claims, No Drawings

FOREIGN PATENT DOCUMENTS

| | | | |
|---|---|---|---|
| EP | 1657238 A1 | 5/2006 |
| JP | 3-173865 A | 7/1991 |
| WO | WO 92/00290 A1 | 1/1992 |
| WO | WO 95/02580 A2 | 1/1995 |
| WO | WO 96/07667 A1 | 3/1996 |
| WO | WO 96/14315 A1 | 3/1996 |
| WO | WO 98/50343 A2 | 11/1998 |
| WO | WO 99/02502 A2 | 1/1999 |
| WO | WO 99/55663 A1 | 11/1999 |
| WO | WO 00/39118 A1 | 7/2000 |
| WO | WO 00/69859 A1 | 11/2000 |
| WO | WO 01/29044 A1 | 4/2001 |
| WO | WO 01/55119 A2 | 8/2001 |
| WO | WO 02/20501 A2 | 3/2002 |
| WO | WO 02/32411 A2 | 4/2002 |
| WO | WO 02/34711 A1 | 5/2002 |
| WO | WO 03/011293 A2 | 2/2003 |
| WO | WO 03/011839 A1 | 2/2003 |
| WO | WO 03/011870 A1 | 2/2003 |
| WO | WO 03/013528 A1 | 2/2003 |
| WO | WO 2004/002948 A1 | 1/2004 |
| WO | WO 2004/006858 A2 | 1/2004 |
| WO | WO 2004/041789 A1 | 5/2004 |
| WO | WO 2004/052371 A2 | 6/2004 |
| WO | WO 2004/091480 A2 | 10/2004 |
| WO | WO 2004/096795 A2 | 11/2004 |
| WO | WO 2005/007164 A1 | 1/2005 |
| WO | WO 2005/007165 A1 | 1/2005 |
| WO | WO 2005/007633 A1 | 1/2005 |
| WO | WO 2005/012241 A2 | 2/2005 |
| WO | WO 2005/020921 A2 | 3/2005 |
| WO | WO 2005/044007 A1 | 5/2005 |
| WO | WO 2005/073232 A1 | 8/2005 |
| WO | WO 2006/000358 A1 | 1/2006 |
| WO | WO 2006/017214 A2 | 2/2006 |
| WO | WO 2006/022955 A2 | 3/2006 |
| WO | WO 2006/028958 A2 | 3/2006 |
| WO | WO 2006/040568 A1 | 4/2006 |
| WO | WO 2006/044975 A2 | 4/2006 |
| WO | WO 2006/078287 A2 | 7/2006 |
| WO | 2006083005 A | 8/2006 |
| WO | WO 2006/133559 A1 | 12/2006 |
| WO | 2007046392 | 4/2007 |

GONADOTROPIN-RELEASING HORMONE RECEPTOR ANTAGONISTS AND METHODS RELATING THERETO

BACKGROUND

1. Technical Field

This invention relates generally to gonadotropin-releasing hormone (GnRH) receptor antagonists, and to methods of treating disorders by administration of such antagonists to a warm-blooded animal in need thereof.

2. Description of the Related Art

Gonadotropin-releasing hormone (GnRH), also known as luteinizing hormone-releasing hormone (LHRH), is a decapeptide (pGlu-His-Trp-Ser-Tyr-Gly-Leu-Arg-Pro-Gly-NH$_2$) that plays an important role in human reproduction. GnRH is released from the hypothalamus and acts on the pituitary gland to stimulate the biosynthesis and release of luteinizing hormone (LH) and follicle-stimulating hormone (FSH). LH released from the pituitary gland is responsible for the regulation of gonadal steroid production in both males and females, while FSH regulates spermatogenesis in males and follicular development in females.

Due to its biological importance, synthetic antagonists and agonists to GnRH have been the focus of considerable attention, particularly in the context of prostate cancer, breast cancer, endometriosis, uterine leiomyoma (fibroids), ovarian cancer, prostatic hyperplasia, assisted reproductive therapy, and precocious puberty (*The Lancet* 358:1793-1803, 2001; *Mol. Cell. Endo.* 166:9-14, 2000). For example, peptidic GnRH agonists, such as leuprorelin (pGlu-His-Trp-Ser-Tyr-d-Leu-Leu-Arg-Pro-NHEt), have been used to treat such conditions. Such agonists appear to function by binding to the GnRH receptor in the pituitary gonadotropins, thereby inducing the synthesis and release of gonadotropins. Chronic administration of GnRH agonists depletes gonadotropins and subsequently down-regulates the receptor, resulting in suppression of steroidal hormones after some period of time (e.g., on the order of 2-3 weeks following initiation of chronic administration).

In contrast, GnRH antagonists are believed to suppress gonadotropins from the onset, and thus have received the most attention over the past two decades. To date, some of the primary obstacles to the clinical use of such antagonists have been their relatively low bioavailability and adverse side effects caused by histamine release. However, several peptidic antagonists with low histamine release properties have been reported, although they still must be delivered via sustained delivery routes (such as subcutaneous injection or intranasal spray) due to limited bioavailability.

In view of the limitations associated with peptidic GnRH antagonists, a number of nonpeptidic compounds have been proposed. Recently published PCT applications which disclose compounds and their use as GnRH antagonists include WO 00/69859, WO 01/29044, WO 01/55119, WO 03/013528, WO 03/011870, WO 03/011841, WO 03/011839, WO 03/011293, WO 05/007164, WO 05/007165 and WO 05/007633.

While significant strides have been made in this field, there remains a need in the art for effective small molecule GnRH receptor antagonists. There is also a need for pharmaceutical compositions containing such GnRH receptor antagonists, as well as methods relating to the use thereof to treat, for example, sex-hormone related conditions. The present invention fulfills these needs, and provides other related advantages.

BRIEF SUMMARY

In brief, this invention is generally directed to gonadotropin-releasing hormone (GnRH) receptor antagonists, as well as to methods for their preparation and use, and to pharmaceutical compositions containing the same. More specifically, the GnRH receptor antagonists of this invention are compounds having the following general structure (I):

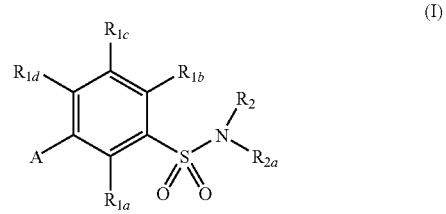

including stereoisomers, prodrugs and pharmaceutically acceptable salts thereof, wherein $R_{1a}$, $R_{1b}$, $R_{1c}$, $R_{1d}$, $R_2$, $R_{2a}$, and A are as defined below.

The GnRH receptor antagonists of this invention may have utility over a wide range of therapeutic applications, and may be used to treat a variety of sex-hormone related conditions in both men and women, as well as a mammal in general (also referred to herein as a "subject"). For example, such therapeutic applications include endometriosis, uterine fibroids, polycystic ovarian disease, dysmenorrhea, dyspareunia, menorrhagia, nonmenstrual pelvic pain, pelvic tenderness, induration, general disorders of the menstrual cycle, premature ovarian failure due to chemotherapy or early menopause, hirsutism, precocious puberty, gonadal steroid-dependent neoplasia such as cancers of the prostate, breast and ovary, gonadotrophe pituitary adenomas, adenomyosis, sleep apnea, irritable bowel syndrome, premenstrual syndrome, benign prostatic hypertrophy, lower urinary tract symptoms (LUTS), contraception and infertility (e.g., assisted reproductive therapy such as in vitro fertilization). The compounds of this invention may also be useful as an adjunct to treatment of growth hormone deficiency and short stature, and for the treatment of systemic lupus erythematosis. The compounds also may be useful in combination with androgens, estrogens, progesterones, antiestrogens, antiprogestogens, angiotensin-converting enzyme inhibitors, angiotensin II-receptor antagonists, renin inhibitors, bisphosphonates and other agents for the treatment and/or prevention of disturbances of calcium, phosphate and bone metabolism, aromatase inhibitors, analgesics such as non-steroidal anti-inflamatory drugs (NSAIDS), other COX inhibitors, and anti-NGF agents.

The methods of this invention include administering an effective amount of a GnRH receptor antagonist, preferably in the form of a pharmaceutical composition, to a mammal in need thereof. Thus, in still a further embodiment, pharmaceutical compositions are disclosed containing one or more GnRH receptor antagonists of this invention in combination with a pharmaceutically acceptable carrier and/or diluent.

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION

As mentioned above, the present invention is directed generally to compounds useful as gonadotropin-releasing hormone (GnRH) receptor antagonists. The compounds of this invention have the following structure (I):

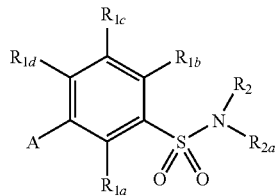

and stereoisomers, esters, solvates, and pharmaceutically acceptable salts thereof,
wherein:
A is pyridyl, phenyl, quinolinyl, naphthyridinyl, thienopyrimidinyl, or 2-oxo-pyrimidinyl wherein the pyridyl, phenyl, quinolinyl, thienopyrimidinyl or 2-oxo-pyrimidinyl are substituted with 0-5 $R_4$;

$R_{1a}$ is H, halogen, $C_{1-4}$alkyl, $C_{1-4}$alkoxy or trifluoromethyl;

$R_{1b}$ and $R_{1c}$ are the same or different and are independently H, halogen, hydroxy, halo$C_{1-4}$alkyl, —$C_{1-6}$alkyl-$(R_5)_p$, —O—$C_{1-6}$alkyl-$(R_5)_p$, —$C_{1-6}$alkyl-O—$C_{1-6}$alkyl-$(R_5)_p$, —$NR_7$—$C_{1-6}$alkyl-$(R_5)_p$, or —$S(O)_m$—$C_{1-6}$alkyl-$(R_5)_p$;

$R_{1d}$ is F, Cl, methyl, $CF_3$ or cyano;

$R_2$ is $C_{1-4}$alkyl-$(R_5)_p$;

$R_{2a}$ is phenyl substituted with 0-4 $R_3$, heteroaryl substituted with 0-4 $R_3$, $C_{1-4}$alkyl substituted with 0-4 $R_3$, aryl-$C_{1-4}$alkyl substituted with 0-4 $R_3$, or heteroaryl-$C_{1-4}$alkyl substituted with 0-4 $R_3$;

or $R_2$ and $R_{2a}$ taken together with the nitrogen to which they are attached form a heterocycle which is substituted with 0-4 $R_3$;

$R_3$ at each occurrence is independently halogen, cyano, halo-$C_{1-4}$alkyl, $R_5$, —$C_{1-6}$alkyl-$(R_5)_p$, —$C_{1-6}$alkyl-O—$C_{1-6}$alkyl-$(R_5)_p$, —O—$C_{1-6}$alkyl-$(R_5)_p$, —$NR_7$—$C_{1-6}$alkyl-$(R_5)_p$, —$S(O)_m$—$C_{1-6}$alkyl-$(R_5)_p$, —O—$C_{1-6}$alkyl-$NR_7$—$C_{1-6}$alkyl-$(R_5)_p$, heterocycle-$(R_5)_p$;

$R_4$ at each occurrence is independently halogen, $C_{1-6}$alkyl, halo$C_{1-4}$alkyl, $C_{1-6}$alkoxy, hydroxy, cyano, thio$C_{1-6}$alkyl, —$C(O)NR_7R_8$ or 5 member heteroaryl;

$R_5$ at each occurrence is independently H, hydroxy, —OC(O)—$C_{1-6}$alkyl, —OC(O)O—$C_{1-6}$alkyl, —OC(O)—$C_{1-6}$alkyl-$NR_7R_8$, —$COOR_6$, —$C(O)NR_7R_8$, —$NR_7C(O)NR_7R_8$, —$S(O)_2NR_9R_9$, —$S(O)_m$—$C_{1-4}$alkyl, —$NR_7R_8$, $C_{1-6}$alkoxy,
—O-heterocycle, or heterocycle wherein said heterocycle and said —O-heterocycle are substituted with 0-4 groups selected from halogen, $C_{1-6}$alkyl, $C_{1-4}$haloalkyl, hydroxy, oxo, thio, —$NH_2$, —$S(O)_2C_{1-4}$alkyl and —COOH;

$R_6$ at each occurrence is independently H, $C_{1-4}$alkyl, $C_{1-4}$alkyl-O—C(O)—$C_{1-6}$alkyl, or $C_{1-4}$alkyl-O—C(O)—O—$C_{1-6}$alkyl;

$R_7$ at each occurrence is independently H, $C_{1-4}$alkyl, hydroxy, or heterocycle where said heterocycle is substituted with 0-4 groups selected from halogen, $C_{1-6}$alkyl, hydroxy, keto, —$NH_2$ and —COOH;

$R_8$ at each occurrence is independently H, $C_{1-4}$alkyl, halo$C_{1-4}$alkyl, —C(O)—$C_{1-4}$alkyl, —C(O)-halo$C_{1-4}$alkyl, —$C(O)NR_7C_{1-4}$alkyl, —$S(O)_m$-halo$C_{1-4}$alkyl or —$S(O)_m$—$C_{1-4}$alkyl;

$R_9$ at each occurrence is independently H, $C_{1-4}$alkyl, or —$C(O)C_{1-4}$alkyl;
m is 0-2; and
p at each occurrence is independently 1-3.

As used herein, the above terms have the following meaning:

"Alkyl" means a straight chain or branched, noncyclic or cyclic, unsaturated or saturated aliphatic hydrocarbon containing from 1 to 10 carbon atoms. The term "$C_{1-4}$alkyl" has the same meaning as alkyl but contains from 1 to 4 carbon atoms while the term "$C_{1-6}$alkyl" has the same meaning as alkyl but contains from 1 to 6 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, —$CH_2$-cyclopropyl, —$CH_2$-cyclobutyl, —$CH_2$-cyclopentyl, —$CH_2$-cyclohexyl, and the like; while unsaturated cyclic alkyls include cyclopentenyl and cyclohexenyl, and the like. Cyclic alkyls, also referred to as "homocyclic rings," and include di- and poly-homocyclic rings such as decalin and adamantyl. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like.

"Aryl" means an aromatic carbocyclic moiety such as phenyl or naphthyl.

"Arylalkyl" means an alkyl having at least one alkyl hydrogen atom replaced with a heteroaryl moiety, such as —$CH_2$pyridinyl, —$CH_2$pyrimidinyl, and the like.

"Heteroaryl" means an aromatic heterocycle ring of 5- to 10-members and having at least one heteroatom selected from nitrogen, oxygen and sulfur, and containing at least 1 carbon atom, including both mono- and bicyclic ring systems. Representative heteroaryls include (but are not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, oxadiazolyl, thiadiazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —$CH_2$pyridinyl, —$CH_2$pyrimidinyl, and the like.

"Heterocycle" (also referred to herein as a "heterocycle ring") means a 5- to 7-membered monocyclic, or 7- to 14-membered polycyclic, heterocycle ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring as well as tricyclic (and higher) heterocyclic rings. The heterocycle may be attached via any heteroatom or carbon atom. Heterocycles include heteroaryls as defined above. Thus, in addition to the aromatic heteroaryls listed above, heterocycles also include (but are not limited to) morpholinyl, pyrrolidinonyl, pyrrolidinyl, piperizinyl, piperidinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, tetrahydrothiopyranyl, tetrahydropyrimidinyl, tetrahydrothiophenyl, tetrahydrothiopyranyl, and the like.

"Haloalkyl" means an alkyl group having at least one hydrogen atom replaced with a halogen, such as trifluoromethyl and the like.

"Halogen" means fluoro, chloro, bromo or iodo, typically fluoro or chloro.

"Hydroxy" means —OH.

"Oxo" means an oxygen double bonded to a carbon (means C=O).

"Thio" means a sulfur double bonded to a carbon (means C=S).

"Alkoxy" means an alkyl moiety attached through an oxygen bridge (i.e., —O-alkyl) and includes groups such as methoxy and ethoxy.

"Alkylthio" means an alkyl moiety attached through a sulfur bridge (i.e., —S-alkyl) and includes groups such as methylthio and ethylthio.

In an embodiment, compounds of the present invention have the following structure:

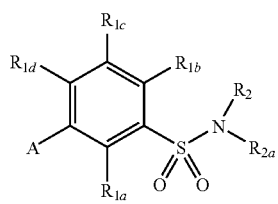

(I)

or a stereoisomer, ester, solvate or pharmaceutically acceptable salt thereof,
wherein:

A is pyridyl, phenyl, quinolinyl, thienopyrimidinyl, or 2-oxo-pyrimidinyl wherein the pyridyl, phenyl, quinolinyl, thienopyrimidinyl or 2-oxo-pyrimidinyl are substituted with 0-4 $R_4$;

$R_{1a}$ is H, halogen, $C_{1-4}$alkyl, $C_{1-4}$alkoxy or trifluoromethyl;

$R_{1b}$ and $R_{1c}$ are the same or different and are independently H, halogen, hydroxy, halo$C_{1-4}$alkyl, —$C_{1-6}$alkyl-$(R_5)_p$, —$C_{1-6}$O—$C_{1-6}$alkyl-$(R_5)_p$, —$C_{1-6}$alkyl-O—$C_{1-6}$alkyl-$(R_5)_p$, —$NR_7$—$C_{1-6}$alkyl-$(R_5)_p$, or —$S(O)_m$—$C_{1-6}$alkyl-$(R_5)_p$;

$R_{1d}$ is Cl, methyl, $CF_3$ or cyano;

$R_2$ is $C_{1-4}$alkyl-$(R_5)_p$;

$R_{2a}$ is phenyl substituted with 0-4 $R_3$;

or $R_2$ and $R_{2a}$ taken together with the nitrogen to which they are attached form a heterocycle which is substituted with 0-4 $R_3$;

$R_3$ at each occurrence is independently halogen, haloalkyl, hydroxy, —$C_{1-6}$alkyl-$(R_5)_p$, —$C_{1-6}$alkyl-O—$C_{1-6}$alkyl-$(R_5)_p$, —O—$C_{1-6}$alkyl-$(R_5)_p$, —$NR_7$—$C_{1-6}$alkyl-$(R_5)_p$, —$S(O)_m$—$C_{1-6}$alkyl-$(R_5)_p$, —$CO_2R_6$, —$C(O)NR_7R_8$;

$R_4$ at each occurrence is independently halogen, alkyl, haloalkyl, alkoxy, hydroxy, cyano, thioalkyl, —$C(O)NR_7R_8$ or 5 member heteroaryl;

$R_5$ at each occurrence is independently H, hydroxy, —OC(O)—$C_{1-6}$alkyl, —OC(O)O—$C_{1-6}$alkyl, —OC(O)—$C_{1-6}$alkyl-$NR_7R_5$, —C(O)O$R_6$, —C(O)N$R_7R_8$, —S(O)$_2NR_9R_9$, —S(O)$_m$$C_{1-6}$alkyl, —$NR_7R_8$, $C_{1-6}$alkoxy, or a heterocycle selected from the group consisting of

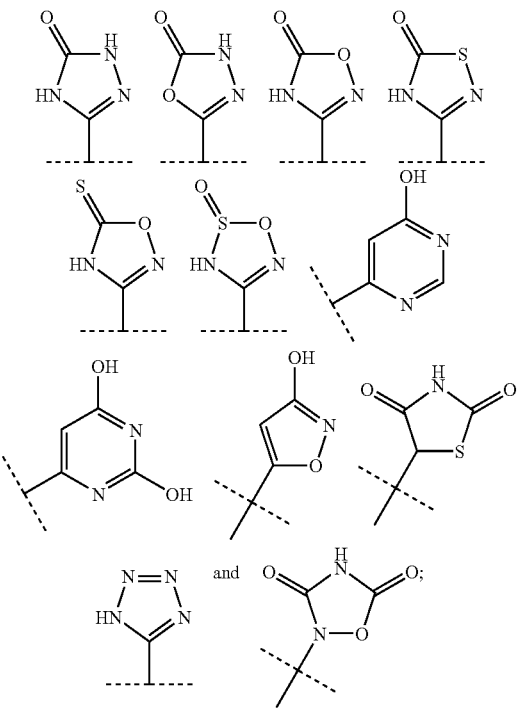

$R_6$ at each occurrence is independently H, $C_{1-4}$alkyl, $C_{1-4}$alkyl-O—C(O)—$C_{1-6}$alkyl, or $C_{1-4}$alkyl-O—C(O)—O—$C_{1-6}$alkyl;

$R_7$ is H, $C_{1-4}$alkyl or hydroxy;

$R_8$ is H, $C_{1-4}$alkyl, —C(O)—$C_{1-4}$alkyl, —C(O)N$R_7$—$C_{1-4}$alkyl, or —$S(O)_m$—$C_{1-4}$alkyl;

$R_9$ at each occurrence is independently H, $C_{1-4}$alkyl, or —(O)$C_{1-4}$alkyl;

m is 0-2; and p at each occurrence is independently 1-3.

In embodiments of the present invention, A of structure (I) may be 2-pyridyl substituted with an $R_4$ group as shown in structure (II) and 3-pyridyl substituted in the 4 and 6 positions with $R_4$ as shown in structure (III).

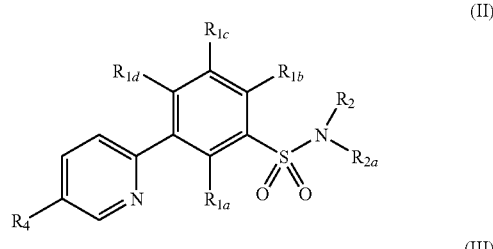

(II)

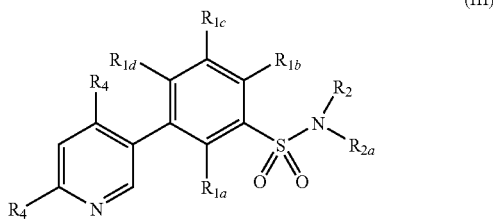

(III)

In an embodiment, $R_2$ of structure (I) is methyl and $R_{2a}$ is phenyl substituted with one $R_3$ group as shown in structure (IV). In other embodiments, $R_2$ and $R_{2a}$ of structure (I) taken together with the nitrogen to which they are attached cyclize to form a heterocycle ring where the heterocycle ring is 1,2,3,4-tetrahydro-quinolin-1-yl (here shown as substituted with two $R_3$ groups at the 4 position) as shown in structure (V) and 1,3,4,5-tetrahydro-benzo[b][1,4]diazepin-2-on-5-yl (here shown as substituted with a $R_3$ group) as shown in structure (VI).

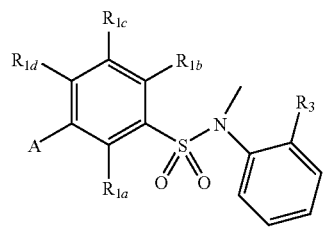

(IV)

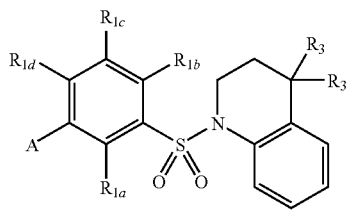

(V)

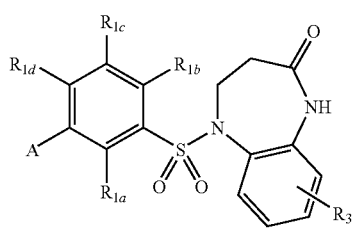

(VI)

In other embodiments, $R_2$ and $R_{2a}$ of structure (I) taken together with the nitrogen to which they are attached cyclize to form a heterocycle ring where the heterocycle ring is 2,3,4,5-tetrahydro-1H-benzo[b]azepin-1-yl (here shown as substituted with two $R_3$ groups at the 4 position and another $R_3$ elsewhere) as shown in structure (VII) and the same ring instead substituted with 3 $R_3$ groups, 2 of which are at the 5 position as shown in structure (VIII).

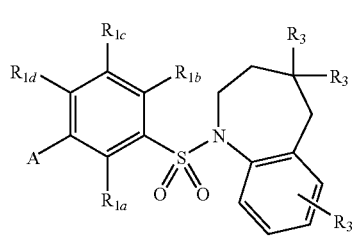

(VII)

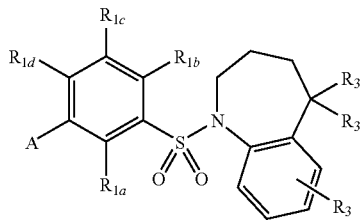

(VIII)

In an embodiment, A of structure (I) is quinolin-2-yl substituted with cyano at the 3 position and with 2 $R_4$ substituents as shown in structure (IX). Structure (X) shows an embodiment of structure (I) where A is a pyrimidin-2-one with 2 $R_4$ substitutions. Structure (XI) shows an embodiment of structure (I) where $R_{2a}$ is phenyl substituted with two $R_3$ groups, wherein one of the $R_3$ groups is —O—$C_{1-6}$alkyl-$R_5$, where $R_5$ is COOR$_6$ and $R_6$ is hydrogen.

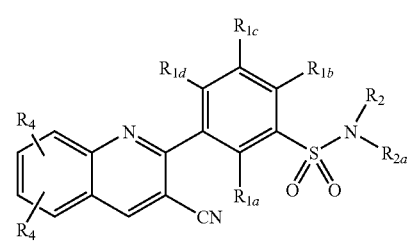

(IX)

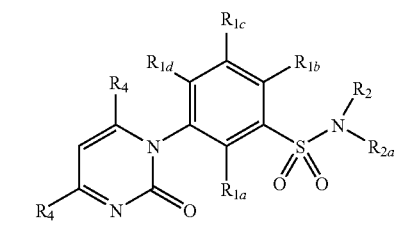

(X)

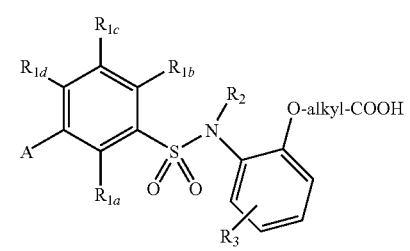

(XI)

In other embodiments of structure (I), $R_{1b}$ is —O—$C_{1-6}$ alkyl-$R_5$, where $R_5$ is H, OH, and COOH as shown in structures (XII), (XIII), and (XIV), respectively.

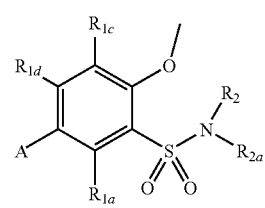

(XII)

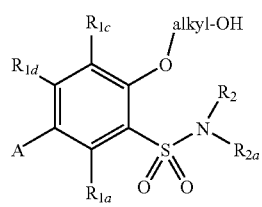
(XIII)

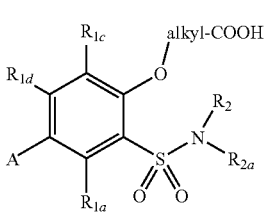
(XIV)

In an embodiment of structure I, $R_{1d}$ is a chloro group as illustrated in structure (XV). In another embodiment of structure (I), $R_{1a}$ and $R_{1c}$ can be hydrogen, while $R_{1d}$ is chloro group and $R_{1b}$ is —O—$C_{1-6}$alkyl-$R_5$ as shown in structure (XVI).

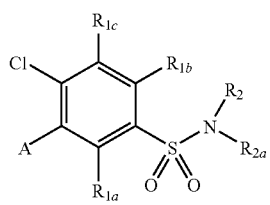
(XV)

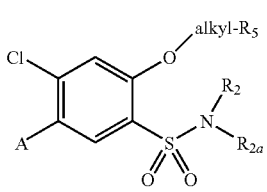
(XVI)

In other embodiments, A of structure (I) is 2-trifluoromethyl-isonicotinonitrile as shown in structure (XVII). In a further embodiment of structure (XVII), $R_{1d}$ may be a chloro group as illustrated in Structure (XVIII). In an embodiment, $R_{1b}$ of structure (XVIII) is —O—$C_{1-6}$alkyl-$R_5$, specifically alkyl is one carbon and $R_5$ is H giving a methoxy as shown in structure (XIX).

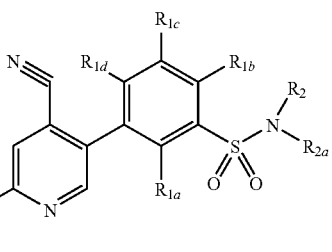
(XVII)

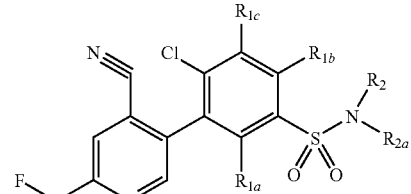
(XVIII)

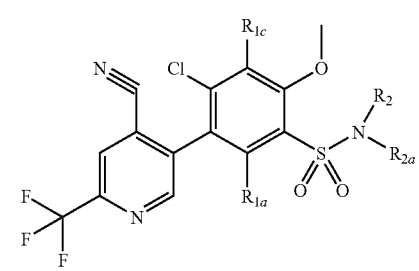
(XIX)

In an embodiment of structure (I), A is 2-cyano-4-trifluoromethyl-phenyl group as shown in Structure (XX). In another embodiment, $R_2$ and $R_{2a}$ of structure (I) taken together with the nitrogen to which they are attached cyclize to form a heterocycle ring where the heterocycle ring is 1,2,3,4-tetrahydro-[1,8]naphthyridin1-yl substituted with 2 $R_3$ groups as shown in structure (XXI) and 2,3,4,5-tetrahydro-1H-benzo[b]azepin-1-yl substituted with an -alkyl-$R_5$ group as shown in structure (XXII).

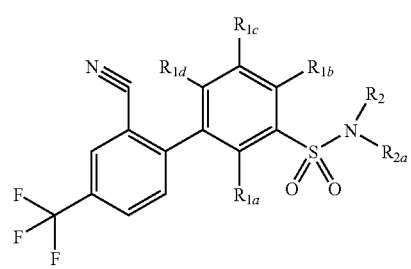
(XX)

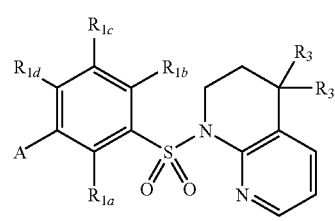
(XXI)

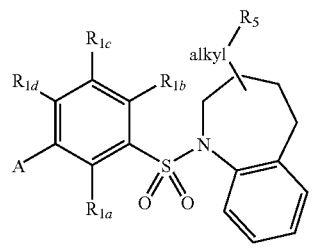
(XXII)

In an embodiment of structure (I), $R_{2a}$ is a benzyl group and $R_2$ is a methyl group.

In an embodiment of structure (I), $R_{2a}$ is a substituted benzyl group where the benzyl group is substituted with 1-3 $R_3$ and $R_2$ is a methyl group.

In an embodiment of structure (I), $R_{1b}$ is O—$C_{1-6}$alkyl $(R_5)_p$ group, where alkyl is —$CH_2CH_2$—, $R_5$ is $CO_2H$ and p is 1.

In an embodiment of structure (I), $R_{1b}$ is O—$C_{1-6}$alkyl $(R_5)_p$ group, where alkyl is —$CH_2CH_2CH_2$—, $R_5$ is $CO_2H$ and p is 1.

In an embodiment of structure (I), $R_{1b}$ is O—$C_{1-6}$alkyl $(R_5)_p$ group, where alkyl is —$CH_2CH_2CH_2$—, $R_5$ is $CO_2H$ and p is 1.

In an embodiment of structure (I), $R_{1b}$ is O—$C_{1-6}$alkyl $(R_5)_p$ group, where alkyl is —$CH_2CH_2CH_2$—, $R_5$ is tetrazole group and p is 1.

In an embodiment, A of structure (I) is 2-pyridyl substituted with 0-4 $R_4$.

In an embodiment, A of structure (I) is 2-pyridyl substituted with 2 $R_4$ groups at the 3 and 5 position.

In an embodiment, A of structure (I) is 3-pyridyl substituted with 0-4 $R_4$.

In an embodiment, A of structure (I) is 3-pyridyl substituted with 2 $R_4$ groups at the 4 and 6 position.

In a further embodiment, A of structure (I) is 4-cyano-6-trifluoromethylpyridin-3-yl.

In an embodiment, A of structure (I) is 3-cyano-5-fluoro-quinoline-2-yl.

In an embodiment, A of structure (I) is 3-cyano-5-trifluoromethyl-quinoline-2-yl.

In an embodiment, A of structure (I) is 3-cyano-[1,5]naphthyridin-2-yl.

In an embodiment, A of structure (I) is phenyl substituted with 0-4 $R_4$.

In an embodiment, $R_4$ is selected from halogen, haloalkyl, alkyl and cyano.

In an embodiment, A is substituted with 2 $R_4$ groups wherein each $R_4$ is independently selected from halogen cyano and trifluoromethyl.

$R_{1a}$ and $R_{1c}$, in an embodiment, are both H.

In an embodiment, $R_{1d}$ is Cl, F, $CF_3$ or methyl.

In an embodiment, $R_{1d}$ is Cl.

In an embodiment, $R_{1b}$ is H, hydroxy, —$C_{1-6}$alkyl-$(R_5)_p$, or —O—$C_{1-6}$alkyl-$(R_5)_p$.

In an embodiment, $R_{1b}$ is H, hydroxy, or —O—$C_{1-6}$alkyl-$(R_5)_p$ where $R_5$ at each occurrence is H.

In an embodiment, $R_{1b}$ is —O—$C_{1-6}$alkyl-$(R_5)_p$.

In an embodiment, $R_{1b}$ is —O—$C_{1-6}$alkyl-$(R_5)_p$ where —$C_{1-6}$alkyl- is —$C_{2-4}$alkyl-.

In an embodiment, $R_{1b}$ is —O—$C_{1-6}$alkyl-$(R_5)_p$ where —$C_{1-6}$alkyl- is —$CH_2CH_2CH_2$—.

In an embodiment, $R_{1b}$ is —O—$C_{1-6}$alkyl-$(R_5)_p$ where $R_5$ is hydroxy or COOH.

In an embodiment, $R_{1b}$ is —O—$C_{1-6}$alkyl-$(R_5)_p$ where $R_5$ is H and p is 1.

In an embodiment, $R_2$ is —$C_{1-6}$alkyl-$(R_5)_p$ where $R_5$ at each occurrence is H.

In an embodiment, $R_{2a}$ is phenyl substituted with 0-4 $R_3$ or heteroaryl substituted with 0-4 $R_3$.

In an embodiment, $R_{2a}$ is phenyl substituted with 0-4 $R_3$ where $R_3$ is selected from halogen, cyano, halo-$C_{1-4}$alkyl, $R_5$, —$C_{1-6}$alkyl-$(R_5)_p$, —$C_{1-6}$alkyl-O—$C_{1-6}$alkyl-$(R_5)_p$, —O—$C_{1-6}$alkyl-$(R_5)_p$, —$NR_7$—$C_{1-6}$alkyl-$(R_5)_p$, —$S(O)_m$—$C_{1-6}$alkyl-$(R_5)_p$, —O—$C_{1-6}$alkyl-$NR_7$—$C_{1-6}$alkyl-$(R_5)_p$, heterocycle-$(R_5)_p$.

In an embodiment, $R_{2a}$ is a heteroaryl substituted with 0-4 $R_3$, where $R_3$ is selected from halogen, cyano, halo-$C_{1-4}$alkyl, $R_5$, —$C_{1-6}$alkyl-$(R_5)_p$, —$C_{1-6}$alkyl-O—$C_{1-6}$alkyl-$(R_5)_p$, —O—$C_{1-6}$alkyl-$(R_5)_p$, —$NR_7$—$C_{1-6}$alkyl-$(R_5)_p$, —$S(O)_m$—$C_{1-6}$alkyl-$(R_5)_p$, —O—$C_{1-6}$alkyl-$NR_7$—$C_{1-6}$alkyl-$(R_5)_p$, heterocycle-$(R_5)_p$.

In an embodiment, $R_{2a}$ is pyridyl substituted with 0-4 $R_3$ where $R_3$ is selected from halogen, cyano, halo-$C_{1-4}$alkyl, $R_5$, —$C_{1-6}$alkyl-$(R_5)_p$, —$C_{1-6}$alkyl-O—$C_{1-6}$alkyl-$(R_5)_p$, —O—$C_{1-6}$alkyl-$(R_5)_p$, —$NR_7$—$C_{1-6}$alkyl-$(R_5)_p$, —$S(O)_m$—$C_{1-6}$alkyl-$(R_5)_p$, —O—$C_{1-6}$alkyl-$NR_7$—$C_{1-6}$alkyl-$(R_5)_p$, heterocycle-$(R_5)_p$.

In an embodiment, $R_2$ and $R_{2a}$ taken together with the nitrogen to which they are attached form a heterocycle which is substituted with 0-4 $R_3$.

In an embodiment, $R_3$ is halogen, cyano, halo-$C_{1-4}$alkyl, —O—$C_{1-6}$alkyl-$(R_5)_p$, or heterocycle-$(R_5)_p$.

In an embodiment, $R_3$ is halogen, cyano, —O—$C_{1-4}$alkyl-$(R_5)_p$, or heterocycle-$(R_5)_p$.

In an embodiment, $R_3$, at one occurrence, is —O—$C_{1-6}$alkyl-$(R_5)_p$, where $R_5$ is H, hydroxy, —COOH or heterocycle where said heterocycle is substituted with 0-4 groups selected from halogen, $C_{1-4}$alkyl, $C_{1-4}$haloalkyl, hydroxy, oxo, thio, —$NH_2$, —$S(O)_2C_{1-4}$alkyl and —COOH.

In an embodiment, $R_3$, at one occurrence, is —O—$C_{1-6}$alkyl-$(R_5)_p$, where $R_5$ is OH or —COOH.

In an embodiment, $R_3$, at one occurrence is —O—$C_{1-6}$alkyl-$(R_5)_p$ where —$C_{1-6}$alkyl- is —$C_{2-3}$alkyl-.

In an embodiment, $R_3$, at one occurrence is —O—$C_{1-6}$alkyl-$(R_5)_p$ where —$C_{1-6}$alkyl- is —$CH_2CH_2$—.

In an embodiment, one of $R_{1b}$ and $R_3$ is —O—$C_{1-6}$alkyl-$(R_5)_p$, where $R_5$ is OH, —$COOR_6$ or heterocycle wherein said heterocycle is substituted with 0-4 groups selected from halogen, $C_{1-4}$alkyl, $C_{1-4}$haloalkyl, hydroxy, oxo, thio, —$NH_2$, —$S(O)_2C_{1-4}$alkyl and —COOH.

In an embodiment, one of $R_{1b}$ and $R_3$ is —O—$C_{1-6}$alkyl-$(R_5)_p$, where $R_5$ is OH or —COOH.

In an embodiment, $R_{1b}$ is —O—$C_{1-6}$alkyl-$(R_5)_p$, where $R_5$ is OH or —COOH; and $R_{2a}$ is phenyl substituted with 1-4 $R_3$, where $R_3$ is selected from halogen, cyano, $CF_3$, methoxy, methyl, or $CO_2R_6$.

In an embodiment, $R_{1b}$ is hydrogen and $R_{2a}$ is phenyl substituted with 1-2 $R_3$, where one $R_3$ is selected from O—$C_{1-6}$alkyl-$(R_5)_p$ and another $R_3$ is selected from hydrogen, halogen, cyano, $CF_3$, methoxy, or methyl.

In an embodiment, $R_{1b}$ is —O—$CH_3$ and $R_{2a}$ is phenyl substituted with 1-2 $R_3$, where one $R_3$ is selected from O—$C_{1-6}$alkyl-$(R_5)_p$ and another $R_3$ is selected from hydrogen, halogen, cyano, $CF_3$, methoxy, or methyl.

In an embodiment, $R_5$ is heterocycle and may be:

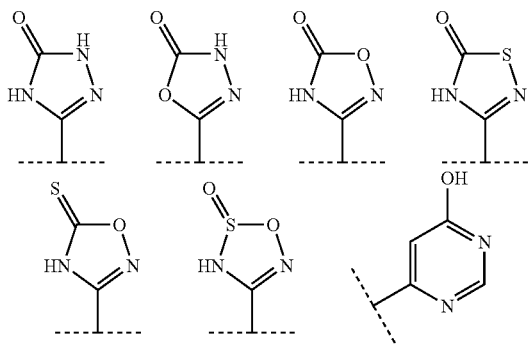

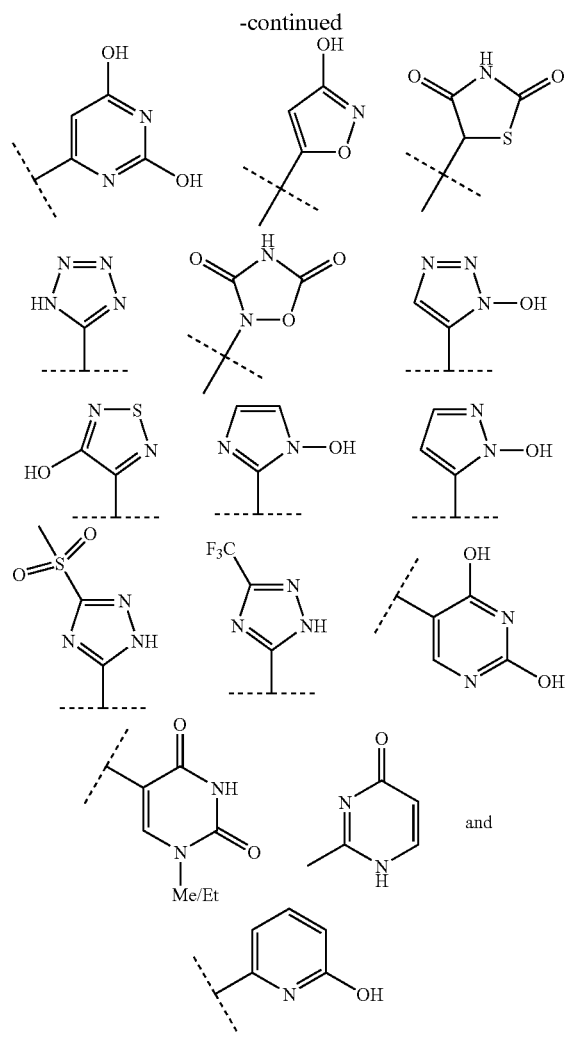

Representative compounds of the present invention include:
4-[5-Chloro-4-(4-cyano-6-trifluoromethyl-pyridin-3-yl)-2-(5,5-difluoro-2,3,4,5-tetrahydro-benzo[b]azepine-1-sulfonyl)-phenoxy]-butyric acid;
3-[5-Chloro-4-(4-cyano-6-trifluoromethyl-pyridin-3-yl)-2-(5,5-difluoro-2,3,4,5-tetrahydro-benzo[b]azepine-1-sulfonyl)-phenoxy]-propionic acid;
4-[5-Chloro-4-(4-cyano-6-trifluoromethyl-pyridin-3-yl)-2-(5,5-difluoro-2,3,4,5-tetrahydro-benzo[b]azepine-1-sulfonyl)-phenoxy]-butyric acid;
4-[5-Chloro-4-(4-cyano-6-trifluoromethyl-pyridin-3-yl)-2-(4,4-difluoro-3,4-dihydro-2H-quinoline-1-sulfonyl)-phenoxy]-butyric acid;
3-[5-Chloro-4-(4-cyano-6-trifluoromethyl-pyridin-3-yl)-2-(4,4-difluoro-3,4-dihydro-2H-quinoline-1-sulfonyl)-phenoxy]-propionic acid;
[5-Chloro-4-(4-cyano-6-trifluoromethyl-pyridin-3-yl)-2-(4,4-difluoro-3,4-dihydro-2H-quinoline-1-sulfonyl)-phenoxy]-acetic acid;
4-[5-Chloro-4-(4-cyano-6-trifluoromethyl-pyridin-3-yl)-2-(2,3-dihydro-benzo[1,4]thiazine-4-sulfonyl)-phenoxy]-butyric acid;
3-[5-Chloro-4-(4-cyano-6-trifluoromethyl-pyridin-3-yl)-2-(2,3-dihydro-benzo[1,4]thiazine-4-sulfonyl)-phenoxy]-propionic acid;
[5-Chloro-4-(4-cyano-6-trifluoromethyl-pyridin-3-yl)-2-(2,3-dihydro-benzo[1,4]thiazine-4-sulfonyl)-phenoxy]-acetic acid;
5-[2-Chloro-5-(4,4-dimethyl-3,4-dihydro-2H-quinoline-1-sulfonyl)-4-(4-hydroxy-butyl)-phenyl]-2-trifluoromethyl-isonicotinonitrile;
5-[2-Chloro-5-(4,4-dimethyl-3,4-dihydro-2H-quinoline-1-sulfonyl)-4-(3-hydroxy-propyl)-phenyl]-2-trifluoromethyl-isonicotinonitrile;
5-[2-Chloro-5-(4,4-dimethyl-3,4-dihydro-2H-quinoline-1-sulfonyl)-4-(2-hydroxy-ethyl)phenyl]-2-trifluoromethyl-isonicotinonitrile;
5-[2-Chloro-5-(4,4-dimethyl-3,4-dihydro-2H-quinoline-1-sulfonyl)-4-(4-hydroxy-butyl)-phenyl]-pyridine-2,4-dicarbonitrile;
5-[2-Chloro-5-(4,4-dimethyl-3,4-dihydro-2H-quinoline-1-sulfonyl)-4-(3-hydroxy-propyl)-phenyl]-pyridine-2,4-dicarbonitrile;
5-[2-Chloro-5-(4,4-dimethyl-3,4-dihydro-2H-quinoline-1-sulfonyl)-4-(2-hydroxy-ethyl)-phenyl]-pyridine-2,4-dicarbonitrile;
4-[5-Chloro-4-(4,6-dicyano-pyridin-3-yl)-2-(4,4-dimethyl-3,4-dihydro-2H-quinoline-1-sulfonyl)-phenoxy]-butyric acid;
4-[5-Chloro-4-(4-cyano-6-trifluoromethyl-pyridin-3-yl)-2-(5-fluoro-2,3,4,5-tetrahydro-benzo[b]azepine-1-sulfonyl)-phenoxy]-butyric acid;
4-[5-Chloro-4-(4-cyano-6-trifluoromethyl-pyridin-3-yl)-2-(4-fluoro-3,4-dihydro-2H-quinoline-1-sulfonyl)-phenoxy]-butyric acid;
4-[5-Chloro-2-(2,3-dihydro-benzo[1,4]thiazine-4-sulfonyl)-4-(4-ethynyl-6-trifluoromethyl-pyridin-3-yl)-phenoxy]-butyric acid;
4-[5-Chloro-2-(4,4-dimethyl-3,4-dihydro-2H-quinoline-1-sulfonyl)-4-(4-ethynyl-6-trifluoromethyl-pyridin-3-yl)-phenoxy]-butyric acid;
4-[5-Chloro-2-(2,3-dihydro-benzo[1,4]oxazine-4-sulfonyl)-4-(4-ethynyl-6-trifluoromethyl-pyridin-3-yl)-phenoxy]-butyric acid;
3-{1-[4-Chloro-3-(4-cyano-6-trifluoromethyl-pyridin-3-yl)-benzenesulfonyl]-2,3,4,5-tetrahydro-1H-benzo[b]azepin-9-yloxy}-propionic acid;
3-{1-[4-Chloro-3-(4-cyano-6-trifluoromethyl-pyridin-3-yl)-benzenesulfonyl]-1,2,3,4-tetrahydro-quinolin-8-yloxy}-propionic acid;
3-{1-[4-Chloro-3-(4-cyano-6-trifluoromethyl-pyridin-3-yl)-benzenesulfonyl]-4,4-dimethyl-1,2,3,4-tetrahydro-quinolin-8-yloxy}-propionic acid;
4-[5-Chloro-4-(4-cyano-6-trifluoromethyl-pyridin-3-yl)-2-(4,4-dimethyl-3,4-dihydro-2H-quinoline-1-sulfonyl)-phenoxy]-butyric acid ethyl ester;
4-[5-Chloro-4-(4-cyano-6-trifluoromethyl-pyridin-3-yl)-2-(4,4-dimethyl-3,4-dihydro-2H-quinoline-1-sulfonyl)-phenoxy]-butyric acid 1-isopropoxycarbonyloxy-ethyl ester;
4-[5-Chloro-4-(4-cyano-6-trifluoromethyl-pyridin-3-yl)-2-(4,4-dimethyl-3,4-dihydro-2H-quinoline-1-sulfonyl)-phenoxy]-butyric acid 1-cyclohexyloxycarbonyloxy-ethyl ester;
4-[5-Chloro-4-(4-cyano-6-trifluoromethyl-pyridin-3-yl)-2-(4,4-dimethyl-3,4-dihydro-2H-quinoline-1-sulfonyl)-phenoxy]-butyric acid 2,2-dimethyl-propionyloxymethyl ester;
4-[5-Chloro-4-(4-cyano-6-trifluoromethyl-pyridin-3-yl)-2-(4-methoxy-3,4-dihydro-2H-quinoline-1-sulfonyl)-phenoxy]-butyric acid;

3-[5-Chloro-4-(4-cyano-6-trifluoromethyl-pyridin-3-yl)-2-(4-methoxy-3,4-dihydro-2H-quinoline-1-sulfonyl)-phenyl]-propionic acid;

4-[5-Chloro-4-(4,6-dicyano-pyridin-3-yl)-2-(4-methoxy-3,4-dihydro-2H-quinoline-1-sulfonyl)-phenoxy]-butyric acid;

4-[5-Chloro-4-(4-ethynyl-6-trifluoromethyl-pyridin-3-yl)-2-(4-methoxy-3,4-dihydro-2H-quinoline-1-sulfonyl)-phenoxy]-butyric acid; and 4-[5-Chloro-2-(4-methoxy-3,4-dihydro-2H-quinoline-1-sulfonyl)-4-(4-prop-1-ynyl-6-trifluoromethyl-pyridin-3-yl)-phenoxy]-butyric acid.

The compounds of the present invention may be prepared by known organic synthesis techniques, including the methods described in more detail in the Examples. In general, the compounds of structure (I) above may be made by the following reaction schemes, wherein all substituents are as defined above unless indicated otherwise.

Scheme 1

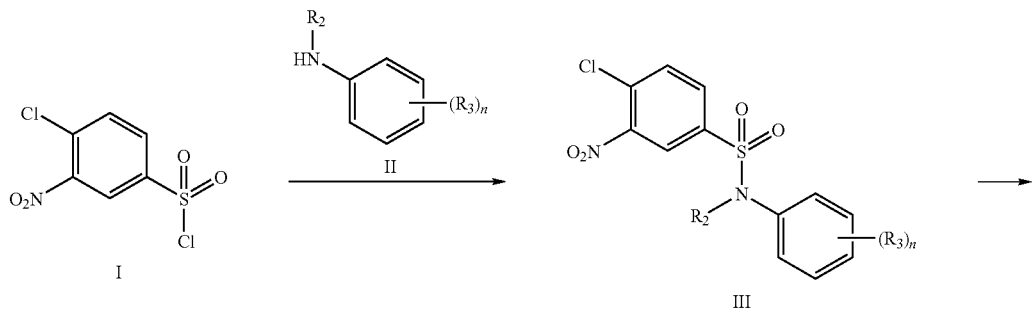

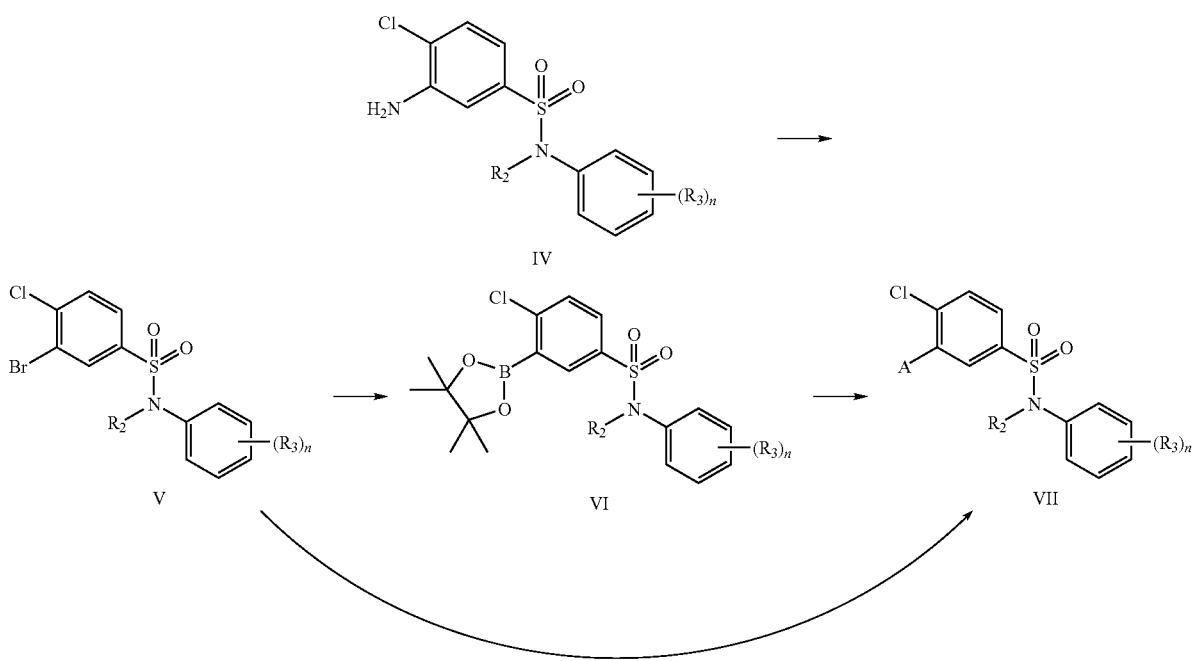

4-Chloro-3-nitrobenzenesulfonyl chloride (I) is coupled with an aniline of formula (II) to form the sulfonamide (III), which is further reduced to aniline (IV). The aniline (IV) is then converted to the bromide (V). Generally the bromide is reacted with bis(pinacolato)diboron to form the boronic ester (VI) or a boronic acid. The boron species (VI or boronic acid) is coupled with a suitable aryl or heteroaryl halide to yield structure (VII). Alternatively, bromide (V) is directly coupled with a suitable aryl or heteroaryl boronic acid to yield (VII). Typically the heteroaryl group exemplified is a substituted pyridine or quinoline.

1-Bromo-2-chloro-4-fluoro-benzene (VIII) is chlorosulfonylated to the benzenesulfonyl chloride (IX) which is further coupled with amines of general formula (II) to provide the fluorosulfonamides (X). Treatment (X) with sodium methoxide affords the aryl ether (XI). Demethylation with boron tribromide or HBr gives the phenol (XII). The phenol is further alkylated with a suitable alkyl halide to yield the aryl ether (XIII). Generation of the intermediate (XIV) is accomplished by the boronic ester formation through a palladium (0) catalyzed reaction. Subsequent Suzuki coupling with a suitable aryl or heteroaryl halide provides compound (XV). If applicable, the protecting group on $R_5$ can be removed after Suzuki coupling reaction.

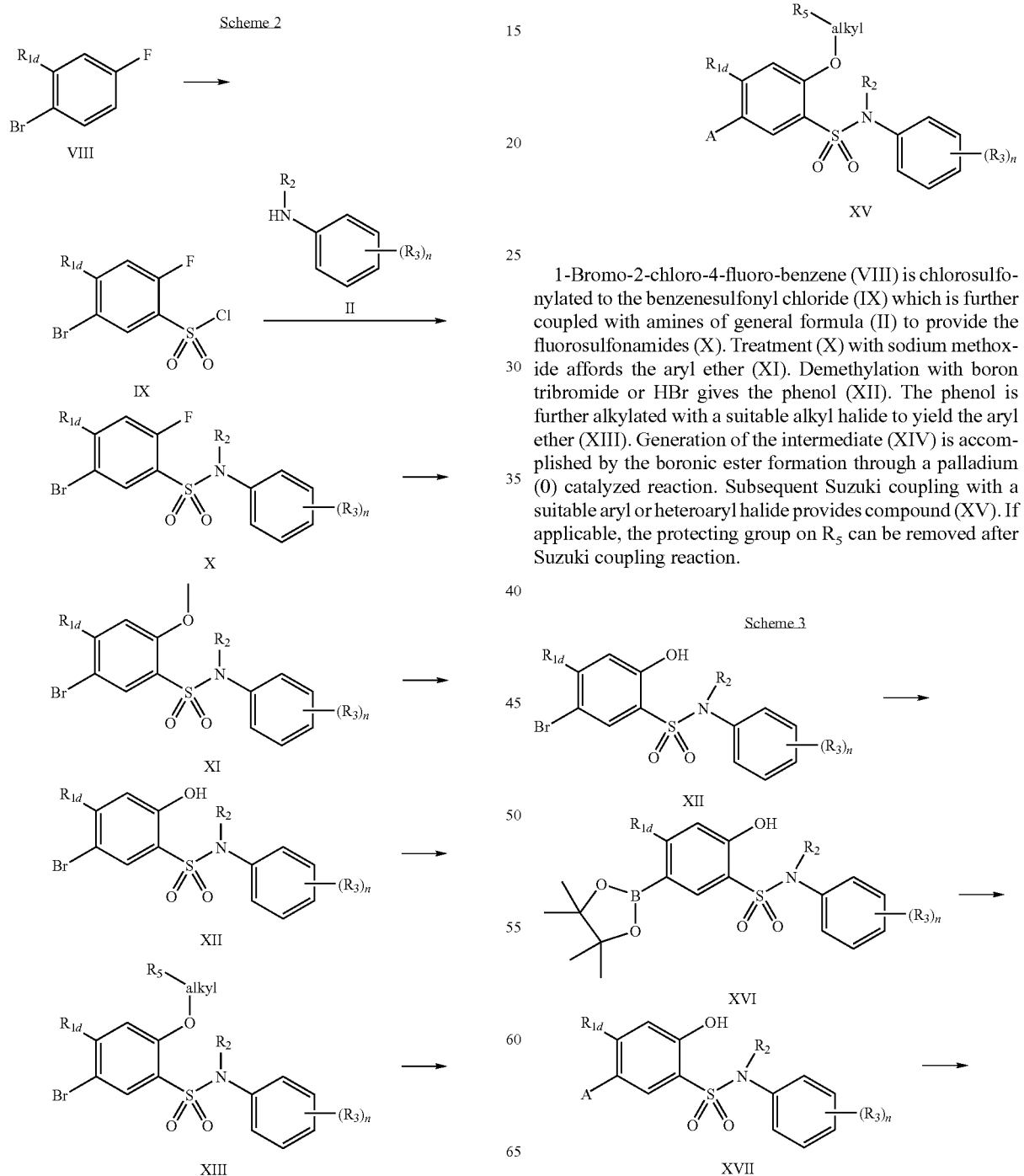

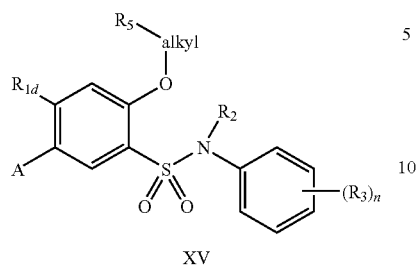

XV

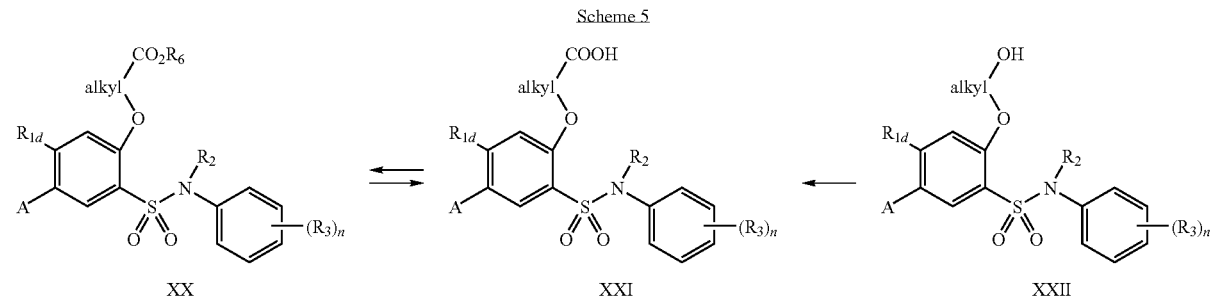

Phenol (XII) may first be converted to the boron ester (XVI) through a palladium (0) catalyzed reaction. Subsequent Suzuki coupling with a suitable aryl or heteroaryl halide affords biaryl alcohol (XVII). This intermediate is further alkylated with a suitable alkyl halide to provide compounds of general formula (XV). If applicable, the protecting group on $R_5$ can be removed after Suzuki coupling reaction.

For compounds containing fluorine in the central ring, bromide (X) is independently converted to its corresponding boron ester (XVIII). Suzuki reaction with a suitable aryl or heteroaryl halide affords fluoro-substituted sulfonamides (XIX)

Compounds of general formula (XX) may be modified to the carboxylic acid (XXI) by deprotection under suitable acidic or basic conditions. Alternatively the alcohol (XXII) may be oxidized using, for example, a ruthenium catalyst to give the corresponding acid (XXI). When desirable the acid (XXI) may in turn be converted to a suitable ester of formula (XX) through coupling with a suitable alcohol.

Scheme 4

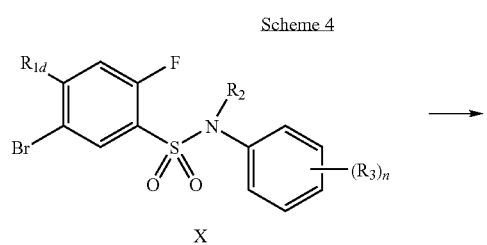

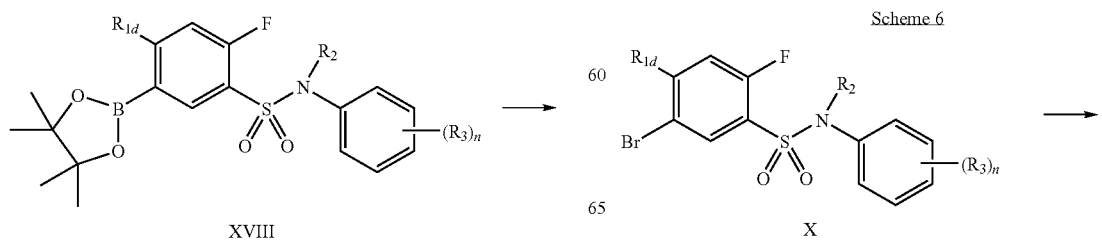

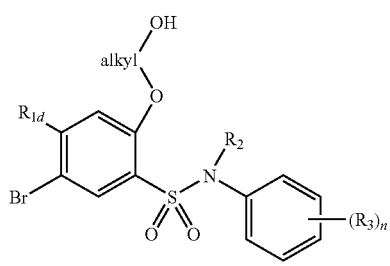

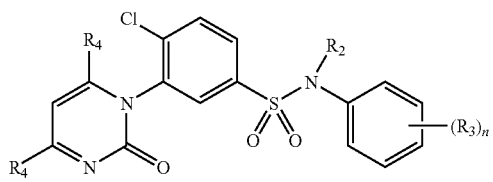

Intermediate aniline (IV) is converted to the urea (XXV) through a condensation with urea at elevated temperature. Further condensation with a suitable di-ketone (XXVI) yields the pyrimidinone (XXVII).

Scheme 8

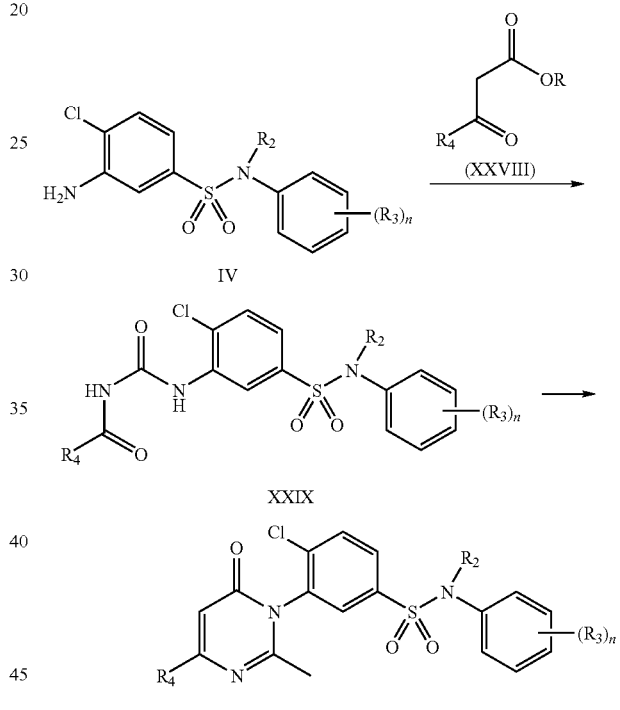

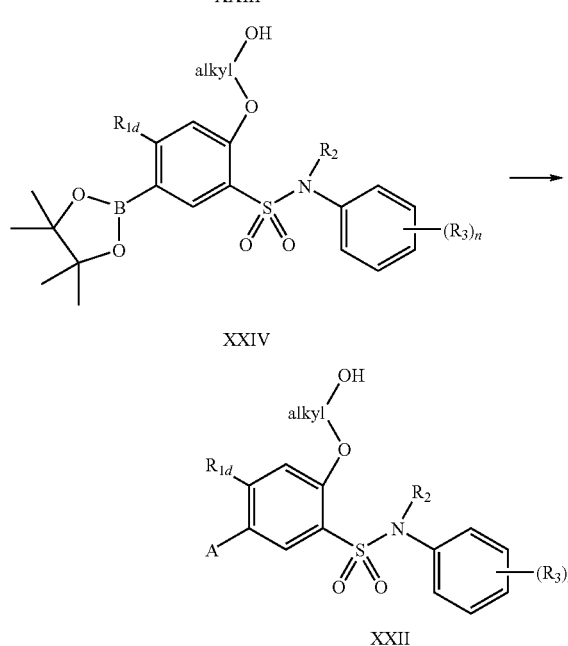

Compounds of general formula (XXII) may also be prepared starting with a displacement reaction of (X) with an alkane diol under basic conditions to give (XXIII). (XXIII) in turn is converted via a palladium (0) catalyzed reaction to provide the boron ester (XXIV) which under Suzuki conditions with a suitable aryl or heteroaryl halide yields (XXII).

Substituted aniline (IV) may be directly condensed with a suitable β-keto ester (XXVIII) to yield intermediate (XX-VIX). Further reaction with acetic anhydride facilitates a ring closure reaction that generates the pyrimidinone (XXX).

Scheme 7

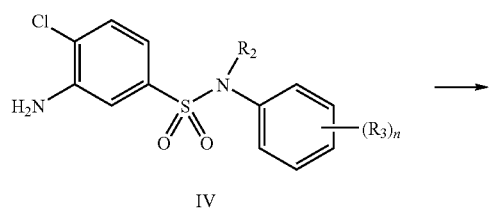

Scheme 9

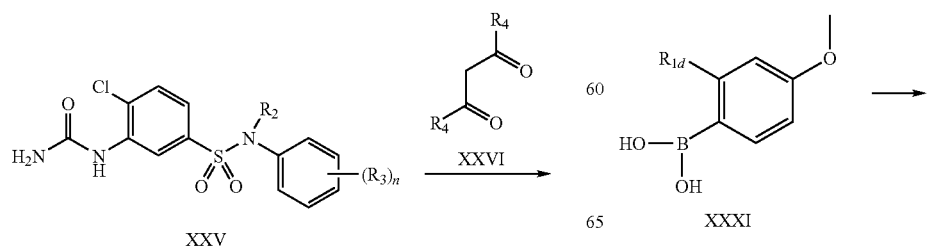

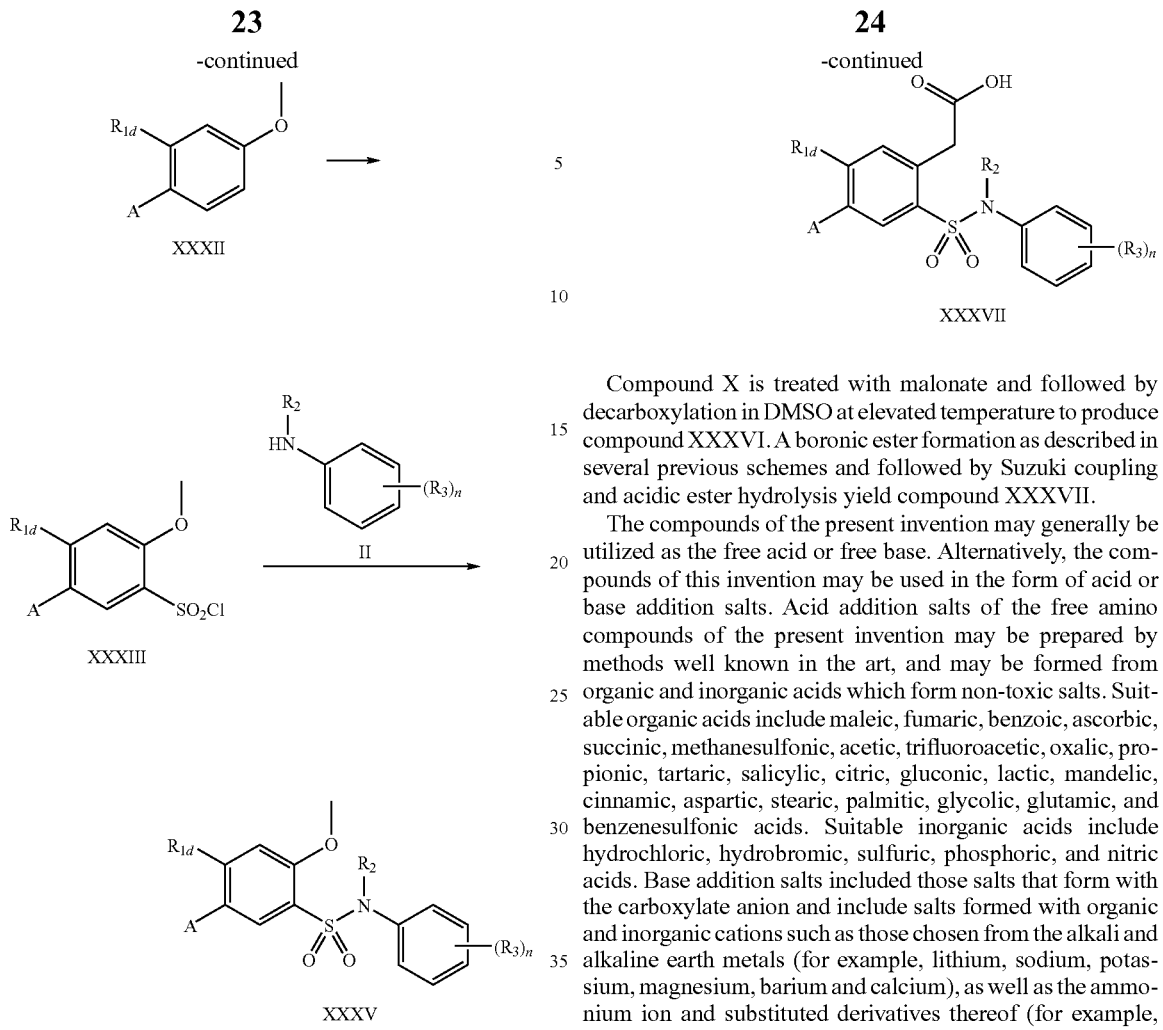

Boronic acid (XXXI) is subjected to Suzuki conditions to yield product (XXXII) which is chlorosulfonylated to the benzenesulfonyl chloride (XXXIII). Further coupling of XXXIII with amines of general formula (II) to provide the sulfonamides (XXXV).

Scheme 10

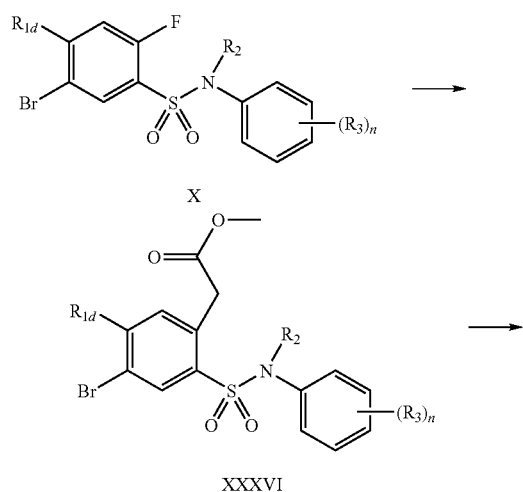

Compound X is treated with malonate and followed by decarboxylation in DMSO at elevated temperature to produce compound XXXVI. A boronic ester formation as described in several previous schemes and followed by Suzuki coupling and acidic ester hydrolysis yield compound XXXVII.

The compounds of the present invention may generally be utilized as the free acid or free base. Alternatively, the compounds of this invention may be used in the form of acid or base addition salts. Acid addition salts of the free amino compounds of the present invention may be prepared by methods well known in the art, and may be formed from organic and inorganic acids which form non-toxic salts. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" of structure (I) is intended to encompass any and all acceptable salt forms.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or acid groups are bonded to any group that, when administered to a patient, cleaves to form the hydroxy, amine or acid groups. Thus, representative examples of prodrugs include (but are not limited to) acetate, formate and benzoate derivatives of alcohol and amine functional groups of the compounds of structure (I). Further, in the case of a carboxylic acid (—COOH), esters may be employed, such as methyl esters, ethyl esters, and the like.

With regard to stereoisomers, the compounds of structure (I) may have chiral centers and may occur as racemates, racemic mixtures and as individual enantiomers or diastereomers. All such isomeric forms are included within the present invention, including mixtures thereof.

The compounds of the present invention may exist in a continuum of solid states ranging from fully amorphous to fully crystalline. Furthermore, some of the crystalline forms of the compounds of structure (I) may exist as polymorphs, which are included in the present invention. In addition, some of the compounds of structure (I) may also form solvates with water or other organic solvents. The term solvate is used herein to describe a molecular complex comprising a compound of the present invention and one or more pharmaceutically acceptable solvent molecules. Such solvates are similarly included within the scope of this invention.

The present invention also includes all pharmaceutically acceptable isotopically labeled compounds of structure (I) where on or more atoms are replaced by atoms having the same atomic number but a different atomic mass. Examples include $^2$H and $^3$H for hydrogen, $^{11}$C, $^{13}$C and $^{14}$C for carbon, $^{36}$Cl for chlorine, $^{18}$F for fluorine, $^{123}$I and $^{125}$I for iodine, $^{13}$N and $^{15}$N for nitrogen, and $^{35}$S for sulfur.

Compounds of the present invention include compounds of structure (I) as defined, including all polymorphs, prodrugs, isomers (including optical, geometric and tautomeric), salts, solvates and isotopes thereof.

The effectiveness of a compound as a GnRH receptor antagonist may be determined by various assay techniques. Assay techniques well known in the field include the use of cultured pituitary cells for measuring GnRH activity (Vale et al., *Endocrinology* 91:562-572, 1972) and the measurement of radioligand binding to rat pituitary membranes (Perrin et al., *Mol. Pharmacol.* 23:44-51, 1983) or to membranes from cells expressing cloned receptors as described below. Other assay techniques include (but are not limited to) measurement of the effects of GnRH receptor antagonists on the inhibition of GnRH-stimulated calcium flux, modulation of phosphoinositol hydrolysis, activation of ERK1/2, mast cell histamine release, and the circulating concentrations of gonadotropins in the castrate animal. Descriptions of these techniques, the synthesis of radiolabeled ligand, the employment of radiolabeled ligand in radioimmunoassay, and the measurement of the effectiveness of a compound as a GnRH receptor antagonist follow.

Cloning and Expression of GnRH Receptors cDNA's of human, rhesus macaque, rabbit, dog and rat GnRH receptors are cloned into pcDNA3.1 (+) (Invitrogen). Full length sequences of all receptors are confirmed by DNA sequencing. HEK 293, CHO, COS-7, or rat basophilic leukemia (RBL) cells are stably transfected with human, rat, or macaque GnRH receptors and high expressing single cell clones ($B_{max} \geq 0.4$ pMol/mg membrane protein) are isolated and maintained in Dulbecco's Modified Eagles Medium (DMEM) with following supplements: 10 mM HEPES; 2 mM L-glutamine; 1 mM Sodium Pyruvate; 50 U/mL penicillin, 50 µg/mL streptomycin; 10% Heat-inactivated Fetal Bovine Serum and 200 µg/mL Geneticin (G-418-Sulfate). Non-essential amino acids (0.1 mM) (Irvine Scientific; Santa Ana, Calif.) are included in the RBL cell media.

In general, initial peptide radioligand binding assays are carried out using membranes from stably transfected RBL cells. RBL stable clones are found to more consistently express high levels of GnRH receptor and are therefore used for subsequent binding studies as well as Ca$^{++}$ flux and inositol phosphate accumulation assays. Transiently transfected COS-7 cells are used for preparation of membranes containing GnRH receptors from multiple species (as well as those of mutant receptors for other studies) because of the convenience for rapidly analyzing multiple receptors. Stably transfected CHO cells are used for ERK1/2 stimulation assays because of superior signal/noise characteristics in this assay.

Membrane Preparation

HEK293 cells stably transfected with the human GnRH receptor are grown for two days after achieving confluence then are harvested by striking tissue culture flasks against a firm surface. Cells are collected by centrifugation at 1000 g for 5 minutes. Cell pellets are resuspended in 5% sucrose and homogenized using a polytron homogenizer for two 15 second homogenization steps. Cell homogenates are then centrifuged for 5 minutes at 3000 g to remove nuclei and the supernatant subsequently centrifuged for 30 minutes at 44,000 g to collect the membrane fraction. The membrane pellet is resuspended in GnRH binding buffer (10 mM HEPES, pH 7.5, 150 mM NaCl and 0.1% BSA) and aliquots immediately snap-frozen in liquid nitrogen and stored at −80° C. Protein content of the membrane suspension is determined using the Bio-Rad protein assay kit (Bio-Rad).

RBL cells stably transfected with the human GnRH receptor are grown to 80% confluency prior to harvesting. The cells are incubated at 37° C. for 10 min in 0.5 mM EDTA/PBS (Ca$^{++}$, Mg$^{++}$ free), and are dislodged from the plate by gentle rapping of the flasks. Cells are collected and pelleted by centrifugation at 1000 g for 5 minutes. Cell pellets are resuspended in buffer (DPBS supplemented with 10 mM MgCl$_2$, 2 mM EGTA, pH=7.4), and cell lysis is performed using a pressure cell and applying N$_2$ at a pressure of 900 psi for 30 min at 4° C. Unbroken cells and larger debris were removed by centrifugation at 1200 g for 10 min at 4° C. The cell membrane supernatant is then centrifuged at 45,000 g and the resulting membrane pellet is resuspended in assay buffer and homogenized on ice using a tissue homogenizer. Protein concentrations are determined using the Coomassie Plus Protein Reagent kit. Membranes are aliquoted and stored at −80° C. until ready for use.

COS-7 cells transiently transfected with GnRH receptors from different species (human, macaque, dog, rabbit, rat) or mutant GnRH receptors are prepared by bulk electroporation. COS-7 cells are obtained from American Type Cell Culture (Manassas, Va.) and are maintained in Dulbecco's modified Eagle's medium (DMEM) (MediaTech Inc., Herndon, Va.) containing 10% fetal bovine serum, 10 mM HEPES, 2 mM L-glutamine, 1 mM sodium pyruvate, 50 U/mL penicillin, 50 µg/mL streptomycin. COS-7 cells are seeded in 500 cm$^2$ tissue culture plates and grown to confluency prior to cell transfection. 5×10$^7$ cells are transfected with 50 µg of the appropriate GnRH receptor DNA construct by electroporation in a BTX ElectroCell Manipulator ECM 600 (Fisher Scientific, Pittsburgh, Pa.) using the following settings: 1000 µF capacitance, 48Ω resistance, and 300 V/cm charging voltage. Transfected cells are cultured for 36-48 h prior to membrane preparation. Transiently transfected COS-7 cells are harvested, washed, and resuspended in membrane buffer (20 mM HEPES pH 7.2, 6 mM MgCl$_2$, 1 mM EDTA). Cells are centrifuged and the cell pellets are resuspended in a small volume of membrane buffer. Cells are lysed by release of pressure following incubation at 900 psi for 30 minutes at 4° C. in a nitrogen chamber. The homogenate is centrifuged at 1000 g for 10 minutes at 4° C. to remove nuclei and cellular debris. Membranes are collected from the supernatant by centrifugation at 44,000 g for 45 minutes at 4° C. Membranes are resuspended in membrane buffer at a concentration of 1 mg/mL, quick-frozen in liquid nitrogen, and stored at −80° C. until used.

Radioligand Binding Assays

Radioligand binding displacement assays using the peptide radioligands are performed in buffer containing 10 mM HEPES, 150 mM NaCl and 0.1% BSA, pH=7.5. Radioligand binding assays employing the use of [$^3$H]-1-(2,6-difluorobenzyl)-3-[(2R)-amino-2-phenethyl]-5-(2-fluoro-3-methoxyphenyl)-6-methyluracil (here the 3-methoxy group is tritiated) are run in buffer containing 50 mM Tris, 150 mM NaCl, 5 mM MgCl$_2$, 0.01% saponin and 0.5 mM EDTA, pH=7.5. Radioligand displacement assays are performed by incubating radioligand ([$^{125}$I-Tyr$^5$, DLeu$^6$, NMeLeu$^7$, Pro$^9$-NEt]GnRH (0.1 nM), [His$^5$, $^{125}$I-DTyr$^6$]GnRH (0.2 nM) (31) or [$^3$H]-1-(2,6-difluorobenzyl)-3-[(2R)-amino-2-phenethyl]-5-(2-fluoro-3-methoxyphenyl)-6-methyluracil (1 nM)), unlabeled competitors at concentrations ranging from 0.3 µM to 10 µM, and membranes for 2 hrs at rt. 10 to 20 µg protein/well is used from membrane preparations for human, monkey and rabbit GnRH receptor. 5 µg/well and 60 µg/well of membranes are used for rat and dog GnRH receptors, respectively. Binding assays are performed in either Millipore 96-well GF/C filtration plates (for ([$^{125}$I-Tyr$^5$, DLeu$^6$, NMeLeu$^7$, Pro$^9$-NEt]GnRH assays), or in 96 well low binding plates, which are subsequently filtered onto GF/C Unifilters. Filters are pretreated with 0.5% PEI for 30 min prior to use. Reactions are terminated by rapid vacuum filtration, and the filters are washed twice with 250 µL ice cold PBS pH=7.4 (0.01% Tween-20 is included in wash media for [His$^5$, $^{125}$I-DTyr$^6$]GnRH and [$^3$H]-1-(2,6-difluorobenzyl)-3-[(2R)-amino-2-phenethyl]-5-(2-fluoro-3-methoxyphenyl)-6-methyluracil radioligands). The filters are dried, and the Millipore filters are monitored for radioactivity using a Cobra II gamma counter (Perkin Elmer Life Sciences). For assays filtered onto the GF/C Unifilter plates, 50 µL scintillation fluid is added to each filter, and radioactivity is monitored using a TopCount NXT. For iodinated radioligands, total radioligand is monitored on a gamma counter, and for the tritiated radioligand, total radioligand is monitored using a Perkin Elmer 1600TR liquid scintillation counter. Total radioligand bound does not exceed 10% of the total radioligand added, a level of depletion which does not appreciably affect the measurement of $K_i$. Nonspecific binding does not exceed 2% of the total radioligand added in any of the displacement assays. Inhibition of radioligand binding is fit to one-site and two-site competition binding equations and the best fit determined using an F-test. For all displacement binding experiments a single site binding model fit best ($p<0.05$). The $K_i$ values are calculated from the IC$_{50}$ values using the method of Cheng and Prusoff (*Biochem. Pharmacol.* 22:3099, 1973) and may be converted to a p$K_i$ value (negative log of the $K_i$ value).

$$K_i = \frac{IC_{50}}{1 + L/K_D}$$

where L=radioligand and $K_D$=affinity of radioligand for receptor. GnRH receptor antagonists of this invention have a $K_i$ of 10 µM or less. In other embodiments of this invention, the GnRH receptor antagonists have a $K_i$ of less than 1 µM, and in many instances have a $K_i$ of less than 0.1 µM (i.e., 100 nM).

Compounds of the present invention as shown in Examples 3 to 19 below (not including chemical intermediates) which were tested in one or more of the peptide competitive human receptor binding assays shown have $K_i$ values of 1 µM or less. Additionally, the following compounds of the present invention as shown in Examples 3 to 19 below (not including chemical intermediates) which were tested in one or more of the peptide competitive human receptor binding assays shown have $K_i$ values of 100 nM or less, while the underlined compounds have $K_i$ values of 10 nM or less:
4-1, 4-2, 4-3, 4-4, 4-5, 4-8, 4-9, 4-10, 4-11, 4-13, 4-14, 4-15, 4-16, 4-17, 4-18, 4-19, 4-20, 4-23, 4-24, 5-1, 5-2, 5-3, 5-4, 5-5, 5-6, 5-7, 6-1, 6-4, 6-5, 7-1, 7-2, 7-3, 7-4, 7-5, 8-2, 8-3, 9-1, 9-2, 10-1, 10-2, 11-1, 11-2, 11-3, 12-1, 12-2, 12-3, 13-1, 13-4, 15-1, 15-2, 15-3, 15-5, 15-6, 15-7, 15-8, 15-9, 15-10, 15-11, 15-12, 15-14, 15-15, 15-16, 15-17, 15-18, 15-19, 15-20, 15-21, 15-22, 15-23, 15-26, 15-28, 15-29, 15-30, 15-31, 15-32, 15-33, 15-34, 15-35, 15-36, 15-38, 15-39, 15-43, 15-44, 16-1, 17-1, 18-1, 18-2, 18-3, and 19-1.

Wheat-germ agglutinin (WGA)-coupled polystyrene (PS) imaging beads (Amersham Biosciences, Piscataway, N.J.) are used in our scintillation proximity assay, permitting whole-plate light imaging with a CCD imaging system, as used by Viewlux (PerkinElmer Life Sciences, Boston, Mass.). Integrity of the receptor and radiolabel is monitored by saturation analysis measured at each time point to ensure a consistent $K_d$. Generally, the GnRH SPA assay produced reliable binding data up to 16 h of incubation. The optimal membrane/SPA bead ratio is determined for each membrane preparation and is typically 40 µg membrane/0.5 mg bead per well. Typically, the instrument is set to measure luminescence for 300 sec using a 613-nm filter to capture the red-shifted emission of the imaging beads and programmed to record at 60-min intervals for 11 h.

Reactions typically consist of 50 µL unlabeled compound various concentrations; 50 µL radiolabeled [$^{125}$I]-His$^5$, D-Tyr$^6$ GnRH ligand (~300 µM, 2200 Ci/mmol; PerkinElmer Life Sciences); and 100 µL membrane/SPA bead added sequentially in assay buffer (10 mM HEPES, 150 mM NaCl, 0.1% bovine serum albumin [BSA; Fraction V], pH 7.5) to low binding 96-well plates (Corning, Palo Alto, Calif.). Cell membrane fractions were prepared as previously described and resuspended in assay buffer.

SPA beads and membrane (rat basophilic leukemia [RBL] cells stably expressing human GnRH-R) are pre-incubated for 2 h prior to compound and radiolabel addition. The complete reaction is briefly shaken and allowed to settle at room temperature in the Viewlux instrument. The amount of bound radioligand is determined at the indicated time intervals.

A single-site binding model is applied for all displacement binding experiments, as determined by a partial F test ($p>0.05$). Dose-response curves for both time points of all compounds tested are normalized to zero and 100% specific binding, and Ki values are calculated using the Cheng-Prusoff equation with a sigmoidal dose-response fit using Prism 4.0 software (GraphPad Software, San Diego, Calif.) using Kd values of 0.2 nM for [$^{125}$I]-His$^5$, D-Tyr$^6$ GnRH, as determined from saturation binding experiments. Hill slopes for all curves routinely range from −0.8 to −1.1.

Radioligand association experiments to estimate the affinity of compounds of the present invention may be initiated by the addition of cell membranes to wells containing an appropriate amount of a radiolabeled tracer, in the absence and presence of a range of concentrations of compound (Sullivan et al., *Biochemical Pharmacology*, 72, 2006, 838-849). All buffers are pre-heated to 37° C. prior to initiation of experiment, and assay plates are maintained at this temperature throughout the experiment. The assay mixture (total volume of 200 µL) is incubated at 37° C. for 1 min to 3 hr (15 time points), and the assay is terminated by rapid vacuum filtration through a cell harvester (UniFilter-96 Filtermate; Packard, PerkinElmer Life Sciences) onto Unifilter GF/B filter plate pretreated with 0.5% polyethylenimine in distilled water for 30 min. After filtration, membranes are washed two times with 400 µL wash buffer (Dulbecco's Phosphate-Buffered Saline, 0.01% Tween-20, pH 7.5). Filter plates are dried, 50 µL scintillation fluid is added (Microscint 20; PerkinElmer Life Sciences), and the plate is monitored for radioactivity using a TopCount NXT at 30% efficiency (PerkinElmer Life Sciences). The total amount of radioligand added to the assay is measured using a 1600TR liquid scintillation counter (PerkinElmer Life Sciences) at 47% efficiency. Analyses are performed using Prism 4.1 Software (GraphPad Software, San Diego, Calif.).

Ca$^{++}$ Flux Measurement

To determine the inhibition of GnRH-stimulated calcium flux in cells expressing the human GnRH receptor, a 96-well plate is seeded with RBL cells stably transfected with the human GnRH receptor at a density of 50,000 cells/well and allowed to attach overnight. Cells were loaded for 1 hour at 37° C. in the following medium: DMEM with 20 mM HEPES, 10% FBS, 2 µM Fluo-4, 0.02% pluronic acid and 2.5 mM probenecid. Cells are washed 4 times with wash buffer (Hanks balanced salt, 20 mM HEPES, 2.5 mM probenecid) after loading, leaving 150 µL in the well after the last wash. GnRH is diluted in 0.1% BSA containing FLIPR buffer (Hanks balanced salt, 20 mM HEPES) to a concentration of 20 nM and dispensed into a low protein binding 96-well plate. Various concentrations of antagonists are prepared in 0.1% BSA/FLIPR buffer in a third 96-well plate. Cell, agonist, and antagonist containing plates are loaded into a fluorometric imaging plate reader (FLIPR) (Molecular Devices, FLIPR384 system, Sunnyvale, Calif.) for liquid handling and fluorescence measurements according to manufacturer's instructions. The instrument is programmed such that antagonist (50 µL at varying concentrations) is added to cell plates and preincubated for 1 minute prior to addition of agonist (50 µL, or 4 nM final concentration of GnRH).

Measurement of [$^3$H]IP Production

The procedure is modified from published protocols (Zhou et al., *J Biol Chem* 270:18853-7). Briefly, RBL cells stably transfected with human GnRH receptors are seeded in 24 well plates at a density of 200,000 cell/well for 24 hrs. Cells are washed once with inositol-free medium containing 10% dialyzed FBS and then labeled with 1 µCi/mL of [myo-$^3$H] inositol. After 20-24 hrs, cells are washed with buffer (140 mM NaCl, 4 mM KCl, 20 mM Hepes, 8.3 mM glucose, 1 mM MgCl$_2$, 1 mM CaCl$_2$ and 0.1% BSA) and treated with native GnRH peptide in the same buffer with or without various concentrations of antagonist and 10 mM LiCl for 1 hour at 37° C. Cells are extracted with 10 mM formic acid at 4° C. for 30 min and loaded to the Dowex AG1-X8 column, washed and eluted with 1M ammonium formate and 0.1M formic acid. The eluate is counted in a scintillation counter. Data from PI hydrolysis assay are plotted using non-linear least square regression by Prism program (GraphPad Software, San Diego, Calif.), from which dose ratio is also calculated. The Schild linear plot is generated from the dose-ratios obtained in four independent experiments by linear regression, the X-intercept is used to determine the affinity of the antagonist.

Activation of ERK1/2

CHO cells stably expressing GnRH receptor are serum-starved for 1 hour, incubated for 5 min with various doses of antagonist, and stimulated with 1 nM GnRH for 5 min at 37° C. Cells are washed once with PBS and harvested directly into 2×SDS sample buffer. Cell extracts are sonicated, heated at 55° C. for 5 min, and subjected to SDS-PAGE. Resolved proteins are transferred onto nitrocellulose membranes. The activated phosphorylated form of ERK1/2 is detected using an anti-phosphoMAPK p42/44 antibody (Cell Signaling Technology, Danvers, Mass.) diluted at 1:3000 in 1% nonfat dried milk in TBST (20 mM Tris-HCl, pH 7.4, 137 mM NaCl, 0.1% Tween20). Total ERK1/2 is detected with the anti-ERK2 antibody (K23, Santa Cruz Biotechnology, Santa Cruz, Calif.). Chemiluminescent detection is performed with SuperSignal West Pico reagent (Pierce, Rockford, Ill.) and quantified on the VersaDoc3000 (Bio-Rad) imaging system. Dose-response data are plotted and analyzed with GraphPad Prism software.

Histamine Release

Rat peritoneal mast cells are obtained in accordance with the current NIH guidelines for the humane and ethical use of laboratory animals and animal welfare, and under an IACUC approved protocol. This method has been previously described for the evaluation of mast cell histamine release by peptide GnRH antagonists (Sundaram et al., *Agents Actions* 25:307-13). Briefly, six male Sprague Dawley rats 240-300 g are sacrificed by CO$_2$ asphyxiation and 40 mL of cold PIPES buffer (25 mM PIPES, 110 mM NaCl, 5 mM KCl, 1 mg/mL glucose, 1 mg/mL BSA and 20 U/mL heparin, pH7.4) is injected into the peritoneal cavity and the abdomen massaged gently. Peritoneal wash is recovered and stored on ice. Cells from the peritoneal wash are washed 3 times with 5 mL PIPES buffer, pooled and purified on a Percoll gradient (Wells and Mann, *Biochem Pharmacol* 32:837-42). For stimulation assays, approximately $2 \times 10^5$ cells in 300 µL PIPES buffer are placed into a 1.5 mL eppendorf tube and test compound (100 µL) is added to the cell suspension. The tubes are incubated at 37° C. for 15 min and the reaction is stopped with 600 µl of ice-cold PIPES buffer. After centrifugation at 4° C., the histamine level in the supernatant is determined by histamine EIA kit from SPI-BIO (Cayman Chemical, Ann Arbor, Mich.) following manufacturer's instructions. 50 µM cetrorelix may be used as a positive control.

LH Suppression in Castrate Macaques

This study in macaques is conducted in accordance with the current NIH guidelines for the humane and ethical use of laboratory animals and animal welfare, and under an IACUC approved protocol. A complete orchiectomy (both testes) is performed approximately 4 weeks prior to the first dose on male cynomolgus monkeys approximately 3.7 to 6.5 years of age (3.7 to 4.8 kg). Sexual maturity is verified by testicular volume and testosterone levels prior to surgery. Blood samples are collected weekly during the 4-week post-surgery recovery period for measurement of testosterone, FSH and LH to verify the rise in gonadotropins. Antagonist is administered to the stomach by nasogastric gavage or by i.v. infusion (over ~15 minutes). Blood samples are collected prior to and after each dose for analysis of serum LH and plasma antagonist concentrations. For the intravenous infusion dose, samples are collected at 0.25, 0.33, 0.5, 1, 1.5, 4, 8, and 24 hrs after the initiation of the infusion. Samples are collected at 0.25, 0.5, 1, 1.5, 2, 4, 8, and 24 hrs postdose for the oral doses. Bioactive LH concentrations in serum samples are measured at the Oregon Regional Primate Center (Beaverton, Oreg.) or the Yerkes Primate Research Center at Emory University using a previously reported mouse Leydig cell bioassay, which detects as little as 3 ng LH/mL using cynomolgus LH RP-1 as the reference preparation (Ellenwood and Resko, *Endocrinology* 107:902-7).

As mentioned above, the GnRH receptor antagonists of this invention may have utility over a wide range of therapeutic applications, and may be used to treat a variety of sex-hormone related conditions in both men and women, as well as mammals in general. For example, such applications include endometriosis, uterine fibroids, polycystic ovarian disease, dysmenorrhea, dyspareunia, menorrhagia, nonmenstrual pelvic pain, pelvic tenderness, induration, general disorders of the menstrual cycle, premature ovarian failure due to chemotherapy or early menopause, hirsutism, precocious puberty, gonadal steroid-dependent neoplasia such as cancers of the prostate, breast and ovary, gonadotrophe pituitary adenomas, adenomyosis sleep apnea, irritable bowel syndrome, premenstrual syndrome, benign prostatic hypertrophy, lower urinary tract symptoms (LUTS), contraception and infertility (e.g., assisted reproductive therapy such as in vitro fertilization). The compounds of this invention may also be useful as an adjunct to treatment of growth hormone deficiency and short stature, and for the treatment of systemic lupus erythematosis.

In addition, the compounds may be useful in combination with androgens, estrogens, progesterones, antiestrogens, antiprogestogens, angiotensin-converting enzyme inhibitors, angiotensin II-receptor antagonists, renin inhibitors, bisphosphonates and other agents for the treatment and/or prevention of disturbances of calcium, phosphate and bone metabolism, aromatase inhibitors, analgesics such as non-steroidal anti-inflammatory drugs (NSAIDS), other COX inhibitors, and anti-NGF agents.

In another embodiment of the invention, pharmaceutical compositions containing one or more GnRH receptor antagonists are disclosed. For the purposes of administration, the compounds of the present invention may be formulated as pharmaceutical compositions. Pharmaceutical compositions of the present invention comprise a GnRH receptor antagonist of the present invention and a pharmaceutically acceptable carrier and/or diluent. The GnRH receptor antagonist is present in the composition in an amount which is effective to treat a particular disorder—that is, in an amount sufficient to achieve GnRH receptor antagonist activity, and preferably with acceptable toxicity to the patient. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a GnRH receptor antagonist, diluents, dispersing and surface active agents, binders, and lubricants. One skilled in this art may further formulate the GnRH receptor antagonist in an appropriate manner, and in accordance with accepted practices, such as those disclosed in *Remington's Pharmaceutical Sciences*, Gennaro, Ed., Mack Publishing Co., Easton, Pa. 1990.

In another embodiment, the present invention provides a method for treating sex-hormone related conditions as discussed above. Such methods include administering of a compound of the present invention to a warm-blooded animal in an amount sufficient to treat the condition. In this context, "treat" includes prophylactic administration. Such methods include systemic administration of a GnRH receptor antagonist of this invention, preferably in the form of a pharmaceutical composition as discussed above. As used herein, systemic administration includes oral and parenteral methods of administration.

For oral administration, suitable pharmaceutical compositions of GnRH receptor antagonists include powders, granules, pills, tablets, lozenges, chews, gels, and capsules as well as liquids, syrups, suspensions, elixirs, and emulsions. The compounds of the invention may also be used in fast dissolving, fast disintegrating dosage forms. These compositions may also include anti-oxidants, flavorants, preservatives, suspending, thickening and emulsifying agents, colorants, flavoring agents and other pharmaceutically acceptable additives. Formulations for oral administration may be formulated to be immediate release or modified release, where modified release includes delayed, sustained, pulsed, controlled, targeted and programmed release.

For parenteral administration, the compounds of the present invention are administered directly into the blood stream, into muscle, or into an internal organ via an intravenous, intraarterial, intraperitoneal, intramuscular, subcutaneous or other injection or infusion. Parenteral formulations may be prepared in aqueous injection solutions which may contain, in addition to the GnRH receptor antagonist, buffers, antioxidants, bacteriostats, salts, carbohydrates, and other additives commonly employed in such solutions. Parenteral administrations may be immediate release or modified release (such as an injected or implanted depot).

Compounds of the present invention may also be administered topically, (intra)dermally, or transdermally to the skin or mucosa. Typical formulations include gels, hydrogels, lotions, solutions, creams, ointments, dressings, foams, skin patches, wafers, implants and microemulsions. Compounds of the present invention may also be administered via inhalation or intranasal administration, such as with a dry powder, an aerosol spray or as drops. Additional routes of administration for compounds of the present invention include intravaginal and rectal (by means of a suppository, pessary or enema), and ocular and aural.

For administration to human patient (or subject), the total daily dose of the compounds of the present invention may be in the range of 1 to 500 mg, typically 5 to 300 mg, more typically 25 to 250 mg, depending, of course on a number of factors including age, sex, and weight of a subject and also on the mode of administration. The total daily dose may be administered singly or in divided doses.

The following examples are provided for purposes of illustration, not limitation. In summary, the GnRH receptor antagonists of this invention may be assayed by the general methods disclosed above, while the following Examples disclose the synthesis of representative compounds of this invention.

EXAMPLES

HPLC Methods for Analyzing the Samples

Retention time, $t_R$, in minutes

Method 1: Column: Synergi 4μ, Max-RP 80A, 50×2 mm; Gradients: from 95% $H_2O$+0.025% TFA/MeCN to 95% MeCN+0.025% TFA/$H_2O$ over 3 min;

Flow rate: 1 mL/min; UV: 222 and 254 nM

Method 2: Column: Synergi 4μ, Max-RP 80A, 50×2 mm; Gradients: from 95% $H_2O$+0.025% TFA/MeCN to 95% MeCN+0.025% TFA/$H_2O$ over 13 min;

Flow rate: 1 mL/min; UV: 222 and 254 nM

Method 3: Column: Phenomenex 5μ, Gemini C18 110A, 150×4.6 mm

Gradients: from 95% $H_2O$+0.04% $NH_4OH$ to 90% MeCN+ 0.04% $NH_4OH$ over 9.86 min. Flow rate: 2.5 mL/min. UV: 222 and 254 nM Method 4: Column: Phenomenex 4μ, RP 80A, 50×2 mm Gradients: from 95% [$H_2O$+10 mM $NH_4CHO$]; 5% [25% MeCN in MeOH] to 5% [$H_2O$+10 mM $NH_4CHO$] over 6.43 min. Flow rate: 1 mL/min. UV: 222 and 254 nM Method 5: Column: Waters Xterra RP, 250×3 mm
Gradients: from 90% [$H_2O$+0.025% TFA] to 95% [MeCN+ 0.025% TFA] over 46 min. Flow rate: 0.8 mL/min. UV: 222 and 254 nM Example 1

5-Bromo-2-trifluoromethyl-isonicotinonitrile

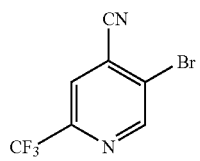

Step 1A: 5-Bromo-2-trifluoromethyl-isonicotinic acid

To a 100 mL round bottom flask equipped with a rubber septa and nitrogen inlet was charged 5 g (22.1 mmol) of 5-bromo-2-trifluoromethylpyridine. To the solid was charged 30 mL of anhydrous THF under a nitrogen atmosphere. After the solution became homogeneous, it was chilled with a −78° C. dry ice/acetone bath. To a separate 100 mL round bottom flask equipped with a rubber septa and nitrogen inlet was charged 3.4 mL (24.2 mL, 1.1 eq) of anhydrous diisopropyl amine. To the solution was charged 16.9 mL of anhydrous THF, placed under a nitrogen atmosphere and chilled with an ice bath. To the solution was carefully added 9.7 mL (24.3 mmol, 1.1 eq) of 2.5 M n-butyl lithium in hexanes. The light yellow LDA solution was chilled with a −78° C. dry ice/acetone bath. A 100 mL pear shaped flask equipped with a rubber septa, nitrogen inlet, stir bar, thermocouple and double headed cannula needle was placed under a nitrogen atmosphere and chilled with a −78° C. dry ice/acetone bath. To a 250 mL round bottom flask equipped with a rubber septa, $CO_2$ inlet, needle outlet and stir bar was charged 30 mL of anhydrous THF. The solution was chilled with a −78° C. dry ice/acetone bath and anhydrous $CO_2$ bubbled through the solution for 10 minutes.

To the empty 100 mL flask was charged 5 mL of the LDA solution. To this was charged 5 mL of the 5-bromo-2-trifluoromethylpyridine solution at such a rate to keep the solution temperature <−60° C. Upon addition, the mixture was stirred for 1 minute then transferred via cannula under positive nitrogen pressure to the $CO_2$ saturated solution. This afforded a light maroon solution. The process was repeated until all starting materials were transferred to the $CO_2$ solution. The $CO_2$ solution was allowed to stir with a −78° C. dry ice/acetone bath for 1 hour. The cooling bath was removed and the solution allowed to warm to ambient temperature.

To the reaction mixture was carefully added 150 mL of saturated ammonium chloride solution. The mixture was transferred to a 500 mL separatory funnel. The lower aqueous phase was separated and the organic phase extracted with 100 mL of 1N sodium hydroxide solution. The combined aqueous phases were extracted with 100 mL of MTBE. The aqueous phase was acidified to ~pH 1 with concentrated hydrochloric acid. The cloudy aqueous mixture was extracted twice with 200 mL of MTBE. The combined organic phases were washed once with 100 mL of brine, dried over magnesium sulfate, filtered and concentrated in vacuo to afford 5-bromo-2-trifluoromethyl-isonicotinic acid (4.7 g) as an off-white solid in a 78% yield.

Step 1B: 5-Bromo-2-trifluoromethyl-isonicotinamide

To a 500 mL round bottom flask equipped with a stir bar, condenser and nitrogen inlet was charged 38.9 g (144 mmol) of 5-bromo-2-trifluoromethyl-isonicotinic acid. To the solid was charged 250 mL of anhydrous DCM followed by 13.2 mL (151 mmol, 1.05 eq) oxalyl chloride. To the mixture was added 0.5 mL of anhydrous dimethylformamide and the mixture was stirred at ambient temperature for 2 h. The reaction was complete as evidenced by HPLC (methanol quench of aliquot). The solvent was removed in vacuo affording an amber oil.

To a 1 L Erlenmeyer flask equipped with a stir bar in an ice-bath was charged 500 mL of aqueous ammonium hydroxide. To the chilled solution was added dropwise the crude acid chloride. The residue was transferred with a small amount of acetonitrile. The mixture was stirred for 20 minutes following addition. The resulting precipitate was collected by filtration and washed with water. The filter cake was dried in vacuo at 45° C. affording 31.8 g of 5-bromo-2-trifluoromethyl-isonicotinamide as an off-white solid in a 82% yield. The compound may also be purified using an ether slurry and collecting the solid.

Step 1C:
5-Bromo-2-trifluoromethyl-isonicotinonitrile

To a 100 mL round bottom equipped with a stir bar, condenser and nitrogen inlet was charged 5.2 g (19.3 mmol) of 5-bromo-2-trifluoromethyl-isonicotinamide. The solid was diluted with 12 mL of phosphorus oxychloride. The mixture was heated at 70° C. for 3 hr. The mixture was cooled to ambient temperature and poured onto ice. The mixture was neutralized with the careful addition of 50% sodium hydroxide. The resulting off-white solid was collected by filtration, washed with water and dried in vacuo at 50° C. for 18 h. This afforded 4.5 g of 5-bromo-2-trifluoromethyl-isonicotinonitrile 1-1 as an off-white solid in a 94% yield. $^1$HNMR ($CDCl_3$), δ, 9.03 (s, 1H), 7.91 (s, 1H).

5-Bromo-4-methyl-2-(trifluoromethyl)-pyridine

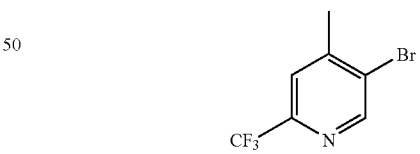

Step 1E:
5-Bromo-4-methyl-2-(trifluoromethyl)pyridine

In a dried 250 mL 3-neck round bottom flask fitted with a stirrer bar, thermometer, and flushed with nitrogen, was placed anhydrous THF (16 mL, Aldrich, inhibitor free) followed by N,N-diisopropylamine (0.895 g, 8.85 mmol, Aldrich, redistilled 99.95% pure). After cooling the stirred solution to −70° C., n-butyl lithium (3.54 mL of a 2.5M solution in hexanes, 8.85 mmol) was added dropwise, keeping the reaction temperature less than −60° C. The resulting solution was stirred at −70° C. for a further 10 min, then warmed to −20° C., before immediately cooling to −90° C. A solution of 5-bromo-2-(trifluoromethyl)pyridine (2 g, 8.85 mmol) in anhydrous THF (8 mL, Aldrich, inhibitor free) was added dropwise, keeping the reaction temperature less than −85° C. The resulting orange solution was stirred at −90° C. for 40 min.

In a separate dried 250 mL 3-neck round bottom flask fitted with a stirrer bar, thermometer, and flushed with nitrogen, was placed anhydrous THF (5 mL, Aldrich, inhibitor free) followed by methyl iodide (5 mL, 80 mmol). The solution was cooled to −90° C. To this was added (via cannula) the solution of the pre-formed lithiated pyridine, controlling the rate so as to keep the reaction temperature of the receiving flask less than −80° C. The resulting dark solution was stirred at −90° C. for a further 15 min (LCMS indicated reaction complete). The reaction was quenched with sat aq. NH$_4$Cl solution (50 mL), then allowed to slowly warm to rt. Organics were extracted with EtOAc (2×50 mL), then the combined organic layers washed with water (50 mL), then brine (50 mL), separated, dried over MgSO$_4$, and then filtered. Concentration in vacuo gave 1.68 g of a brown oil which was purified via short-path vacuum distillation (45-46° C., ca. 5 mmHg) to give 5-bromo-4-methyl-2-(trifluoromethyl)pyridine 1-2 (0.289 g, 14%) as a yellow oil (>97% pure). MS (M+H)$^+$: 241.8, t$_R$=2.458 min (method 1); $^1$H NMR (CDCl$_3$) δ 8.74 (1H, s), 7.56 (1H, s), 2.50 (3H, s).

5-Bromo-2-cyano-4-methylpyridine

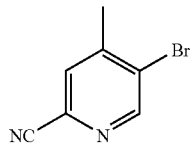

Step 1F: 2,5-Dibromo-4-methylpyridine

2-Amino-5-bromo-4-methylpyridine (2.0 g, 10.7 mmol) was dissolved in 48% aqueous HBr (14 mL, 123 mmol) and cooled to 2° C. in a salt/ice bath. Bromine (1.65 mL, 32.1 mmol) was added dropwise keeping the internal temperature below 2° C. A solution of sodium nitrite (3.69 g, 53.5 mmol) in water (5 mL) was added keeping the internal temperature below 5° C. and stirred for 1 h between 0° C. and 5° C. The pH was adjusted to ~13 by slow addition with cooling of 50% NaOH (aq). After warming to r.t. the reaction was extracted with ether, the organics were dried over MgSO$_4$ and concentrated to give a brown oil. Flash chromatography on silica gel eluting with 5% ether/hexane gave the product as a white solid (1.83 g, 7.29 mmol, 68%). MS [M+H]$^+$: 251.9; t$_R$=2.3 min. (method 1)

Step 1G: (5-Bromo-4-methylpyridin-2-yl)-N-t-butyl carboxylic amide 2,5-Dibromo-4-methylpyridine (1.83 g, 7.29 mmol) was dissolved in toluene (100 mL), cooled to −78° C. and a solution of nBuLi (4.4 mL, 8.8 mmol, 2.0 M in Pentane) was added dropwise and stirred at −78° C. for 2 h. A solution of tBuNCO (1.1 mL, 9.5 mmol) in toluene (3 mL) was added dropwise and stirred for 1 h at −78° C. then warmed to −10° C. and quenched by addition of NH$_4$Cl (aq). After warming to r.t. the reaction was extracted with ether and the organics dried over Na$_2$SO$_4$ and concentrated. The product was used without further purification. MS [M+H]$^+$: 271.0; t$_R$=2.44 min. (method 1)

Step 1H: 5-Bromo-2-cyano-4-methylpyridine

This material was dissolved in toluene (10 mL). POCl$_3$ (10 mL) was added and the solution refluxed for 5 h. After cooling to rt the solvents were removed in vacuo, the reaction was basified by addition of 2 M NaOH (aq) and extracted with ether. The organic extract was washed with brine, dried over MgSO$_4$ and concentrated. Chromatography on silica gel eluting with 20% EtOAc/Hexane gave 5-bromo-2-cyano-4-methylpyridine 1-3 as an off-white crystalline solid (920 mg, 4.7 mmol, 64% over 2 steps). $^1$H NMR (300 MHz, CDCl$_3$) 8.73 (1H, s), 7.56 (1H, s), 2.46 (3H, s). MS [M+H]$^+$: 196.8.0; t$_R$=2.04 min. (method 1).

2-Bromo-3,5-dichloro-6-methylpyridine

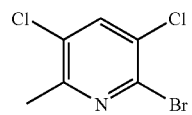

Step 1I: 2-Bromo-3,5-dichloro-6-methylpyridine

2-Amino-3,5-dichloro-6-methylpyridine (3.54 g, 20 mmol) was suspended in aqueous 48% HBr solution at rt and the mixture was cooled to −20° C. This suspension was maintained at −20° C. while bromine (2.87 mL, 56 mmol) was added dropwise. The resultant paste was stirred for 30 minutes at this temperature before the dropwise addition of a cooled solution of sodium nitrite (3.59 g, 52 mmol) in water (5 mL). At this point the reaction mixture was allowed to warm to rt. After stirring for a further 60 minutes, the mixture was again cooled to −20° C. and treated with a solution of sodium hydroxide (16 g, 0.4 mol) in water (20 mL). This mixture was extracted with ethyl acetate and the organic layer washed with water and then brine solution. The organic solution was dried over MgSO$_4$, filtered and the residue obtained from solvent evaporation was purified using silica gel chromatography [eluent: 10% ethyl acetate in hexane]. 2-Bromo-3,5-dichloro-6-methylpyridine 1-4 (2.14 g, 45%) was obtained as a solid.

5-Bromo-4-chloro-2-methyl-pyridine

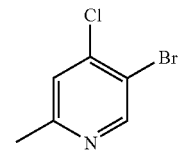

Step 1J: 5-Bromo-2-methyl-4-nitropyridine oxide

A mixture of 5-bromo-2-methyl-pyridine (10.0 g, 58.0 mmol), hydrogen peroxide (28 mL, 30% in water) in acetic acid (28 mL) was heated to 90° C. for 2 days, then additional hydrogen peroxide (14 mL) was added. The mixture was heated for another 1 day. Upon cooling to rt, it was extracted with CHCl₃ three times. The organic solution was then dried over MgSO₄, and concentrated to yield the crude pyridine oxide. MS: 187.7 (M+H)⁺; $t_R$=2.22 min. (method 1).

The above pyridine oxide was added into a mixture of HNO₃ (18 mL) and H₂SO₄ (16 mL) at 0° C. The mixture was then heated to 90° C. for 48 hrs, allowed to cool to rt and poured into iced water resulting in a precipitation. The solid was filtered and dried to afford 5-bromo-2-methyl-4-nitropyridine oxide (7.32 g). MS: 232.7 (M+H)⁺; $t_R$=1.94 min. (method 1).

Step 1K: 5-Bromo-4-chloro-2-methylpyridine

5-Bromo-2-methyl-4-nitropyridine oxide (7.0 g, 30 mmol) was refluxed in conc. HCl (80 mL) for 16 hrs. The mixture was allowed to cool to rt, partially concentrated and then neutralized by NaOH (10N) to pH 7. The crude was partitioned between CHCl₃ and water. The organic solution was separated, dried and concentrated to yield 5-bromo-4-chloro-2-methylpyridine oxide as a white solid (6.71 g). MS [M+H]⁺: 223.7; $t_R$=1.91 min. (method 1).

To the solid (6.71 g, 30 mmol) in CHCl₃ (60 mL) at 0° C., was added POCl₃ (7.85 mL, 90 mmol) slowly. The mixture was heated to reflux for 3 hrs and allowed to cool to rt. The product was extracted by CHCl₃. The extracted solution was washed with sat. NaHCO₃, water and dried over MgSO₄. The filtrate was then concentrated to yield 5-bromo-4-chloro-2-methylpyridine 1-5 as a yellow oil (5.9 g). MS [M+H—Cl]⁺: 171.9; $t_R$=2.13 min. (method 1)

Example 2

4,4-Dimethyl-1,2,3,4-tetrahydro-quinoline

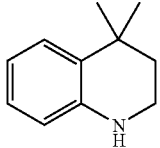

Step 2A: 3-Methyl-but-2-enoic acid phenylamide

To 3,3-dimethylacryloyl chloride (4.8 mL, 43.2 mmol) in dry DCM (100 mL), was added aniline (4.02 g, 43.2 mmol) followed by diisopropylethylamine (14.28 mL, 86.4 mmol). The mixture was stirred at ambient temperature for 2 hrs. Saturated sodium bicarbonate was added to quench the reaction. The organic layer was separated and washed with sat NaHCO₃ (50 mL) and water (50 mL×2). The resulting solution was dried over MgSO₄ and the filtrate evaporated to afford 3-methyl-but-2-enoic acid phenylamide as a brown solid in quantitative yield (7.6 g). MS: 176.0 (M+H)⁺; $t_R$=2.40 min (method 1).

Step 2B: 4,4-Dimethyl-3,4-dihydro-1H-quinolin-2-one

To 3-methyl-but-2-enoic acid phenylamide (7.6 g, 43 mmol) in DCM (100 mL) was added AlCl₃ (8.7 g, 65.2 mmol) and the mixture was stirred at 50° C. for 2 hrs. After cooling to rt, the mixture was treated with 1N HCl (50 mL) and extracted with DCM (30 mL×2). This solution was then washed with brine (50 mL×2) and dried over MgSO₄. The filtrate was evaporated to afford 4,4-dimethyl-3,4-dihydro-1H-quinolin-2-one as a brown solid in quantitative yield (7.6 g). MS: 176.0 (M+H)⁺; $t_R$=1.91 min (method 1).

Step 2C: 4,4-Dimethyl-1,2,3,4-tetrahydro-quinoline

To 4,4-dimethyl-3,4-dihydro-1H-quinolin-2-one (7.6 g, 43 mmol) in THF (100 mL), was added lithium aluminum hydride (5 g, 134 mmole) portion wise with ice bath. The reaction mixture was warmed to 50° C. and stirred overnight. The reaction mixture was cooled to rt and treated with water (5 mL), 10% sodium hydroxide aqueous solution (5 mL) and water (15 mL). The resulting mixture was stirred for another 10 minutes. The mixture was filtered through Celite and the Celite was washed with ethyl acetate to a volume of approximately 50 mL. The resulting ethyl acetate solution was washed with brine (50 mL×2) and dried over MgSO₄. Concentration of the filtrate and purification by silica gel column chromatography eluting with hexane/ethyl acetate (9/1) yielded 4,4-dimethyl-1,2,3,4-tetrahydro-quinoline 2-1 as a brown oil (6.0 g, 87% yield). MS: 162.0 (M+H)⁺; $t_R$=1.47 min (method 1).

1,2,3,5-Tetrahydro-4,1-benzoxazepine

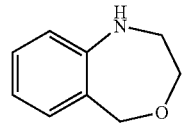

Step 2D: 2-Chloro-N-(2-hydroxymethyl-phenyl)acetamide

To chloroacetyl chloride (3.0 mL, 37.7 mmol) in dry DCM (100 mL) was added 2-aminobenzyl alcohol (4.3 g, 34.9 mmol) followed by addition of diisopropylethylamine (13.0 mL, 78.6 mmol). The mixture was stirred at ambient temperature for 2 hrs. The mixture was quenched with saturated sodium bicarbonate. The organic layer was separated and washed with sat NaHCO₃ (50 mL) and water (50 mL×2). The resulting solution was dried over MgSO₄ and evaporated to afford 2-chloro-N-(2-hydroxymethyl-phenyl)acetamide as a brown oil in quantitative yield (7.0 g). MS: 182.0 (M–H₂O)⁺; $t_R$=1.46 min (method 1).

Step 2E: 1,5-Dihydro-4,1-benzoxazepin-2-one

To 2-chloro-N-(2-hydroxymethyl-phenyl)acetamide (7.0 g, 35 mmol) in isopropyl alcohol (100 mL) was added 50% w/w sodium hydroxide aqueous solution (4 mL, 50 mmol). The mixture was stirred at rt overnight. The mixture was extracted with DCM (50 mL×2). The resulting solution was then washed with brine (50 mL×2) and dried over MgSO₄. The solvent was evaporated to afford 1,5-dihydro-4,1-benzoxazepin-2-one as a brown solid in 65% yield (3.7 g). MS: 163.0 (M+H)⁺; $t_R$=1.56 min (method 1).

Step 2F: 1,2,3,5-Tetrahydro-4,1-benzoxazepine

To 1,5-dihydro-4,1-benzoxazepin-2-one (3.7 g, 22.7 mmol) in THF (75 mL) cooled with an ice bath was added lithium aluminum hydride (2.6 g, 68 mmole) portion wise. The reaction mixture was warmed to 80° C. and stirred for 2 hrs. This mixture was then cooled to rt and was treated with water (2.7 mL), 10% sodium hydroxide aqueous solution (2.7 mL) and water (8.1 mL). The resulting mixture was stirred for another 10 minutes before filtration through Celite. The Celite was washed with ethyl acetate and the organic solution was washed with brine (30 mL×2) before drying over MgSO$_4$. Concentration of the filtrate and purification of the residue by silica gel column chromatography eluting with chloroform/methanol (99/1) yielded 1,2,3,5-tetrahydro-4,1-benzoxazepine 2-2 as a brown solid (1.65 g, 48% yield). MS: 150.0 (M+H)$^+$; t$_R$=1.02 min (method 1).

1-Methyl-6,7,8,9-tetrahydro-5-oxa-9-aza-benzocycloheptene

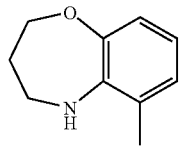

Step 2G: (2-Hydroxy-6-methyl-phenyl)-carbamic acid tert-butyl ester

To a solution of THF (240 mL) containing 2-amino-3-methyl-phenol (10.0 g, 81.4 mmol) was added di-tert-butyl dicarbonate (20.6 mL, 89.4 mmol) and triethylamine (21.4 mL, 244 mmol). The mixture was heated at 50° C. for 16 hrs. After the removal of THF, the mixture was repartitioned with ethyl acetate (300 mL) and 0.5 N HCl (100 mL). The organic layer was then washed with additional 0.2 N HCl (100 mL), sat. NaHCO$_3$ (100 mL), and brine (2×100 mL), and was dried over MgSO$_4$. Concentration and purification by silica gel column chromatography eluting with hexane/ethyl acetate (4/1) yielded (2-hydroxy-6-methyl-phenyl)-carbamic acid tert-butyl ester as a pale yellow solid (4.5 g). MS: 124.0 (M+H−Boc)$^+$; t$_R$=2.20 min (method 1).

Step 2H: [2-(3-Bromo-propoxy)-6-methyl-phenyl]-carbamic acid tert-butyl ester

To (2-hydroxy-6-methyl-phenyl)-carbamic acid tert-butyl ester (5.5 g, 24.6 mmol) in acetonitrile (200 mL) was added 1,3-dibromopropane (17.5 mL, 172 mmol), and potassium carbonate (27.0 g, 196 mmol). The mixture was heated at 55° C. for 2.5 hrs, followed by a filtration to remove solids. The filtrate was concentrated and repartitioned with ethyl acetate (250 mL) and water (150 mL). The organic layer was then washed with brine (150 mL), dried over MgSO$_4$, and evaporated affording [2-(3-bromo-propoxy)-6-methyl-phenyl]-carbamic acid tert-butyl ester (quantitative yield). MS: 243.8 (M+H−Boc)$^+$; t$_R$=2.62 min (method 1).

Step 2I: 2-(3-Bromo-propoxy)-6-methyl-phenylamine

[2-(3-Bromo-propoxy)-6-methyl-phenyl]-carbamic acid tert-butyl ester was stirred in 4 M HCl in dioxane (50 mL) for 1.5 hrs with the formation of a white precipitation. Filtration, followed by several washes with ether, afforded 2-(3-bromo-propoxy)-6-methyl-phenylamine as a white solid (4.8 g). MS: 244.0 (M+H)$^+$; t$_R$=1.80 min (method 1).

Step 2J: 1-Methyl-6,7,8,9-tetrahydro-5-oxa-9-aza-benzocycloheptene

To 2-(3-bromo-propoxy)-6-methyl-phenylamine (4.8 g, 20 mmol) in acetonitrile (200 mL) was added potassium carbonate (13.8 g, 100 mmol). The mixture was heated at 70° C. for 24 hrs, followed by the filtration to remove solids. After evaporation, the mixture was repartitioned with ethyl acetate (250 mL) and water (150 mL). The organic layer was then washed with brine (150 mL) and dried over MgSO$_4$. Evaporation followed by purification by silica gel column chromatography eluting with hexane/ethyl acetate (11/1 to 4/1) yielded 1-methyl-6,7,8,9-tetrahydro-5-oxa-9-aza-benzocycloheptene 2-3 as a pale yellow oil (2.25 g). MS: 164.0 (M+H)$^+$; t$_R$=1.191 min (method 1). NMR (CDCl$_3$), δ, 6.789-6.858 (2H, m), 6.664 (1H, t), 4.158 (2H, t), 3.343 (2H, t), 2.198 (3H, s), 1.191-2.067 (2H, m).

6,7,8,9-Tetrahydro-5-oxa-9-aza-benzocycloheptene

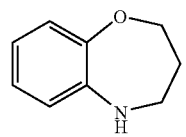

Step 2K: Chroman-4-one oxime

To a solution of 4-chromanone (10 g, 67.6 mmol) in methanol (150 mL) was added triethylamine (15 mL, 108.1 mmol) and hydroxylamine hydrochloride (7.5 g, 108.1 mmol). The mixture was stirred at rt for 16 hrs. The solvent was evaporated giving a residue which was dissolved in ethyl acetate and extracted with water. The organic layer was separated and dried over anhydrous sodium sulfate. Evaporation of the filtrate afforded chroman-4-one oxime (16.1 g, 100%) as a white crystalline solid. MS: 164.0 (M+H)$^+$; t$_R$=1.99 min (method 1).

Step 2L: 6,7-Dihydro-9H-5-oxa-9-aza-benzocyclohepten-8-one

Under a stream of N$_2$ gas was mixed chroman-4-one oxime (1 g, 6.1 mmol) with PPA (13 g, 79.8 mmol). The resulting mixture was heated at 130° C. for 1 hour. At this point the mixture was poured into ice and stirred until homogeneous. The mixture was extracted with ethyl acetate and the organic solution was further washed with water and brine before drying over anhydrous sodium sulfate. Concentration of the filtrate gave a residue that was purified by silica gel chromatography (eluent: 1/1 ethyl acetate/hexane) to yield 6,7-dihydro-9H-5-oxa-9-aza-benzocyclohepten-8-one (0.13 g, 13%). MS: 164.0 (M+H)$^+$; t$_R$=1.70 min (method 1).

Step 2M: 6,7,8,9-Tetrahydro-5-oxa-9-aza-benzocycloheptene 6,7-Dihydro-9H-5-oxa-9-aza-benzocyclohepten-8-one (0.13 g, 0.8 mmol) was dissolved in THF and to this solution was added a 1M solution of borane in THF (1.59 mL, 1.6 mmol). The mixture was heated at 70° C. for 2 hrs. At this time a further portion of borane solution (1.59 mL, 1.6 mmol) was added and heating was continued for another 2 hrs. The solvent was evaporated at this point and the residue was dissolved in ethyl acetate. Extraction of the solution with 1M sodium hydroxide solution and then brine afforded an organic layer that was dried over anhydrous sodium sulfate. The filtrate was evaporated to afford 6,7,8,9-tetrahydro-5-oxa-9-aza-benzocycloheptene 2-4 (0.15 g, 100%) that was used without further purification. MS: 150.0 (M+H)$^+$; $t_R$=0.57 min (method 1).

Example 3

4-Chloro-5-(4-chloro-6-methyl-pyridin-3-yl)-2-fluoro-N-(2-methoxy-phenyl)-N-methyl-benzenesulfonamide

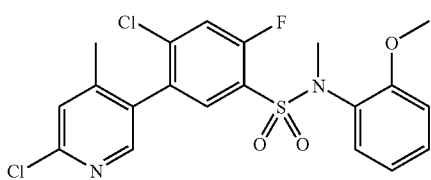

Step 3A:
5-Bromo-4-chloro-2-fluoro-benzenesulfonyl chloride

1-Bromo-2-chloro-4-fluoro-benzene (25.0 g, 119 mmol) in chlorosulfonic acid (48 mL) was stirred at 95° C. for 2 hrs. After the mixture was cooled to rt, it was added dropwise to ca. 500 mL of ice-water under stirring with the formation of the white precipitations. The filtration of the mixture afforded 5-bromo-4-chloro-2-fluoro-benzenesulfonyl chloride as the white solid (31.5 g) that was used without further purification.

Step 3B: 5-Bromo-4-chloro-2-fluoro-N-(2-methoxy-phenyl)-N-methyl-benzenesulfonamide To a solution of DCM (36 mL) containing 5-bromo-4-chloro-2-fluoro-benzenesulfonyl chloride (5.5 g, 17.9 mmol) was added (2-methoxy-phenyl)-methyl-amine (2.6 g, 18.8 mmol) and triethylamine (7.1 mL, 53.7 mmol). The mixture was stirred for 16 hrs. 100 mL of DCM and 100 mL of water were added. The organic layer was separated, washed with water (2×50 mL) and dried over MgSO$_4$. Concentration and purification by silica gel column chromatography eluting with hexane/ethyl acetate (9/1 to 5/1) yielded 5-bromo-4-chloro-2-fluoro-N-(2-methoxy-phenyl)-N-methyl-benzenesulfonamide as a white solid (4.5 g). MS: 408.0 (M+H)$^+$; $t_R$=8.83 min (method 2). NMR (CDCl$_3$), δ, 7.925 (1H, d, J=6.9 Hz), 7.257-7.367 (3H, m), 6.959 (1H, m), 6.831 (1H, d, m), 3.490 (3H, s), 3.339 (3H, d, J=2.4 Hz).

Step 3C: 4-Chloro-2-fluoro-N-(2-methoxy-phenyl)-N-methyl-5-(4,4,5,5-tetramethyl-[1,3]dioxolan-2-yl)-benzenesulfonamide A mixture of 5-bromo-4-chloro-2-fluoro-N-(2-methoxy-phenyl)-N-methyl-benzenesulfonamide (0.81 g, 2.0 mmol), bis(pinacolato)diboron (0.64 g, 2.5 mmol), PdCl$_2$(dppf)$_2$ (73 mg, 0.1 mmol) and potassium acetate (0.59 g, 6.0 mmol) in dioxane (10 mL) was degassed with N$_2$ for 5 min. The vessel was sealed and heated at 90° C. for 16 hrs. The mixture was filtered through Celite to remove solids. The Celite was washed with ethyl acetate several times. The combined solution was washed with water and brine, then was dried over MgSO$_4$. After filtration and concentration, the crude material was purified by silica gel column chromatography eluting with ethyl acetate in hexanes (1/3 to 1/1) to yield 4-chloro-2-fluoro-N-(2-methoxy-phenyl)-N-methyl-5-(4,4,5,5-tetramethyl-[1,3]dioxolan-2-yl)-benzenesulfonamide as a white foam (0.61 g). MS: 455.7 (M+H)$^+$; $t_R$=3.213 min (method 1).

Step 3D: 4-Chloro-5-(4-chloro-6-methyl-pyridin-3-yl)-2-fluoro-N-(2-methoxy-phenyl)-N-methyl-benzenesulfonamide 4-Chloro-2-fluoro-N-(2-methoxy-phenyl)-N-methyl-5-(4,4,5,5-tetramethyl-[1,3]dioxolan-2-yl)-benzenesulfonamide (57 mg, 0.125 mmol), 5-bromo-4-chloro-2-methyl-pyridine (21 mg, 0.1 mmol), Pd(Ph$_3$P)$_4$ (12 mg, 0.01 mmol), K$_2$CO$_3$ (69 mg, 0.5 mmol) in a mixture of dioxane (1.5 mL) and water (0.15 mL) was degassed with N$_2$ for 5 min. The reaction vessel was sealed and heated at 85° C. for 14 hrs. After the filtration, the mixture was purified by prep. LCMS to afford 4-chloro-5-(4-chloro-6-methyl-pyridin-3-yl)-2-fluoro-N-(2-methoxy-phenyl)-N-methyl-benzenesulfonamide 3-1. MS: 454.7 (M+H)$^+$; $t_R$=7.77 min (method 2). NMR (CDCl$_3$), δ, 8.350 (1H, s), 7.549 (1H, d, J=6.9 Hz), 7.257-7.436 (5H, m), 6.932 (1H, m), 6.817 (1H, m), 3.513 (3H, s), 3.389 (3H, d, J=2.1 Hz), 2.656 (3H, s).

1-[4-Chloro-5-(4-chloro-6-methyl-pyridin-3-yl)-2-fluoro-benzenesulfonyl]-1,2,3,4-tetrahydro-quinoline 3-2 was prepared in a similar fashion. MS: 451.9 (M+H)$^+$; $t_R$=10.48 min (method 3).

Example 4

1-[4-Chloro-3-(6-chloro-4-methyl-pyridin-3-yl)-benzenesulfonyl]-2,3,4,5-tetrahydro-1H-1-benzazepine

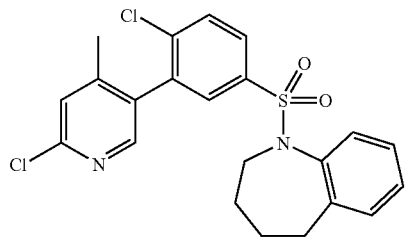

Step 4A: 1-(3-Nitro-4-chloro-benzenesulfonyl-2,3,4,5-tetrahydro-1H-benzo[b]azepine To 4-chloro-3-nitrobenzenesulfonyl chloride (1.0 g, 3.9 mmol) in dry DCM (10 mL), was added 2,3,4,5-tetrahydro-1H-benzo[b]azepine (0.57 g, 3.9 mmol). Diisopropylethylamine (1.3 mL, 7.8 mmol) was added and the mixture was stirred at ambient temperature for 16 hrs. DCM (20 mL) and 30 mL of water were added. The DCM layer was separated, washed with brine (20 mL×2), dried over MgSO$_4$ and evaporated to give 1-(3-nitro-4-chloro-benzenesulfonyl)-2,3,4,5-tetrahydro-1H-benzo[b]azepine 4-1 as a yellow solid (1.3 g, 85% yield). MS: 367 (M+H)$^+$; $t_R$=2.98 min (method 1).

The following intermediate compounds were similarly prepared using this procedure:

4-Chloro-N-(2-methoxy-phenyl)-N-methyl-3-nitro-benzenesulfonamide, MS: 357 (M+H)+; $t_R$=2.85 min (method 1);

1-(4-Chloro-3-nitro-benzenesulfonyl)-1,2,3,4-tetrahydro-quinoline, MS: 353 (M+H)+; $t_R$=2.94 min (method 1);

4-(4-Chloro-3-nitro-benzenesulfonyl)-3,4-dihydro-2H-benzo[1,4]oxazine, MS: 355 (M+H)+; $t_R$=2.88 min (method 1);

1-(4-Chloro-3-nitro-benzenesulfonyl)-4,4-dimethyl-1,2,3,4-tetrahydro-quinoline, MS: 381 (M+H)+; $t_R$=3.06 min (method 1);

1-(4-Chloro-3-nitro-benzenesulfonyl)-2-methyl-1,2,3,4-tetrahydro-quinoline, MS: 367 (M+H)+; $t_R$=2.57 min (method 1);

1-(4-Chloro-3-nitro-benzenesulfonyl)-1,2,3,5-tetrahydro-benzo[e][1,4]oxazepine, MS: 369 (M+H)+; $t_R$=2.35 min (method 1);

1-(4-Chloro-3-nitro-benzenesulfonyl)-8-methyl-1,2,3,4-tetrahydro-quinoline, MS: 367 (M+H)+; $t_R$=2.56 min (method 1);

1-(4-Chloro-3-nitro-benzenesulfonyl)-1,2,3,4-tetrahydro-benzo[b]azepin-5-one, MS: 381 (M+H)+; $t_R$=2.33 min (method 1);

1-(4-Methyl-3-nitro-benzenesulfonyl)-2,3,4,5-tetrahydro-1H-benzo[b]azepine, MS: 347 (M+H)+; $t_R$=2.95 min (method 1);

9-(4-Chloro-3-nitro-benzenesulfonyl)-1-methyl-6,7,8,9-tetrahydro-5-oxa-9-aza-benzocycloheptene, $t_R$=5.42 min (method 5), 1H NMR: (CDCl3), δ, 8.101 (1H, s), 7.572-7.684 (2H, m), 7.172-7.225 (1H, m), 7.073 (1H, d, J=7.5 Hz), 6.821 (1H, d, J=7.8 Hz), 4.486 (1H, d, J=15 Hz), 4.095 (1H, d, J=12.3 Hz), 3.381 (1H, t), 3.151 (1H, t), 2.502 (3H, s), 1.971-2.022 (1H, m), 1.515-1.574 (1H, m); and 9-(4-Chloro-3-nitro-benzenesulfonyl)-6,7,8,9-tetrahydro-5-oxa-9-aza-benzocycloheptene, MS: 368 (M+H)+; $t_R$=9.80 min (method 6).

Step 4B: 1-(3-Bromo-4-chloro-benzenesulfonyl)-2,3,4,5-tetrahydro-1H-1-benzazepine To 1-(3-nitro-4-chloro-benzenesulfonyl)-2,3,4,5-tetrahydro-1H-benzo[b]azepine (0.63 g, 1.70 mmol) in THF (4 mL) and water (4 mL) was added sodium hydrosulfite (1.47 g, 8.5 mmol). The mixture was stirred at ambient temperature for 2 hrs, followed by partition between ethyl acetate (4 mL) and sat. NH4Cl (4 mL). The organic layer was then washed with brine (2×3 mL) and dried over MgSO4. The filtered solution was concentrated to dryness. The residue was dissolved in acetonitrile (10 mL) and anhydrous butyl nitrite and copper (II) bromide were introduced under nitrogen. The mixture was stirred at 65° C. for 2 hrs and cooled to rt. The reaction was concentrated and purified by silica gel column chromatography eluting with hexane/ethyl acetate (9/1) yielding 1-(3-bromo-4-chloro-benzenesulfonyl)-2,3,4,5-tetrahydro-1H-1-benzazepine as a white solid in 82% yield (0.56 g). MS: 402 (M+H)+; $t_R$=3.17 min (method 1).

The following intermediate compounds were similarly prepared using this procedure:

3-Bromo-4-chloro-N-(2-methoxy-phenyl)-N-methyl-benzenesulfonamide, MS: 392 (M+H)+; $t_R$=2.99 min (method 1);

1-(3-Bromo-4-chloro-benzenesulfonyl)-1,2,3,4-tetrahydro-quinoline, MS: 388 (M+H)+; $t_R$=3.11 min (method 1);

4-(3-Bromo-4-chloro-benzenesulfonyl)-3,4-dihydro-2H-benzo[1,4]oxazine, MS: 390 (M+H)+; $t_R$=3.03 min (method 1);

1-(3-Bromo-4-chloro-benzenesulfonyl)-4,4-dimethyl-1,2,3,4-tetrahydro-quinoline, MS: 416 (M+H)+; $t_R$=2.76 min (method 1);

1-(3-Bromo-4-chloro-benzenesulfonyl)-2-methyl-1,2,3,4-tetrahydro-quinoline, MS: 402 (M+H)+; $t_R$=2.72 min (method 1);

1-(3-Bromo-4-chloro-benzenesulfonyl)-1,2,3,5-tetrahydro-benzo[e][1,4]oxazepine, MS: 404 (M+H)+; $t_R$=2.49 min (method 1);

1-(3-Bromo-4-chloro-benzenesulfonyl)-8-methyl-1,2,3,4-tetrahydro-quinoline, MS: 402 (M+H)+; $t_R$=2.71 min (method 1);

1-(3-Bromo-4-chloro-benzenesulfonyl)-1,2,3,4-tetrahydro-benzo[b]azepin-5-one, MS: 416 (M+H)+; $t_R$=2.44 min (method 1);

1-(3-Bromo-4-methyl-benzenesulfonyl)-2,3,4,5-tetrahydro-1H-benzo[b]azepine, MS: 382 (M+H)+; $t_R$=3.15 min (method 1);

9-(3-Bromo-4-chloro-benzenesulfonyl)-1-methyl-6,7,8,9-tetrahydro-5-oxa-9-aza-benzocycloheptene, $t_R$=6.15 min (method 5), 1H NMR: (CDCl3), δ, 7.866 (1H, s), 7.482 (2H, s), 7.186 (1H, t), 7.079 (1H, d, J=7.2 Hz), 6.843 (1H, d, J=10.8 Hz), 4.376-4.437 (1H, m), 4.048-4.101 (1H, m), 3.337-3.422 (1H, m), 3.071-3.170 (1H, m), 2.488 (3H, s), 1.913-2.042 (1H, m), 1.486-1.574 (1H, m); and 9-(3-Bromo-4-chloro-benzenesulfonyl)-6,7,8,9-tetrahydro-5-oxa-9-aza-benzocycloheptene, MS: 401 (M+H)+; $t_R$=9.65 min (method 6).

Step 4C: 1-[4-Chloro-3-(4,4,5,5-tetramethyl-1,3,2-dioxaborolan-2-yl)-benzenesulfonyl]-2,3,4,5-tetrahydro-1H-1-benzazepine To 1-(3-bromo-4-chloro-benzenesulfonyl)-2,3,4,5-tetrahydro-1H-1-benzazepine (0.43 g, 1.1 mmol) in dioxane (5 mL), was added bis(pinacolato)diboron (0.41 g, 1.63 mmol), potassium acetate (0.32 g, 3.3 mmol) and Pd(dppf)2Cl2 (0.064 g, 0.09 mmol). Nitrogen was bubbled into the mixture for 10 min and the mixture was heated at 100° C. under a stream of N2 for 12 hrs. The mixture was cooled to rt, filtered through a silica gel pad, and then concentrated. Purification of the resulting oil by silica gel column chromatography (eluting with hexanes/ethyl acetate, 4/1) yielded 1-[4-chloro-3-(4,4,5,5-tetramethyl-1,3,2-dioxaborolan-2-yl)-benzenesulfonyl]-2,3,4,5-tetrahydro-1H-1-benzazepine (0.37 g, 75% yield). MS: 366.0 (M+H)+; $t_R$=2.80 min (method 1).

The following intermediate compounds were similarly prepared using this procedure resulting in the boronic ester or boronic acid:

4-Chloro-N-(2-methoxy-phenyl)-N-methyl-3-(4,4,5,5-tetramethyl-[1,3,2]dioxaborolan-2-yl)-benzenesulfonamide, MS: 438 (M+H)+; $t_R$=3.12 min (method 1);

1-[4-Chloro-3-(4,4,5,5-tetramethyl-[1,3,2]dioxaborolan-2-yl)-benzenesulfonyl]-1,2,3,4-tetrahydro-quinoline, MS: 434 (M+H)+; $t_R$=3.23 min (method 1);

2-Chloro-5-[(3,4-dihydro-2H-benzo[1,4]oxazin-4-yl)sulfonyl]-phenylboronic acid, MS: 354 (M+H)+; $t_R$=2.14 min (method 1);

1-[4-Chloro-3-(4,4,5,5-tetramethyl-[1,3,2]dioxaborolan-2-yl)-benzenesulfonyl]-4,4-dimethyl-1,2,3,4-tetrahydro-quinoline, MS: 462 (M+H)+; $t_R$=2.83 min (method 1);

2-Chloro-5-[(2-methyl-1,2,3,4-tetrahydro-quinolin-1-yl)sulfonyl]-phenylboronic acid, MS: 366 (M+H)+; $t_R$=2.26 min (method 1);

1-[4-Chloro-3-(4,4,5,5-tetramethyl-[1,3,2]dioxaborolan-2-yl)-benzenesulfonyl]-1,2,3,5-tetrahydro-benzo[e][1,4]oxazepine, MS: 450 (M+H)$^+$; $t_R$=2.62 min (method 1);

1-[4-Chloro-3-(4,4,5,5-tetramethyl-[1,3,2]dioxaborolan-2-yl)-benzenesulfonyl]-8-methyl-1,2,3,4-tetrahydro-quinoline, MS: 448 (M+H)$^+$; $t_R$=2.79 min (method 1);

2-Chloro-5-[(1,2,3,4-tetrahydro-benzo[b]azepin-5-one-1-yl)sulfonyl]-phenylboronic acid, MS: 380 (M+H)$^+$; $t_R$=1.99 min (method 1);

9-[4-Chloro-3-(4,4,5,5-tetramethyl-[1,3,2]dioxaborolan-2-yl)-benzenesulfonyl]-1-methyl-6,7,8,9-tetrahydro-5-oxa-9-aza-benzocycloheptene, MS: 464 (M+H)$^+$; $t_R$=2.68 min (method 1); and 9-[4-Chloro-3-(4,4,5,5-tetramethyl-[1,3,2]dioxaborolan-2-yl)-benzenesulfonyl]-6,7,8,9-tetrahydro-5-oxa-9-aza-benzocycloheptene, MS: 323 [M-BO$_2$C$_6$H$_{12}$]$^+$; $t_R$=8.74 min (method 6).

Step 4D: 1-[4-Chloro-3-(6-chloro-4-methyl-pyridin-3-yl)-benzenesulfonyl]-2,3,4,5-tetrahydro-1H-1-benzazepine A mixture of 1-[4-chloro-3-(4,4,5,5-tetramethyl-1,3,2-dioxaborolan-2-yl)-benzenesulfonyl]-2,3,4,5-tetrahydro-1H-1-benzazepine (67 mg, 0.18 mmol), 5-bromo-2-chloro-4-picoline (45 mg, 0.22 mmol), Pd(PPh$_3$)$_4$ (11 mg, 0.01 mmol), K$_2$CO$_3$ (130 mg, 0.93 mmol) in 1,4-Dioxane (1 mL), was heated at 100° C. for 12 hrs. This mixture was cooled to rt and the solvent evaporated. The residue was purified by silica gel column chromatography eluted with (Hexanes/Ethyl acetate, 9/1) to yield 1-[4-chloro-3-(6-chloro-4-methyl-pyridin-3-yl)-benzenesulfonyl]-2,3,4,5-tetrahydro-1H-1-benzazepine 4-1 (0.019 g, 23% yield). MS: 447 (M+H)$^+$; $t_R$=9.94 min (method 2).

The following compounds were similarly prepared using this procedure:

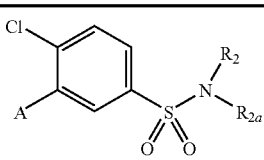

| Ex. | A | NR$_2$R$_{2a}$ | MS (M+H)$^+$ | $t_R$ (min) | HPLC Method |
|---|---|---|---|---|---|
| 4-1 | 6-chloro-4-methyl-pyridin-3-yl | 2,3,4,5-tetrahydro-1H-benzo[b]azepin-1-yl | 447 | 9.94 | 2 |
| 4-2 | 6-chloro-4-methyl-pyridin-3-yl | 1,2,3,4-tetrahydro-benzo[b]azepin-5-one-1-yl | 461 | 5.64 | 4 |
| 4-3 | 6-chloro-4-methyl-pyridin-3-yl | 1,2,3,4-tetrahydro-quinolin-1-yl | 433 | 9.31 | 2 |
| 4-4 | 6-chloro-4-methyl-pyridin-3-yl | 3,4-dihydro-2H-benzo[1,4]oxazin-4-yl | 435 | 9.32 | 2 |
| 4-5 | 6-chloro-4-methyl-pyridin-3-yl | 4,4-dimethyl-1,2,3,4-tetrahydro-quinolin-1-yl | 461 | 10.36 | 2 |
| 4-6 | 6-chloro-4-methyl-pyridin-3-yl | 2-methyl-1,2,3,4-tetrahydro-quinolin-1-yl | 447 | 10.00 | 2 |
| 4-7 | 6-chloro-4-methyl-pyridin-3-yl | 8-methyl-1,2,3,4-tetrahydro-quinolin-1-yl | 447 | 6.38 | 4 |
| 4-8 | 4-chloro-6-methyl-pyridin-3-yl | 1,2,3,4-tetrahydro-quinolin-1-yl | 433 | 8.18 | 2 |
| 4-9 | 4-methyl-6-trifluoro-methyl-pyridin-3-yl | 2,3,4,5-tetrahydro-1H-benzo[b]azepin-1-yl | 481 | 10.10 | 2 |
| 4-10 | 4-methyl-6-trifluoro-methyl-pyridin-3-yl | 1,2,3,4-tetrahydro-quinolin-1-yl | 467 | 6.30 | 4 |
| 4-11 | 4-methyl-6-trifluoro-methyl-pyridin-3-yl | 3,4-dihydro-2H-benzo[1,4]oxazin-4-yl | 469 | 5.84 | 4 |
| 4-12 | 4-methyl-6-trifluoro-methyl-pyridin-3-yl | 4,4-dimethyl-1,2,3,4-tetrahydro-quinolin-1-yl | 495 | 6.58 | 4 |
| 4-13 | 4-cyano-6-trifluoro-methyl-pyridin-3-yl | 2,3,4,5-tetrahydro-1H-benzo[b]azepin-1-yl | 509 (M+NH$_4$)$^+$ | 6.40 | 4 |
| 4-14 | 4-cyano-6-trifluoro-methyl-pyridin-3-yl | 8-methyl-1,2,3,4-tetrahydro-quinolin-1-yl | 509 (M+NH$_4$)$^+$ | 6.44 | 4 |
| 4-15 | 4-cyano-6-trifluoro-methyl-pyridin-3-yl | 3,4-dihydro-2H-benzo[1,4]oxazin-4-yl | 480 | 9.48 | 2 |
| 4-16 | 4-cyano-6-trifluoro-methyl-pyridin-3-yl | 4,4-dimethyl-1,2,3,4-tetrahydro-quinolin-1-yl | 506 | 10.33 | 2 |
| 4-17 | 4-cyano-6-trifluoro-methyl-pyridin-3-yl | 1,2,3,5-tetrahydro-benzo[e][1,4]oxazepin-1-yl | 494 | 5.86 | 4 |
| 4-18 | 3-cyano-quinolin-2-yl | 2,3,4,5-tetrahydro-1H-benzo[b]azepin-1-yl | 474 | 9.49 | 2 |
| 4-19 | 3-cyano-quinolin-2-yl | 4,4-dimethyl-1,2,3,4-tetrahydro-quinolin-1-yl | 488 | 6.40 | 4 |
| 4-20 | 4-cyano-6-trifluoro-methyl-pyridin-3-yl | 1-methyl-6,7,8,9-tetrahydro-5-oxa-9-aza-benzocyclohepten-9-yl | 508.0 | 10.55 | 2 |
| 4-21 | 4-methyl-6-trifluoro-methyl-pyridin-3-yl | 1-methyl-6,7,8,9-tetrahydro-5-oxa-9-aza-benzocyclohepten-9-yl | 496.8 | 6.28 | 2 |
| 4-22 | 6-cyano-4-methyl-pyridin-3-yl | 1-methyl-6,7,8,9-tetrahydro-5-oxa-9-aza-benzocyclohepten-9-yl | 453.8 | 5.80 | 2 |
| 4-23 | 6-chloro-4-methyl-pyridin-3-yl | 6,7,8,9-tetrahydro-5-oxa-9-aza-benzocyclohepten-9-yl | 448.8 | 9.05 | 2 |
| 4-24 | 4-cyano-6-trifluoro-methyl-pyridin-3-yl | 6,7,8,9-tetrahydro-5-oxa-9-aza-benzocyclohepten-9-yl | 494.0 | 9.29 | 2 |

47

Example 4-17 was further characterized by ¹H N.M.R: (CDCl₃), δ, 8.79 (1H, s), 8.03 (1H, s), 7.89-7.66 (3H, m), 7.40-7.22 (4H, m), 4.35 (2H, br, s), 3.89 (2H, br, s), 1.57 (2H, br, s).

Example 5

1-[4-Chloro-3-(4,6-dichloro-pyridin-3-yl)-benzene-sulfonyl]-2,3,4,5-tetrahydro-1H-1-benzazepine

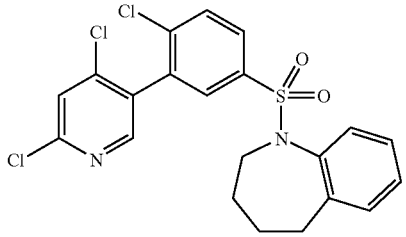

Step 5A: 1-[4-Chloro-3-(4,6-dichloro-pyridin-3-yl)-benzenesulfonyl]-2,3,4,5-tetrahydro-1H-1-benzazepine To a suspension of 1-(3-bromo-4-chloro-benzenesulfonyl)-2,3,4,5-tetrahydro-1H-1-benzazepine, 2,4-dichloropyridine-5-boronic acid hydrate, tri-t-butylphosphonium tetrafluoroborate and tris(dibenzylideneacetone)dipalladium(0) in THF (0.73 mL) was added potassium hydroxide aqueous solution (0.05 g in 0.18 mL water). The suspension was bubbled with N₂ for 5 min and then heated at 50° C. for 12 hrs. This mixture was cooled to it and concentrated. The residue was purified by silica gel column chromatography eluting with (hexanes/ethyl acetate, 20/1) to yield 1-[4-chloro-3-(4,6-dichloro-pyridin-3-yl)-benzenesulfonyl]-2,3,4,5-tetrahydro-1H-1-benzazepine 5-1 (9 mg, 8.7% yield). MS: 467 (M+H)⁺; $t_R$=9.95 min (method 2).

The following example compounds were prepared using this procedure.

| Ex. | —NR₂R₂ₐ | MS (M + H)⁺ | $t_R$ (min) method 2 |
|---|---|---|---|
| 5-1 | 2,3,4,5-tetrahydro-1H-benzo[b]azepin-1-yl | 467 | 9.95 |
| 5-2 | N-(2-methoxy-phenyl)-methylamino | 457 | 9.14 |
| 5-3 | 1,2,3,4-tetrahydro-quinolin-1-yl | 453 | 9.71 |
| 5-4 | 3,4-dihydro-2H-benzo[1,4]oxazin-4-yl | 455 | 9.33 |
| 5-5 | 4,4-dimethyl-1,2,3,4-tetrahydro-quinolin-1-yl | 481 | 10.77 |
| 5-6 | 2-methyl-1,2,3,4-tetrahydro-quinolin-1-yl | 467 | 10.41 |
| 5-7 | 2,3,4,5-tetrahydro-1H-benzo[b]azepin-1-yl | 447 | 9.64 |

48

Example 6

4-[5-Chloro-4-(4-cyano-6-trifluoromethyl-pyridin-3-yl)-2-(2,3,4,5-tetrahydro-benzo[b]azepine-1-sulfonyl)-phenoxy]-butyric acid tert-butyl ester

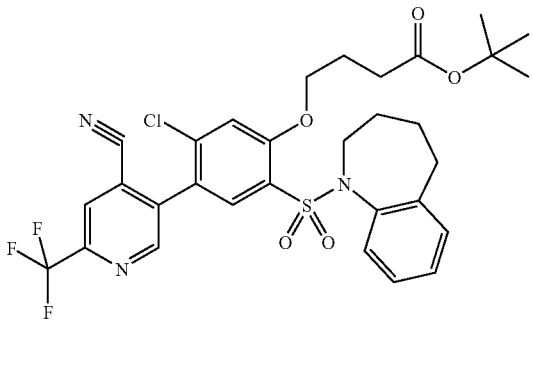

Step 6A: 1-(5-Bromo-4-chloro-2-fluoro-benzenesulfonyl)-2,3,4,5-tetrahydro-1H-benzo[b]azepine To a solution of DCM (20 mL) containing 5-bromo-4-chloro-2-fluoro-benzenesulfonyl chloride (2.82 g, 9.2 mmol) was added 2,3,4,5-tetrahydro-1H-benzo[b]azepine (1.35 g, 9.2 mmol) and triethylamine (2.8 mL, 21 mmol). The mixture was stirred for 16 hrs. The mixture was then diluted with 50 mL of DCM and repartioned with 50 mL of water. The organic layer was further washed with water (2×30 mL) and dried over MgSO₄. Concentration and purification by silica gel column chromatography eluting with hexane/ethyl acetate (9/1 to 6/1) yielded 1-(5-bromo-4-chloro-2-fluoro-benzenesulfonyl)-2,3,4,5-tetrahydro-1H-benzo[b]azepine as the pale yellow solid (2.70 g). NMR (CDCl₃), δ, 8.059 (1H, d, J=7.2 Hz), 7.404 (1H, d, J=9.3 Hz), 7.202-7.218 (2H, q), 7.073-7.129 (1H, m), 7.860 (1H, d, J=7.8 Hz), 3.746 (2H, m), 2.750-2.813 (2H, m), 1.906-1.982 (2H, m), 1.639-1.678 (2H, m).

Step 6B: 1-(5-Bromo-4-chloro-2-methoxy-benzenesulfonyl)-2,3,4,5-tetrahydro-1H-benzo[b]azepine To a solution of DCM (8 mL) containing 1-(5-bromo-4-chloro-2-fluoro-benzenesulfonyl)-2,3,4,5-tetrahydro-1H-benzo[b]azepine (2.35 g, 5.6 mmol) was added 25% sodium methoxide in methanol (7.5 mL). The resulting suspension was stirred at rt for 3 hrs, followed by repartitioning with DCM (45 mL) and water (50 mL). A 6 N HCl solution was added dropwise until the aqueous layer pH was 7. The organic layer was separated, washed with water (2×30 mL), dried over MgSO₄, and evaporated to afford 1-(5-bromo-4-chloro-2-methoxy-benzenesulfonyl)-2,3,4,5-tetrahydro-1H-benzo[b]azepine as the pale yellow foam (2.38 g). MS: 430.0 (M+H)⁺; $t_R$=6.21 min (method 4). NMR (CDCl₃), δ, 8.070 (1H, s), 7.130-7.219 (3H, m), 7.025-7.082 (1H, m), 6.761 (1H, d, J=7.5 Hz), 3.868 (3H, s), 3.733 (2H, m), 2.808-2.845 (2H, m), 1.902-1.940 (2H, m), 1.568-1.667 (2H, m).

Step 6C: 4-Bromo-5-chloro-2-(2,3,4,5-tetrahydro-benzo[b]azepine-1-sulfonyl)-phenol To a solution of DCM (25.0 mL) containing 1-(5-bromo-4-chloro-2-methoxy-benzenesulfonyl)-2,3,4,5-tetrahydro-1H-benzo[b]azepine (2.15 g, 5 mmol) at −78° C. was added BBr₃ (12.5 mL, 1M in DCM, 12.5 mmol) dropwise. The mixture was gradually warmed to rt while it was stirred for 4 hrs. The mixture was concentrated and partitioned between ethyl acetate (100 mL) and sat. NaHCO$_3$ solution (100 mL). The organic layer was further washed with brine (2×50 mL), dried over MgSO$_4$, and evaporated. The purification of the crude material by silica gel column chromatography eluting with hexane/ethyl acetate (6/1) yielded 4-bromo-5-chloro-2-(2,3,4,5-tetrahydro-benzo[b]azepine-1-sulfonyl)-phenol as a white solid (1.9 g). NMR (CDCl$_3$), δ, 7.739 (1H, s), 7.186-7.259 (4H, m), 7.127 (1H, s), 3.692 (2H, m), 2.502-2.539 (2H, m), 1.802-1.868 (2H, m), 1.601-1.676 (2H, m).

Step 6D: 4-[4-Bromo-5-chloro-2-(2,3,4,5-tetrahydro-benzo[b]azepine-1-sulfonyl)-phenoxy]-butyric acid tert-butyl ester To 4-bromo-5-chloro-2-(2,3,4,5-tetrahydro-benzo[b]azepine-1-sulfonyl)-phenol (0.83 g, 2 mmol) in dry DMF (8 mL), was added K$_2$CO$_3$ (0.69 g, 5 mmol), followed by the addition of t-butyl 4-bromobutyrate (0.58 g, 2.6 mmol). The mixture was heated at 62° C. for 15 hrs and partitioned between ethyl acetate (50 mL) and water (25 mL). The organic layer was separated, washed with brine (2×25 mL), and dried over MgSO$_4$. After filtration, the solution was concentrated and purified by silica gel column chromatography eluting with ethyl acetate in hexanes (1/8) yielding 4-[4-bromo-5-chloro-2-(2,3,4,5-tetrahydro-benzo[b]azepine-1-sulfonyl)-phenoxy]-butyric acid tert-butyl ester as a pale yellow foam (1.05 g). MS: 501.8 (M+H-tBu)$^+$; t$_R$=11.2 min (method 2). NMR (CDCl$_3$), δ, 8.060 (1H, s), 7.133-7.205 (3H, m), 7.011-7.067 (1H, m), 6.789 (1H, d, J=8.1 Hz), 4.086 (2H, t), 3.742 (2H, t), 2.826 (2H, m), 2.346 (2H, t), 1.827-1.959 (4H, m), 1.617-1.641 (2H, m), 1.431 (9H, s).

Step 6E: 4-[5-Chloro-2-2,3,4,5-tetrahydro-benzo[b]azepine-1-sulfonyl)-4-(4,4,5,5-tetramethyl-[1,3]-dioxolan-2-yl)-phenoxy]-butyric acid tert-butyl ester A mixture of 4-[4-bromo-5-chloro-2-(2,3,4,5-tetrahydro-benzo[b]azepine-1-sulfonyl)-phenoxy]-butyric acid tert-butyl ester (0.78 g, 1.4 mmol), bis(pinacolato)diboron (0.46 g, 1.8 mmol), PdCl$_2$(dppf)$_2$ (51 mg, 0.07 mmol), and potassium acetate (0.41 g, 4.2 mmol) in dioxane (7 mL) was degassed with N$_2$ for 5 min. The reaction vessel was sealed and heated at 90° C. for 15 hrs. The mixture was filtered through Celite to remove solids. The Celite was washed with ethyl acetate several times. The combined solution was washed with water and brine, and was dried over MgSO$_4$. After filtration and concentration, the crude material was purified by silica gel column chromatography eluting with ethyl acetate in hexanes (1/9 to 2/3) to yield 4-[5-chloro-2-(2,3,4,5-tetrahydro-benzo[b]azepine-1-sulfonyl)-4-(4,4,5,5-tetramethyl-[1,3]dioxolan-2-yl)-phenoxy]-butyric acid tert-butyl ester (0.47 g). MS: 550.0 (M+H-tBu)$^+$; t$_R$=11.756 min (method 2).

Step 6F: 4-[5-Chloro-4-(4-cyano-6-trifluoromethyl-pyridin-3-yl)-2-(2,3,4,5-tetrahydro-benzo[b]azepine-1-sulfonyl)-phenoxy]-butyric acid tert-butyl ester 4-[5-Chloro-2-(2,3,4,5-tetrahydro-benzo[b]azepine-1-sulfonyl)-4-(4,4,5,5-tetramethyl-[1,3]dioxolan-2-yl)-phenoxy]-butyric acid tert-butyl ester (60.0 mg, 0.1 mmol), 5-bromo-2-trifluoromethyl-isonicotinonitrile (23 mg, 0.09 mmol), Pd(Ph$_3$P)$_4$ (12 mg, 0.01 mmol) and K$_2$CO$_3$ (56 mg, 0.4 mmol) in a mixture of dioxane (1.5 mL) and water (0.15 mL) was degassed with N$_2$ for 5 min. The reaction vessel was sealed and heated at 100° C. for 16 hrs. Ethyl acetate (5 mL) and water (5 mL) were added. The organic layer was separated, washed with brine (2×5 mL), dried over MgSO$_4$, filtered, concentrated and purified by TLC plates eluting with ethyl acetate in hexanes (1/3) to give 4-[5-chloro-4-(4-cyano-6-trifluoromethyl-pyridin-3-yl)-2-(2,3,4,5-tetrahydro-benzo[b]azepine-1-sulfonyl)-phenoxy]-butyric acid tert-butyl ester 6-1 as a white foam (50 mg). MS: 593.9 (M+H-tBu)$^+$; t$_R$=6.98 min (method 4). NMR (CDCl$_3$), δ, 8.791 (1H, s), 7.738-8.101 (2H, m), 7.060-7.272 (4H, m), 6.774-6.828 (1H, m), 4.213 (2H, m), 3.780 (2H, m), 2.833 (2H, m), 2.404 (2H, t), 1.912-2.029 (4H, m), 1.591-1.657 (2H, m), 1.448 (9H, s).

The following example compounds were prepared using this procedure.

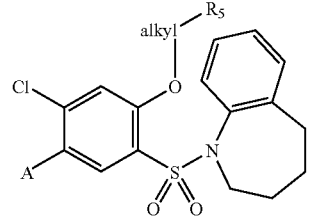

| Ex. | A | -alkyl-R$_5$ | MS (M + H)$^+$ | t$_R$ (min) | HPLC Method |
|---|---|---|---|---|---|
| 6-1 | 4-Cyano-6-trifluoromethyl-pyridin-3-yl | 4-butyric acid tert-butyl ester | 593.9 (M + H-tBu)$^+$ | 6.98 | 4 |
| 6-2 | 4-Methyl-6-trifluoromethyl-pyridin-3-yl | 4-butyric acid tert-butyl ester | 639.2 | 6.92 | 5 |
| 6-3 | 6-Cyano-4-methyl-pyridin-3-yl | 4-butyric acid tert-butyl ester | 596.2 | 2.78 | 1 |
| 6-4 | 3-Cyano-quinolin-2-yl | 4-butyric acid tert-butyl ester | 576.1 (M + H-tBu)$^+$ | 6.77 | 5 |
| 6-5 | 4-Cyano-6-trifluoromethyl-pyridin-3-yl | acetic acid tert-butyl ester | 639.0 | 6.78 | 5 |

Example 7

4-[5-Chloro-4-(4-cyano-6-trifluoromethyl-pyridin-3-yl)-2-(2,3,4,5-tetrahydro-benzo[b]azepine-1-sulfonyl)-phenoxy]-butyric acid

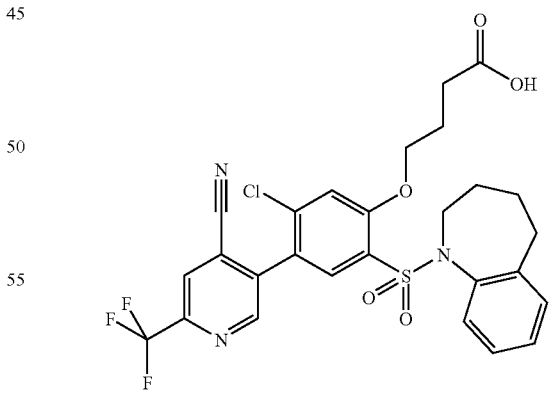

Step 7A: 4-[5-Chloro-4-(4-cyano-6-trifluoromethyl-pyridin-3-yl)-2-(2,3,4,5-tetrahydro-benzo[b]azepine-1-sulfonyl)-phenoxy]-butyric acid 4-[5-Chloro-4-(4-cyano-6-trifluoromethyl-pyridin-3-yl)-2-(2,3,4,5-tetrahydro-benzo[b]azepine-1-sulfonyl)-phenoxy]-butyric acid tert-butyl ester 6-1 (30 mg, 0.046 mmol) was stirred in 4M HCl in dioxane (1 mL) at 40° C. for 2 hrs and concentrated. The resulting oil residue was purified by TLC plates eluting with 4% methanol in DCM to afford 4-[5-chloro-4-(4-cyano-6-trifluoromethyl-pyridin-3-yl)-2-(2,3,4,5-tetrahydro-benzo[b]azepine-1-sulfonyl)-phenoxy]-butyric acid 7-1. MS: 593.8 (M+H)$^+$; $t_R$=8.94 min (method 2).

The following example compounds were prepared using this procedure.

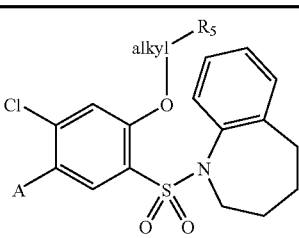

| Ex. | A | -alkyl-R$_5$ | MS (M + H)$^+$ | $t_R$ (min) | HPLC Method |
|---|---|---|---|---|---|
| 7-1 | 4-Cyano-6-trifluoromethyl-pyridin-3-yl | 4-butyric acid | 593.8 | 8.94 | 2 |
| 7-2 | 4-Methyl-6-trifluoromethyl-pyridin-3-yl | 4-butyric acid | 583.4 | 5.79 | 3 |
| 7-3 | 6-Cyano-4-methyl-pyridin-3-yl | 4-butyric acid | 539.7 | 4.72 | 4 |
| 7-4 | 3-Cyano-quinolin-2-yl | 4-butyric acid | 576.0 | 5.52 | 3 |
| 7-5 | 4-Cyano-6-trifluoromethyl-pyridin-3-yl | acetic acid | 565.9 | 5.11 | 5 |

Example 8

5-[2-Chloro-4-hydroxy-5-(2,3,4,5-tetrahydro-benzo[b]azepine-1-sulfonyl)-phenyl]-4-methyl-pyridine-2-carbonitrile

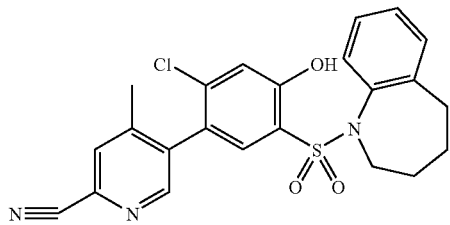

Step 8A: 5-chloro-2-(2,3,4,5-tetrahydro-benzo[b]azepine-1-sulfonyl)-4-(4,4,5,5-tetramethyl-[1,3]-dioxolan-2-yl)-phenol A mixture of 4-bromo-5-chloro-2-(2,3,4,5-tetrahydro-benzo[b]azepine-1-sulfonyl)-phenol (1.0 g, 2.4 mmol, step 6C), bis(pinacolato)diboron (0.76 g, 7.2 mmol), PdCl$_2$(dppf)$_2$ (0.12 g, 0.16 mmol) and potassium acetate (0.71 g, 4.2 mmol) in dioxane (13 mL) was degassed with N$_2$ for 5 min, and the reaction vessel was sealed and heated at 90° C. for 15 hrs. The Celite was filtered through Celite to remove solids. The Celite was washed by ethyl acetate several times. The combined organics were washed with water and brine and were dried over MgSO$_4$. After filtration and concentration, the material was purified by silica gel column chromatography eluting with ethyl acetate in hexanes (1/11 to 1/4) to yield 5-chloro-2-(2,3,4,5-tetrahydro-benzo[b]azepine-1-sulfonyl)-4-(4,4,5,5-tetramethyl-[1,3]dioxolan-2-yl)-phenol as a white foam (0.80 g). MS: 463.7 (M+H)$^+$; $t_R$=2.62 min (method 1).

Step 8B: 5-[2-chloro-4-hydroxy-benzo[b]azepine-1-sulfonyl)-phenyl]-4-methyl-pyridine-2-carbonitrile 5-Chloro-2-(2,3,4,5-tetrahydro-benzo[b]azepine-1-sulfonyl)-4-(4,4,5,5-tetramethyl-[1,3]dioxolan-2-yl)-phenol (153.0 mg, 0.33 mmol), 5-bromo-4-methyl-pyridine-2-carbonitrile (60 mg, 0.30 mmol), Pd(Ph$_3$P)$_4$ (38 mg, 0.03 mmol) and K$_2$CO$_3$ (138 mg, 1.0 mmol) in a mixture of dioxane (4 mL) and water (0.4 mL) was degassed with N$_2$ for 5 min. The reaction vessel was sealed and then heated at 100° C. for 16 hrs. The mixture was then partitioned between ethyl acetate (20 mL) and water (10 mL). The organic layer was washed with brine (2×10 mL) and dried over MgSO$_4$. After filtration and concentration, the material was purified by TLC plates eluting with ethyl acetate in hexanes (1/3) to give 5-[2-chloro-4-hydroxy-5-(2,3,4,5-tetrahydro-benzo[b]azepine-1-sulfonyl)-phenyl]-4-methyl-pyridine-2-carbonitrile 8-1 as a white solid (100 mg). MS: 453.9 (M+H)$^+$; $t_R$=8.37 min (method 2).

The following example compounds were prepared using this procedure.

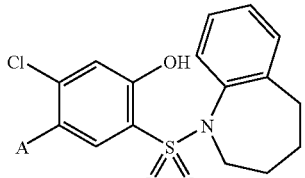

| Ex. | A | MS (M + H)$^+$ | $t_R$ (min) | HPLC Method |
|---|---|---|---|---|
| 8-1 | 6-cyano-4-methyl-pyridin-3-yl | 453.9 | 8.37 | 2 |
| 8-2 | 4-Cyano-6-trifluoromethyl-pyridin-3-yl | 508.0 | 6.09 | 4 |
| 8-3 | 3-Cyano-quinolin-2-yl | 490.1 | 5.82 | 4 |

Example 9

3-[5-Chloro-4-(6-cyano-4-methyl-pyridin-3-yl)-2-(2,3,4,5-tetrahydro-benzo[b]azepine-1-sulfonyl)-phenoxy]-propionic acid

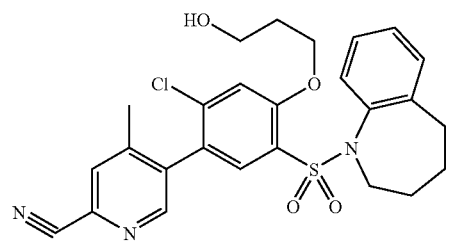

Step 9A: 5-[2-Chloro-4-(3-hydroxy-propoxy)-5-(2,3,4,5-tetrahydro-benzo[b]azepine-1-sulfonyl)-phenyl]-4-methyl-pyridine-2-carbonitrile To 5-[2-chloro-4-hydroxy-5-(2,3,4,5-tetrahydro-benzo[b]azepine-1-sulfonyl)-phenyl]-4-methyl-pyridine-2-carbonitrile (90 mg, 0.2 mmol) in dry acetonitrile (1.5 mL), was added $Cs_2CO_3$ (130 mg, 0.4 mmol), followed by an addition of 3-bromo-1-propanol (36 mg, 0.26 mmol). The mixture was heated at 45° C. for 24 hrs and partitioned between ethyl acetate (10 mL) and water (5 mL). The organic layer was separated, washed with brine (2×5 mL) and dried over $MgSO_4$. After filtration, the mixture was concentrated and purified by TLC plates eluting with ethyl acetate in hexanes (1/1) to give 5-[2-chloro-4-(3-hydroxy-propoxy)-5-(2,3,4,5-tetrahydro-benzo[b]azepine-1-sulfonyl)-phenyl]-4-methyl-pyridine-2-carbonitrile 9-1 as a white solid (62 mg). MS: 511.9 (M+H)$^+$; $t_R$=8.07 min (method 2). NMR (CDCl$_3$), δ, 8.344 (1H, s), 7.634 (1H, s), 7.597 (1H, s), 7.235 (1H, s), 7.164-7.184 (2H, m), 7.008-7.060 (1H, m), 6.871 (1H, d, J=7.8 Hz), 4.287 (2H, t), 3.769-3.805 (4H, m), 2.775-2.786 (2H, m), 2.064 (3H, s), 1.850-1.905 (2H, m), 1.959-1.995 (2H, m), 1.653 (2H, s).

Similarly, 5-[2-Chloro-4-(3-hydroxy-propoxy)-5-(2,3,4,5-tetrahydro-benzo[b]azepine-1-sulfonyl)-phenyl]-2-trifluoromethyl-isonicotinonitrile 9-2 was prepared. MS: 565.8 (M+H)$^+$; $t_R$=8.86 min (method 2)

Example 10

3-[5-Chloro-4-(6-cyano-4-methyl-pyridin-3-yl)-2-(2,3,4,5-tetrahydro-benzo[b]azepine-1-sulfonyl)-phenoxy]-propionic acid

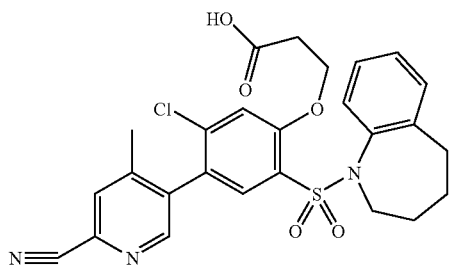

Step 10A. 3-[5-Chloro-4-(6-cyano-4-methyl-pyridin-3-yl)-2-(2,3,4,5-tetrahydro-benzo[b]azepine-1-sulfonyl)-phenoxy]-propionic acid To 5-[2-chloro-4-(3-hydroxy-propoxy)-5-(2,3,4,5-tetrahydro-benzo[b]azepine-1-sulfonyl)-phenyl]-4-methyl-pyridine-2-carbonitrile 8-1 (31 mg, 0.06 mmol) in a mixture of DCM (0.3 mL), acetonitrile (0.3 mL) and water (0.4 mL) was added $NaIO_4$ (38 mg, 0.18 mmol) and $RuCl_3$ (2.5 mg, 0.012 mmol). The mixture was stirred at rt for 40 minutes, then 1 mL of methanol was added. The mixture was filtered and purified by prep. LCMS to afford 3-[5-chloro-4-(6-cyano-4-methyl-pyridin-3-yl)-2-(2,3,4,5-tetrahydro-benzo[b]azepine-1-sulfonyl)-phenoxy]-propionic acid 10-1. MS: 526.0 (M+H)$^+$; $t_R$=4.65 min (method 4). NMR (CDCl$_3$), δ, 8.378 (1H, s), 7.649 (1H, s), 7.621 (1H, s), 7.259 (1H, s), 7.136-7.203 (2H, m), 6.981-7.038 (1H, m), 6.746 (1H, d, J=7.8 Hz), 4.423 (2H, t), 3.728 (2H, m), 2.803-2.842 (4H, m), 2.162 (3H, s), 1.894-1.929 (2H, m), 1.658 (2H, m).

Similarly, 3-[5-chloro-4-(4-cyano-6-trifluoromethyl-pyridin-3-yl)-2-(2,3,4,5-tetrahydro-benzo[b]azepine-1-sulfonyl)-phenoxy]-propionic acid 10-2 was prepared. MS: 579.9 (M+H)$^+$; $t_R$=5.16 min (method 4).

Example 11

5-[2-Chloro-5-(4,4-dimethyl-3,4-dihydro-2H-quinoline-1-sulfonyl)-4-(4-hydroxy-butoxy)-phenyl]-2-trifluoromethyl-isonicotinonitrile

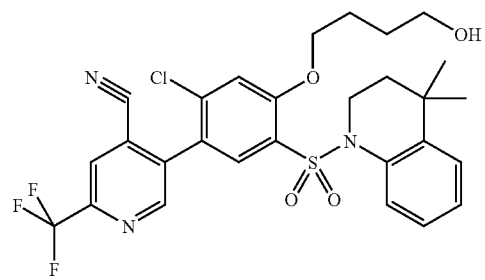

Step 11A: 1-(5-Bromo-4-chloro-2-fluoro-benzenesulfonyl)-4,4-dimethyl-1,2,3,4-tetrahydro-quinoline To 5-bromo-4-chloro-2-fluorobenzenesulfonyl chloride (3.15 g, 10.8 mmol) in dry DCM (40 mL), was added 4,4-dimethyl-1,2,3,4-tetrahydro-quinoline (1.50 g, 9.3 mmol) and triethylamine (2.15 mL, 15.5 mmol). The mixture was stirred at ambient temperature for 16 hrs. Additional sulfonyl chloride (0.93 g, 3.2 mmole) was added and the mixture was stirred an additional 72 hrs. The mixture was washed with 1N hydrochloric acid solution, saturated sodium bicarbonate solution and brine. The organic layer was dried over $MgSO_4$ and the filtrate evaporated. The residue was purified by silica gel chromatography [eluent: 5% ethyl acetate in hexane] to give 1-(5-bromo-4-chloro-2-fluoro-benzenesulfonyl)-4,4-dimethyl-1,2,3,4-tetrahydro-quinoline as a yellow solid (3.6 g). $t_R$=2.82 min (method 1).

Step 11B: 4-[4-Bromo-5-chloro-2-4,4-dimethyl-3,4-dihydro-2H-quinoline-1-sulfonyl)-phenoxy]-butan-1-ol To a solution of 1,4-butanediol (0.44 mL, 5 mmole) in DMF (5 mL) at 0° C. was added sodium hydride (60%, 48 mg, 1.2 mmole) and the mixture stirred for 10 minutes. A solution of 1-(5-bromo-4-chloro-2-fluoro-benzenesulfonyl)-4,4-dimethyl-1,2,3,4-tetrahydro-quinoline (0.41 g, 1 mmole) in DMF (5 mL) was added. The mixture warmed to rt and was stirred for 1 hour. 1N hydrochloric acid solution (1 mL) was added and the mixture was extracted with ethyl acetate. The organic layer was washed with brine and was dried over anhydrous $MgSO_4$. Concentration of the filtrate provided a residue that was purified by silica gel chromatography [eluent: 40% ethyl acetate in hexane] to afford 4-[4-bromo-5-chloro-2-(4,4-dimethyl-3,4-dihydro-2H-quinoline-1-sulfonyl)-phenoxy]-butan-1-ol as a light yellow foam (0.86 g). MS: 503.9 (M+H)$^+$; $t_R$=2.66 min (method 1).

Step 11C: 4-[5-Chloro-2-(4,4-dimethyl-3,4-dihydro-2H-quinoline-1-sulfonyl)-4-(4,4,5,5-tetramethyl-[1,3,2]dioxaborolan-2-yl)-phenoxy]-butan-1-ol A mixture of 4-[4-bromo-5-chloro-2-(4,4-dimethyl-3,4-dihydro-2H-quinoline-1-sulfonyl)-phenoxy]-butan-1-ol (0.82 g, 1.6 mmole), bis(pinacolato)diboron (0.62 g, 2.5 mmole), PdCl$_2$(dppf)$_2$ (0.10 g, 0.13 mmole), and potassium acetate (0.48 g, 4.9 mmol) in dioxane (8 mL) was degassed with N$_2$ for 5 min. The reaction vessel was sealed and heated at 90° C. for 15 hrs. The mixture was filtered through Celite to remove solids. The Celite was washed by ethyl acetate several times. The combined solution was washed with water and brine and dried over MgSO$_4$. After filtration and concentration, purification by silica gel column chromatography eluting with up to 25% ethyl acetate in hexanes yielded 4-[5-chloro-2-(4,4-dimethyl-3,4-dihydro-2H-quinoline-1-sulfonyl)-4-(4,4,5,5-tetramethyl-[1,3,2]dioxaborolan-2-yl)-phenoxy]-butan-1-ol as a white foam. MS: 550.0 (M+H)$^+$; $t_R$=2.74 min (method 1).

Step 11D: 5-[2-Chloro-5-(4,4-dimethyl-3,4-dihydro-2H-quinoline-1-sulfonyl)-4-(4-hydroxy-butoxy)-phenyl]-2-trifluoromethyl-isonicotinonitrile A mixture of 4-[5-Chloro-2-(4,4-dimethyl-3,4-dihydro-2H-quinoline-1-sulfonyl)-4-(4,4,5,5-tetramethyl-[1,3,2]dioxaborolan-2-yl)-phenoxy]-butan-1-ol (270.0 mg, 0.49 mmol), 5-bromo-2-trifluoromethyl-isonicotinonitrile (112 mg, 0.45 mmol), Pd(Ph$_3$P)$_4$ (57 mg, 0.05 mmol) and Na$_2$CO$_3$ (286 mg, 2.7 mmol) in dioxane (4 mL) and water (0.4 mL) was degassed with N$_2$ for 5 min. The reaction vessel was sealed and then heated at 100° C. for 16 hrs. The mixture was then partitioned between ethyl acetate (20 mL) and water (10 mL). The organic layer was washed with brine (2×10 mL), dried over MgSO$_4$, filtered and concentrated to give a material which was purified by TLC plates eluting with 30% acetone in hexanes to give 5-[2-chloro-5-(4,4-dimethyl-3,4-dihydro-2H-quinoline-1-sulfonyl)-4-(4-hydroxy-butoxy)-phenyl]-2-trifluoromethyl-isonicotinonitrile 11-1 as a white solid (95 mg). MS: 594.2 (M+H)$^+$; $t_R$=2.94 min (method 1).

Similarly, 5-[2-chloro-5-(4,4-dimethyl-3,4-dihydro-2H-quinoline-1-sulfonyl)-4-(2-hydroxy-ethoxy)-phenyl]-2-trifluoromethyl-isonicotinonitrile 11-2 was prepared. MS: 566.1 (M+H)$^+$; $t_R$=8.84 min (method 2).

Similarly, 5-[2-chloro-5-(4,4-dimethyl-3,4-dihydro-2H-quinoline-1-sulfonyl)-4-(3-hydroxy-propoxy)-phenyl]-2-trifluoromethyl-isonicotinonitrile 11-3 was prepared. MS: 580.1 (M+H)$^+$; $t_R$=8.75 min (method 2).

Example 12

4-[5-Chloro-4-(4-cyano-6-trifluoromethyl-pyridin-3-yl)-2-(4,4-dimethyl-3,4-dihydro-2H-quinoline-1-sulfonyl)-phenoxy]-butyric acid

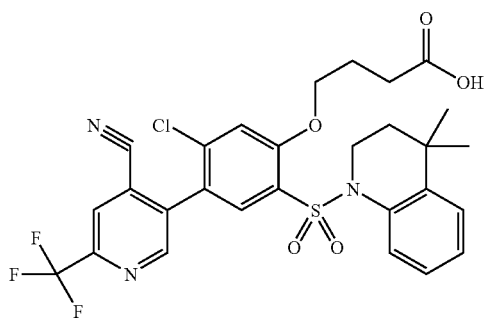

Step 12A: 4-[5-chloro-4-(4-cyano-6-trifluoromethyl-pyridin-3-yl)-2-(4,4-dimethyl-3,4-dihydro-2H-quinoline-1-sulfonyl)-phenoxy]-butyric acid To 5-[2-chloro-5-(4,4-dimethyl-3,4-dihydro-2H-quinoline-1-sulfonyl)-4-(4-hydroxy-butoxy)-phenyl]-2-trifluoromethyl-isonicotinonitrile 11-1 (65 mg, 0.11 mmol) in a mixture of DCM (0.5 mL), acetonitrile (0.5 mL) and water (0.6 mL) was added NaIO$_4$ (71 mg, 0.33 mmol) and RuCl$_3$ (4.5 mg, 0.022 mmol). After stirring at rt for 30 minutes, 0.5 mL of methanol was added. The mixture was stirred for 30 minutes, filtered, and purified by prep. LCMS to afford 4-[5-chloro-4-(4-cyano-6-trifluoromethyl-pyridin-3-yl)-2-(4,4-dimethyl-3,4-dihydro-2H-quinoline-1-sulfonyl)-phenoxy]-butyric acid 12-1. MS: 608.1 (M+H)$^+$; $t_R$=5.87 min (method 5).

Similarly, [5-chloro-4-(4-cyano-6-trifluoromethyl-pyridin-3-yl)-2-(4,4-dimethyl-3,4-dihydro-2H-quinoline-1-sulfonyl)-phenoxy]-acetic acid 12-2 was prepared. MS: 579.9 (M+H)$^+$; $t_R$=8.86 min (method 2).

Similarly, 3-[5-chloro-4-(4-cyano-6-trifluoromethyl-pyridin-3-yl)-2-(4,4-dimethyl-3,4-dihydro-2H-quinoline-1-sulfonyl)-phenoxy]-propionic acid 12-3 was prepared. MS: 593.9 (M+H)$^+$; $t_R$=8.96 min (method 2).

Example 13

1-[2-Chloro-5-(2,3,4,5-tetrahydro-benzo[b]azepine-1-sulfonyl)-phenyl]-6-methyl-4-trifluoromethyl-1H-pyrimidin-2-one

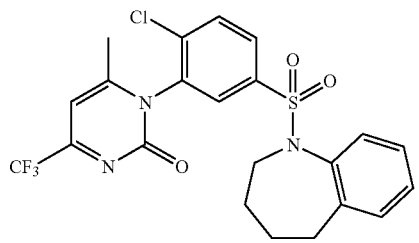

Step 13A: 1-(3-Nitro-4-chloro-benzenesulfonyl)-2,3,4,5-tetrahydro-1H-benzo[b]azepine To 4-chloro-3-nitrobenzenesulfonyl chloride (2.56 g, 10 mmol) in dry DCM (20 mL) was added 2,3,4,5-tetrahydro-1H-benzo[b]azepine (1.54 g, 10.5 mmol) and triethylamine (3.3 mL, 25 mmol). The mixture was stirred at ambient temperature for 16 hrs. The mixture was then diluted with 40 mL of DCM and 30 mL of water. The organic layer was separated, washed with brine (2×20 mL), dried over MgSO$_4$, and evaporated to afford 1-(3-nitro-4-chloro-benzenesulfonyl)-2,3,4,5-tetrahydro-1H-benzo[b]azepine as a yellow solid (3.6 g).

Step 13B: 2-Chloro-5-2,3,4,5-tetrahydro-benzo[b]azepine-1-sulfonyl)-phenylamine

To 1-(3-nitro-4-chloro-benzenesulfonyl)-2,3,4,5-tetrahydro-1H-benzo[b]azepine (3.6 g, 10 mmol) in THF (50 mL) and water (50 mL) was added sodium hydrosulfite (10.2 g, 50 mmol). The mixture was stirred at ambient temperature for 2 hrs. Ethyl acetate (150 mL) and sat. NH$_4$Cl (150 mL) were added. The organic layer was separated, washed with brine (2×50 mL) and dried over MgSO$_4$. Concentration and purification by silica gel column chromatography eluting with hexane/ethyl acetate (4/1 to 1/1) yielded 2-chloro-5-(2,3,4,5-tetrahydro-benzo[b]azepine-1-sulfonyl)-phenylamine as pale yellow solid (3.4 g). MS: 337.0 (M+H)$^+$; $t_R$=2.85 min (method 1).

Step 13C: [2-Chloro-5-(2,3,4,5-tetrahydro-benzo[b]azepine-1-sulfonyl)-phenyl]-urea To 2-chloro-5-(2,3,4,5-tetrahydro-benzo[b]azepine-1-sulfonyl)-phenylamine (3.4 g, 10 mmol) in DCE (20 mL) and HOAc (20 mL) was added urea (1.2 g, 20 mmol). The mixture was stirred at 100° C. for 24 hrs and was then partitioned between DCM (150 mL) and sat. NaHCO$_3$ solution (150 mL). Additional solid NaHCO$_3$ was added until the aqueous layer pH value was 8. The organic layer was separated, washed with saturated NaHCO$_3$ and brine, dried over MgSO$_4$ and evaporated to obtain a yellow oil. The oil was re-dissolved in DCM (10 mL) and ether (50 mL) and stood at rt for 12 hrs to give [2-chloro-5-(2,3,4,5-tetrahydro-benzo[b]azepine-1-sulfonyl)-phenyl]-urea (1.7 g) as a white solid. MS: 379.7 (M+H)$^+$; $t_R$=6.67 min (method 2).

Step 13D: 1-[2-chloro-5-(2,3,4,5-tetrahydro-benzo[b]azepine-1-sulfonyl)-phenyl]-6-methyl-4-trifluoromethyl-1H-pyrimidin-2-one To [2-chloro-5-(2,3,4,5-tetrahydro-benzo[b]azepine-1-sulfonyl)-phenyl]-urea (38 mg, 0.1 mmol) in 13% (v/v) H$_2$SO$_4$ in EtOH was added 1,1,1-trifluoro-2,4-pentanedione (15 µL, 0.15 mmol). The mixture was heated at 80° C. for 6 hrs, followed by neutralization with 6N NaOH solution. Purification by prep. LCMS yielded 1-[2-chloro-5-(2,3,4,5-tetrahydro-benzo[b]azepine-1-sulfonyl)-phenyl]-6-methyl-4-trifluoromethyl-1H-pyrimidin-2-one 13-1. MS: 497.7 (M+H)$^+$; $t_R$=8.14 min (method 2).

The following example compounds were prepared using this procedure.

| Ex. | A | —NR$_2$R$_{2a}$ | MS (M+H)$^+$ | $t_R$ (min) method 2 |
|---|---|---|---|---|
| 13-1 | 6-methyl-4-trifluoromethyl-1H-pyrimidin-2-one-1-yl | 2,3,4,5-tetrahydro-benzo[b]azepin-1-yl | 497.7 | 8.14 |
| 13-2 | 4,6-dimethyl-1H-pyrimidin-2-one-1-yl | 2,3,4,5-tetrahydro-benzo[b]azepin-1-yl | 443.8 | 6.22 |
| 13-3 | 6-methyl-4-trifluoromethyl-1H-pyrimidin-2-one-1-yl | N-methyl-N-(2-methoxyphenyl)amine | 487.7 | 7.50 |
| 13-4 | 6-methyl-4-trifluoromethyl-1H-pyrimidin-2-one-1-yl | 3,4-dihydro-2H-quinolin-1-yl | 484.0 | 7.74 |

Example 14

3-[2-Chloro-5-(2,3,4,5-tetrahydro-benzo[b]azepine-1-sulfonyl)-phenyl]-2,6-dimethyl-3H-pyrimidin-4-one

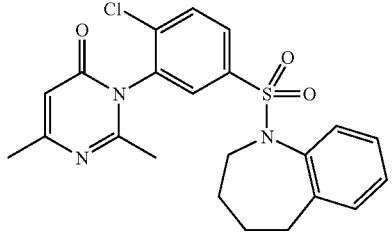

Step 14A: N-[2-Chloro-5-(2,3,4,5-tetrahydro-benzo[b]azepine-1-sulfonyl)-phenyl]-3-oxo-butyramide To 2-chloro-5-(2,3,4,5-tetrahydro-benzo[b]azepine-1-sulfonyl)-phenylamine (1.0 g, 3 mmol, step 4B) in dry toluene (60 mL) was added tert-butyl acetoacetate (0.75 mL, 4.5 mmol) and 4-dimethyl-aminopyridine (0.37 g, 3 mmol). The mixture was refluxed under N$_2$ for 16 hrs. After the removal of toluene, the reaction residue was repartitioned with ethyl acetate (100 mL) and water (50 mL). The organic layer was washed with sat. NH$_4$Cl (2×50 mL) and brine (2×50 mL) and was dried over MgSO$_4$. Concentration and purification by silica gel column chromatography eluting with hexane/ethyl acetate (3/1 to 1/1) yielded N-[2-chloro-5-(2,3,4,5-tetrahydro-benzo[b]azepine-1-sulfonyl)-phenyl]-3-oxo-butyramide as yellowish solid (1.0 g). MS: 421.0 (M+H)$^+$; $t_R$=2.74 min (method 1).

Step 14B: N-[2-Chloro-5-(2,3,4,5-tetrahydro-benzo[b]azepine-1-sulfonyl)-phenyl]-3-imino-butyramide To N-[2-chloro-5-(2,3,4,5-tetrahydro-benzo[b]azepine-1-sulfonyl)-phenyl]-3-oxo-butyramide (0.42 g, 1 mmol) in dry ethanol (4 mL) was added ammonium acetate (0.37 g, 3 mmol). The mixture was heated at 65° C. under stirring for 16 hrs. The filtration of the reaction mixture afforded N-[2-chloro-5-(2,3,4,5-tetrahydro-benzo[b]azepine-1-sulfonyl)-phenyl]-3-imino-butyramide as white solid (0.24 g).

Step 14C: 3-[2-Chloro-5-(2,3,4,5-tetrahydro-benzo[b]azepine-1-sulfonyl)-phenyl]-2,6-dimethyl-3H-pyrimidin-4-one To N-[2-chloro-5-(2,3,4,5-tetrahydro-benzo[b]azepine-1-sulfonyl)-phenyl]-3-imino-butyramide (42 mg, 0.1 mmol) in acetic anhydride (1 mL) was added 4-dimethyl-aminopyridine (6 mg, 0.1 mmol). The mixture was heated at 85° C. under stirring for 16 hrs. The mixture was then subjected to purification by prep. LCMS to afford 3-[2-chloro-5-(2,3,4,5- tetrahydro-benzo[b]azepine-1-sulfonyl)-phenyl]-2,6-dimethyl-3H-pyrimidin-4-one 14-1. MS: 443.8 (M+H)+; $t_R$=6.94 min (method 2).

Example 15

4-Chloro-5-(4-cyano-6-trifluoromethyl-pyridin-3-yl)-2-methoxy-N-methyl-N-phenyl-benzenesulfonamide

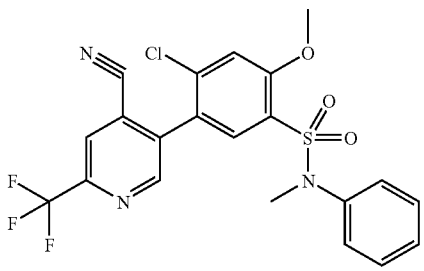

Step 15A: 5-(2-chloro-4-methoxy-phenyl)-2-trifluoromethylisonicotinonitrile

To a mixture of 5-bromo-2-trifluoromethyl-isonicotinonitrile 1-1 (2.51 g, 10 mmol) in dioxane (3.3 mL) and water (3.3 mL), were added 2-chloro-4-methoxyphenylboronic acid (2.3 g, 12.5 mmol) and Na₂CO₃ (6.3 g). The mixture was purged with nitrogen gas for 10 min, then Pd(PPh₃)₄ (1.2 g, 1.0 mmol) was added. The mixture was stirred in a sealed vessel at 85° C. for 6 hrs, then extracted by ethyl acetate. The organic layer was washed with water, dried over MgSO₄. Concentration and purification by silica gel column chromatography eluting with hexane/ethyl acetate (10/1) yielded 5-(2-chloro-4-methoxy-phenyl)-2-trifluoromethylisonicotinonitrile (1.31 g). $t_R$=2.96 min (method 1).

Step 15B: 4-Chloro-5-(4-cyano-6-trifluoromethyl-pyridin-3-yl)-2-methoxy-benzenesulfonyl chloride To 5-(2-chloro-4-methoxy-phenyl)-2-trifluoromethyl-isonicotinonitrile (0.7 g, 2.24 mmol) in chloroform (6 mL), was added to ClSO₃H (0.62 mL). The solution was stirred at rt for 16 hrs. The solvent was removed and MeCN (3 mL) was added, followed by addition of POCl₃ (3 mL). The mixture was heated at 60° C. for 16 hrs, then concentrated. The remainder was poured into ice water with stirring. The resulting solid was filtered, dried in vacuo over 2 days to yield 4-chloro-5-(4-cyano-6-trifluoromethyl-pyridin-3-yl)-2-methoxy-benzenesulfonyl chloride (0.79 g) as a pale yellow solid. $t_R$=2.92 min (method 1).

Step 15C: 4-Chloro-5-(4-cyano-6-trifluoromethyl-pyridin-3-yl)-2-methoxy-N-methyl-N-phenyl-benzenesulfonamide To 4-chloro-5-(4-cyano-6-trifluoromethyl-pyridin-3-yl)-2-methoxy-benzenesulfonyl chloride (100 mg, 0.24 mmol) in dichloromethane (3 mL), was added pyridine (0.04 mL, 0.48 mmol), followed by addition of N-methylaniline (0.05 mL, 0.48 mmol). The mixture was stirred at r.t. for 16 hrs, then poured into 1 N HCl solution (10 mL). The product was extracted with ethyl acetate and the organic layer was washed with 1N HCl and water, then was dried over MgSO₄. Concentration gave 4-chloro-5-(4-cyano-6-trifluoromethyl-pyridin-3-yl)-2-methoxy-N-methyl-N-phenyl-benzenesulfonamide 15-1, (108 mg). MS: 482.0 (M+H)+; $t_R$=8.76 min (method 2).

The following compounds were prepared using this procedure

| Ex. | —NR₂R₂ₐ | Observed MS[1] | $t_R$ (min) | HPLC method |
|---|---|---|---|---|
| 15-1 | N-phenyl-methylamino | 482.0 | 8.76 | 2 |
| 15-2 | 4,4-dimethyl-1,2,3,4-tetrahydro-quinolin-1-yl | 553.3 | 6.90 | 3 |
| 15-3 | N-(3-chloro-phenyl)-methylamino | 533.2 | 9.36 | 3 |
| 15-4 | N-(4-chloro-2-methyl-phenyl)-methylamino | 530.1 | 9.74 | 2 |
| 15-5 | N-(2-methyl-phenyl)-methylamino | 513.3 | 9.14 | 3 |
| 15-6 | N-(4-fluoro-phenyl)-methylamino | 517.3 | 8.98 | 3 |
| 15-7 | N-(2-chloro-phenyl)-methylamino | 533.2 | 9.10 | 3 |
| 15-8 | N-(3,4-dichloro-phenyl)-methylamino | 567.4 | 9.77 | 3 |
| 15-9 | N-(3-methyl-phenyl)-methylamino | 513.3 | 9.24 | 3 |
| 15-10 | N-(4-chloro-phenyl)-methylamino | 533.2 | 9.40 | 3 |
| 15-11 | N-(3-fluoro-phenyl)-methylamino | 517.3 | 9.03 | 3 |
| 15-12 | N-(2-fluoro-phenyl)-methylamino | 517.3 | 8.90 | 3 |
| 15-13 | N-(4-methoxy-phenyl)-methylamino | 529.2 | 8.86 | 3 |
| 15-14 | N-(3-methoxy-phenyl)-methylamino | 512.3 | 8.91 | 3 |
| 15-15 | N-(2-methoxy-6-methyl-phenyl)-methylamino | 526.1 | 8.93 | 3 |
| 15-16 | N-(2-methoxy-phenyl)-methylamino | 512.1 | 8.57 | 2 |
| 15-17 | 2,3,4,5-tetrahydro-1H-benzo[b]azepin-1-yl | 522.0 | 8.78 | 2 |
| 15-18 | N-(Pyridin-2-yl)-methylamino | 483.0 | 8.16 | 2 |
| 15-19 | N-(3-methyl-pyridin-2-yl)-methylamino | 497.1 | 7.77 | 2 |
| 15-20 | N-(6-Methoxy-pyridin-2-yl)-methylamino | 513.1 | 7.78 | 2 |
| 15-21 | N-(Isobutyl)-methylamino | 462.1 | 9.22 | 2 |
| 15-22 | phenylmethylamino | 496.1 | 9.14 | 2 |
| 15-23 | 2-phenylethylamino | 510.0 | 9.40 | 2 |
| 15-24 | 3-phenylpropylamino | — | 6.91 | 3 |
| 15-25 | N-(2-Dimethylamino-ethyl)-methylamino | 477.4 | 5.49 | 3 |
| 15-26 | N-(ethoxycarbonylmethyl)-methylamino | — | 5.91 | 3 |
| 15-27 | N-(2-hydroxyethyl)-methylamino | 467.3 | 5.06 | 3 |
| 15-28 | butylamino | — | 6.42 | 3 |
| 15-29 | N-(2-methoxybenzyl)-methylamino | 526.3 | 9.25 | 3 |
| 15-30 | N-(2,2-Dimethyl-propyl)-methylamino | 493.3 | 9.45 | 3 |
| 15-31 | N-(2-chloro-benzyl)-methylamino | 547.2 | 9.54 | 3 |
| 15-32 | N-(3-methoxybenzyl)-methylamino | 543.2 | 9.14 | 3 |
| 15-33 | N-(4-fluorobenzyl)-methylamino | 531.4 | 9.24 | 3 |
| 15-34 | N-(3-fluorobenzyl)-methylamino | 531.2 | 9.23 | 3 |
| 15-35 | N-(2-fluorobenzyl)-methylamino | 531.2 | 9.21 | 3 |
| 15-36 | 1,2,3,4-tetrahydro-isoquinolin-yl | 525.2 | 9.27 | 3 |
| 15-37 | N-(4-chlorobenzyl)-methylamino | 549.1 | 9.62 | 3 |
| 15-38 | N-[(6-methyl-pyridin-2-yl)-methyl]-methylamino | 511.3 | 8.35 | 3 |
| 15-39 | N-(Furan-2-ylmethyl)-methylamino | 486.0 | 8.42 | 3 |
| 15-40 | N-(4-methoxybenzyl)-methylamino | 543.2 | 8.82 | 3 |
| 15-41 | N-(3,4-dichlorobenzyl)-methylamino | 565.0 | 9.72 | 3 |
| 15-42 | N-(2,3-dichlorobenzyl)-methylamino | 563.9 | 9.59 | 3 |
| 15-43 | N-[(R)-1-phenyl-ethyl]-methylamino | 510.3 | 9.10 | 3 |
| 15-44 | N-[(S)-1-phenyl-ethyl]-methylamino | 510.3 | 9.07 | 3 |

[1][M + H + NH₃] is observed in most of cases when HPLC-MS Method 3 was used.

Example 16

[5-Chloro-4-(4-cyano-6-trifluoromethyl-pyridin-3-yl)-2-(4,4-dimethyl-3,4-dihydro-2H-quinoline-1-sulfonyl)-phenyl]-acetic acid methyl ester

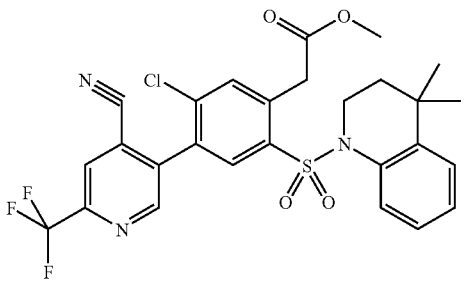

Step 16A: 5-Bromo-4-chloro-2-fluoro-benzenesulfonyl chloride

A mixture of 4-bromo-3-chloro-1-fluorobenzene (10 g, 47.6 mmol) and chlorosulfonic acid (20 mL) was heated at 90° C. with stirring for 2 hrs. After cooling to rt, the mixture was poured into ice water (200 mL). The resulting precipitate was filtered, washed with water, and dried to yield 5-bromo-4-chloro-2-fluoro-benzenesulfonyl chloride as a white solid (13.2 g).

Step 16B: 1-(5-Bromo-4-chloro-2-fluoro-benzenesulfonyl)-4,4-dimethyl-1,2,3,4-tetrahydro-quinoline To 4,4-dimethyl-1,2,3,4-tetrahydro-quinoline (2.2 g, 13.66 mmol) in a mixture of water (60 mL) and acetonitrile (40 mL) containing NaHCO$_3$ (3.44 g, 41.0 mmol), was added 5-bromo-4-chloro-2-fluoro-benzenesulfonyl chloride (4.2 g, 13.66 mmol) in acetonitrile (20 mL) slowly with vigorous stirring. After addition, the mixture was stirred for 3 hrs. The resulting precipitate was filtered, washed with hexane and dried to yield 1-(5-bromo-4-chloro-2-fluoro-benzenesulfonyl)-4,4-dimethyl-1,2,3,4-tetrahydro-quinoline as a light brown solid (5.0 g).

Step 16C: 2-[4-Bromo-5-chloro-2-(4,4-dimethyl-3,4-dihydro-2H-quinoline-1-sulfonyl)-phenyl]-malonic acid dimethyl ester To a dry DMF (10 mL) solution containing dimethyl malonate (0.79 mL, 6.9 mmol), was added NaH (276 mg, 6.9 mmol) slowly at 0° C. under N$_2$. The slurry was stirred for 10 min, then 1-(5-bromo-4-chloro-2-fluoro-benzenesulfonyl)-4,4-dimethyl-1,2,3,4-tetrahydro-quinoline (1.0 g, 2.3 mmol) in dry DMF (5 mL) was added dropwise. The mixture was heated at 80° C. for 24 hrs, cooled to rt, carefully quenched with 1N HCl (10 mL), and extracted with ethyl acetate. The organic layer was washed with saturated aq. NaHCO$_3$ solution and water, then was dried over MgSO$_4$. After filtration and concentration, the residue was purified via silica gel flash column chromatography eluting with hexane/ethyl acetate (100/15) to yield 2-[4-bromo-5-chloro-2-(4,4-dimethyl-3,4-dihydro-2H-quinoline-1-sulfonyl)-phenyl]-malonic acid dimethyl ester (0.75 g). MS: 545.9 (M+H)$^+$; $t_R$=2.64 min (method 1)

Step 16D: 2-[4-Bromo-5-chloro-2-(4,4-dimethyl-3,4-dihydro-2H-quinoline-1-sulfonyl)-phenyl]-acetic acid methyl ester 2-[4-Bromo-5-chloro-2-(4,4-dimethyl-3,4-dihydro-2H-quinoline-1-sulfonyl)-phenyl]-malonic acid dimethyl ester (0.72 g, 1.32 mmol) was heated at 120° C. for 5 hrs in DMSO which contained NaCl (153.5 mg, 2.65 mmol) and 2 drops of water. After cooling to rt, the mixture was extracted with ethyl acetate, washed with water and brine, and was dried over MgSO$_4$. Filtration and concentration yielded a residue which was purified via silica gel flash column chromatography eluting with hexane/ethyl acetate (100/15) to give 2-[4-bromo-5-chloro-2-(4,4-dimethyl-3,4-dihydro-2H-quinoline-1-sulfonyl)-phenyl]-acetic acid methyl ester (512 mg). MS: 487.9 (M+H)$^+$; $t_R$=2.75 min (method 1)

Step 16E: 5-Chloro-2-(4,4-dimethyl-3,4-dihydro-2H-quinoline-1-sulfonyl)-4-(4,4,5,5-tetramethyl-[1,3,2]dioxaborolan-2-yl)-phenyl-acetic acid methyl ester 5-Chloro-2-(4,4-dimethyl-3,4-dihydro-2H-quinoline-1-sulfonyl)-4-(4,4,5,5-tetramethyl-[1,3,2]dioxaborolan-2-yl)-phenyl]-acetic acid methyl ester was prepared according to Step 3C of Example 3 using 2-[4-bromo-5-chloro-2-(4,4-dimethyl-3,4-dihydro-2H-quinoline-1-sulfonyl)-phenyl]-acetic acid methyl ester as the starting material. MS: 534.1 (M+H)$^+$; $t_R$=2.98 min (method 1)

Step 16F: [5-Chloro-4-(4-cyano-6-trifluoromethyl-pyridin-3-yl)-2-(4,4-dimethyl-3,4-dihydro-2H-quinoline-1-sulfonyl)-phenyl]-acetic acid methyl ester

[5-Chloro-4-(4-cyano-6-trifluoromethyl-pyridin-3-yl)-2-(4,4-dimethyl-3,4-dihydro-2H-quinoline-1-sulfonyl)-phenyl]-acetic acid methyl ester 16-1 (51 mg) was prepared according to Step 3D of Example 3 using 5-chloro-2-(4,4-dimethyl-3,4-dihydro-2H-quinoline-1-sulfonyl)-4-(4,4,5,5-tetramethyl-[1,3,2]dioxaborolan-2-yl)-phenyl]-acetic acid methyl ester (190 mg, crude) and 5-bromo-2-trifluoromethyl-isonicotinonitrile 1-1 (60 mg) as the starting materials. MS: 578.1 (M+H)$^+$; $t_R$=9.26 min (method 2).

Example 17

[5-Chloro-4-(4-cyano-6-trifluoromethyl-pyridin-3-yl)-2-(4,4-dimethyl-3,4-dihydro-2H-quinoline-1-sulfonyl)-phenyl]-acetic acid

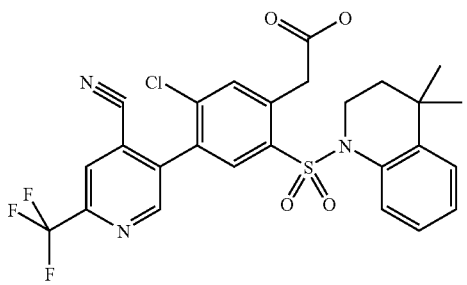

Step 17A: 5-Chloro-4-(4-cyano-6-trifluoromethyl-pyridin-3-yl)-2-(4,4-dimethyl-3,4-dihydro-2H-quinoline-1-sulfonyl)-phenyl]-acetic acid

[5-Chloro-4-(4-cyano-6-trifluoromethyl-pyridin-3-yl)-2-(4,4-dimethyl-3,4-dihydro-2H-quinoline-1-sulfonyl)-phenyl]-acetic acid methyl ester 16-1 (36.4 mg, 0.06 mmol) was heated in a mixture of THF (2 mL) and 6N HCl (2 mL) for 16 hrs. The mixture was concentrated and extracted with ethyl acetate. The organic layer was separated, dried and purified by a prep. TLC plate eluting with 10% MeOH in DCM to yield 5-chloro-4-(4-cyano-6-trifluoromethyl-pyridin-3-yl)-2-(4,4-dimethyl-3,4-dihydro-2H-quinoline-1-sulfonyl)-phenyl]-acetic acid 17-1 (27.3 mg). MS: 564.0 (M+H)$^+$; $t_R$=8.96 min (method 2).

Example 18

4-[5-Chloro-4-(4-cyano-6-trifluoromethyl-pyridin-3-yl)-2-(methyl-pyridin-2-yl-sulfamoyl)-phenoxy]-butyric acid

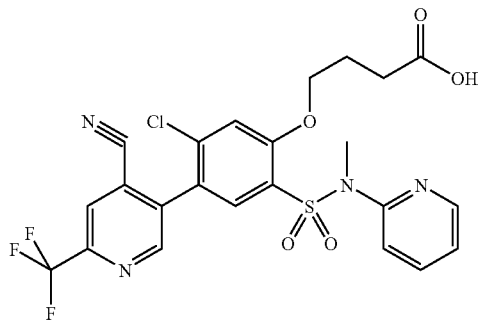

Step 18A: 5-Bromo-4-chloro-2-fluoro-N-methyl-N-pyridin-2-yl-benzenesulfonamide

To 5-bromo-4-chloro-2-fluorobenzenesulfonyl chloride (1.5 g, 4.89 mmol) in dry DCM (15 mL), at −20° C. was added pyridine (1.98 mL, 24.5 mmol) followed by methyl-pyridin-2-yl-amine (1.06 g, 9.78 mmol). The mixture was allowed to warm slowly to ambient temperature over 16 hrs. 1N NaOH solution (5 mL) was added and stirred for 15 mins. The mixture was extracted with DCM and the organics were washed with brine, dried over MgSO$_4$ and the filtrate evaporated. The residue was purified by silica gel chromatography [eluent: 10% ethyl acetate in hexane] to give 5-bromo-4-chloro-2-fluoro-N-methyl-N-pyridin-2-yl-benzenesulfonamide as an oil (0.57 g, 31%). MS: 380.9 (M+H)$^+$; $t_R$=2.80 min (method 1).

Step 18B: 5-Bromo-4-chloro-2-(4-hydroxy-butoxy)-N-methyl-N-pyridin-2-yl-benzenesulfonamide To a solution of 1,4-butanediol (0.315 mL, 3.6 mmol) in DMF (2.5 mL) at ambient temperature was added sodium hydride (60%, 34 mg, 0.85 mmol) and the mixture was stirred for 15 minutes. A solution of 5-bromo-4-chloro-2-fluoro-N-methyl-N-pyridin-2-yl-benzenesulfonamide (0.268 g, 0.71 mmol) in DMF (2.5 mL) was added and the mixture heated at 50° C. for 2 h. The solvent was removed in vacuo and water and DCM were added. The mixture was extracted with DCM. The organic layer was washed with brine and was dried over anhydrous MgSO$_4$. Concentration of the filtrate provided a residue that was purified by silica gel chromatography [eluent: 50% ethyl acetate in hexane] to afford 5-bromo-4-chloro-2-(4-hydroxy-butoxy)-N-methyl-N-pyridin-2-yl-benzenesulfonamide as a solid (0.309 g). MS: 451.0 (M+H)$^+$; $t_R$=2.59 min (method 1).

Similarly, 5-Bromo-4-chloro-2-(3-hydroxy-propoxy)-N-methyl-N-pyridin-2-yl-benzenesulfonamide was prepared. MS: 437.0 (M+H)$^+$; $t_R$=2.54 min (method 1).
Similarly, 5-Bromo-4-chloro-2-(2-hydroxy-ethoxy)-N-methyl-N-pyridin-2-yl-benzene sulfonamide was prepared. MS: 423.0 (M+H)$^+$; $t_R$=2.52 min (method 1).

Step 18C: 4-Chloro-2-(4-hydroxy-butoxy)-N-methyl-N-pyridin-2-yl-5-(4,4,5,5-tetramethyl-[1,3,2]dioxaborolan-2-yl)-benzenesulfonamide A mixture of 5-bromo-4-chloro-2-(4-hydroxy-butoxy)-N-methyl-N-pyridin-2-yl-benzenesulfonamide (0.309 g, 0.69 mmol), bis(pinacolato)diboron (0.268 g, 1.04 mmol), PdCl$_2$(dppf)$_2$ (0.044 g, 0.054 mmol), and potassium acetate (0.2 g, 2.1 mmol) in dioxane (6 mL) was degassed with N$_2$ for 5 min. The reaction vessel was sealed and heated at 90° C. for 15 hrs. The mixture was absorbed onto silica gel and was purified by silica gel column chromatography eluting with 50% up to 100% ethyl acetate in hexanes to yield 4-chloro-2-(4-hydroxy-butoxy)-N-methyl-N-pyridin-2-yl-5-(4,4,5,5-tetramethyl-[1,3,2]dioxaborolan-2-yl)-benzenesulfonamide as an oil. MS: 497.2 (M+H)$^+$; $t_R$=2.79 min (method 1).
Similarly, 4-chloro-2-(3-hydroxy-propoxy)-N-methyl-N-pyridin-2-yl-5-(4,4,5,5-tetramethyl-[1,3,2]dioxaborolan-2-yl)-benzenesulfonamide was prepared. MS: 483.2 (M+H)$^+$; $t_R$=2.68 min (method 1).
Similarly, 4-chloro-2-(2-hydroxy-ethoxy)-N-methyl-N-pyridin-2-yl-5-(4,4,5,5-tetramethyl[1,3,2]dioxaborolan-2-yl)-benzenesulfonamide was prepared. MS: 469.1 (M+H)$^+$; $t_R$ 2.68 min (method 1).

Step 18D: 4-Chloro-5-(4-cyano-6-trifluoromethyl-pyridin-3-yl)-2-(4-hydroxy-butoxy)-N-methyl-N-pyridin-2-yl-benzenesulfonamide A mixture of 4-chloro-2-(4-hydroxy-butoxy)-N-methyl-N-pyridin-2-yl-5-(4,4,5,5-tetramethyl-[1,3,2]dioxaborolan-2-yl)-benzenesulfonamide (150 mg, 0.34 mmol), 5-bromo-2-trifluoromethyl-isonicotinonitrile (111 mg, 0.44 mmol), Pd(Ph$_3$P)$_4$ (40 mg, 0.034 mmol) and Na$_2$CO$_3$ (217 mg, 2.1 mmol) in dioxane (2 mL) and water (0.2 mL) was degassed with N$_2$ for 5 min. The reaction vessel was sealed and then heated at 90° C. for 16 hrs. The mixture was absorbed onto silica gel and purified by chromatography on silica gel eluting with 20-25% acetone in hexanes to give 4-chloro-5-(4-cyano-6-trifluoromethyl-pyridin-3-yl)-2-(4-hydroxy-butoxy)-N-methyl-N-pyridin-2-yl-benzenesulfonamide as an oil (69 mg). A small sample was also purified by prep. LCMS. MS: 541.1 (M+H)$^+$; $t_R$=7.59 min (method 2).
Similarly, 4-chloro-5-(4-cyano-6-trifluoromethyl-pyridin-3-yl)-2-(3-hydroxy-propoxy)-N-methyl-N-pyridin-2-yl-benzenesulfonamide was prepared. MS: 527.1 (M+H)$^+$; $t_R$=7.43 min (method 2).
Similarly, 4-chloro-5-(4-cyano-6-trifluoromethyl-pyridin-3-yl)-2-(2-hydroxy-ethoxy)-N-methyl-N-pyridin-2-yl-benzenesulfonamide was prepared. MS: 513.1 (M+H)$^+$; $t_R$=2.66 min (method 1).

Step 18E: 4-[5-Chloro-4-(4-cyano-6-trifluoromethyl-pyridin-3-yl)-2-(methyl-pyridin-2-yl-sulfamoyl)-phenoxy]-butyric acid To 4-chloro-5-(4-cyano-6-trifluoromethyl-pyridin-3-yl)-2-(4-hydroxy-butoxy)-N-methyl-N-pyridin-2-yl-benzenesulfonamide (45 mg, 0.083 mmol) in a mixture of DCM (0.3 mL), acetonitrile (0.3 mL) and water (0.4 mL) was added NaIO$_4$ (54 mg, 0.25 mmol) and RuCl$_3$ (2.7 mg, 0.013 mmol). After stirring at rt for 20 minutes, 0.5 mL of methanol was added. The mixture was stirred for 5 minutes, filtered, and purified by prep. LCMS to afford 4-[5-chloro-4-(4-cyano-6-trifluoromethyl-pyridin-3-yl)-2-(methyl-pyridin-2-yl-sulfamoyl)-phenoxy]-butyric acid 18-1. MS: 555.1 (M+H)$^+$; t$_R$=7.61 min (method 2).

Similarly, [3-[5-chloro-4-(4-cyano-6-trifluoromethyl-pyridin-3-yl)-2-(methyl-pyridin-2-yl-sulfamoyl)-phenoxy]-propionic acid 18-2 was prepared. MS: 541.1 (M+H)$^+$; t$_R$=7.32 min (method 2).

Similarly, [5-chloro-4-(4-cyano-6-trifluoromethyl-pyridin-3-yl)-2-(methyl-pyridin-2-yl-sulfamoyl)-phenoxy]-acetic acid 18-3 was prepared. MS: 527.0 (M+H)$^+$; t$_R$=6.55 min (method 2).

Example 19

[5-Chloro-4-(4-cyano-6-trifluoromethyl-pyridin-3-yl)-2-(methyl-phenyl-sulfamoyl)-phenoxy-acetic acid

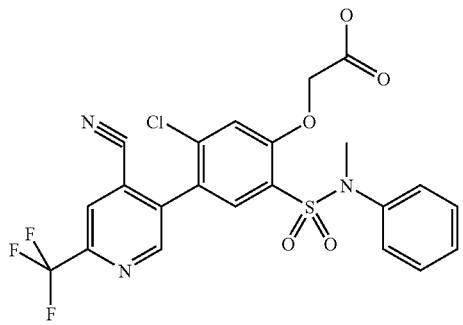

Step 19A: [5-Chloro-4-(4-cyano-6-trifluoromethyl-pyridin-3-yl)-2-(methyl-phenyl-sulfamoyl)-phenoxy]-acetic acid tert-butyl ester 4-Chloro-5-(4-cyano-6-trifluoromethyl-pyridin-3-yl)-2-methoxy-N-methyl-N-phenyl-benzenesulfonamide (88 mg, 0.18 mmol) was dissolved in DCM (5 mL) and cooled to −78° C. A solution of BBr$_3$ (125 mg, 0.5 mmol, 47 µL) in DCM (1 mL) was added at −78° C. and then warmed to −20° C. for 2 h. The reaction was quenched by addition of water (2 mL) and the mixture was warmed to r.t. followed by addition of EtOAc. The organic layer was separated, washed with NaHCO$_3$ (aq) and dried (MgSO$_4$). Purification by prep TLC eluting with 20% acetone/hexane gave 4-chloro-5-(4-cyano-6-trifluoromethyl-pyridin-3-yl)-2-hydroxy-N-methyl-N-phenyl-benzenesulfonamide contaminated with 30% of the starting material (69 mg). 35 mg of this material was dissolved in DMF (0.3 mL) and K$_2$CO$_3$ (14 mg, 0.1 mmol) was added followed by t-butyl-bromoacetate (20 mg, 0.1 mmol) and the mixture was stirred at r.t. for 3 days. The solvent was removed in vacuo and purification by prep TLC eluting with 20% acetone/hexane gave [5-chloro-4-(4-cyano-6-trifluoromethyl-pyridin-3-yl)-2-(methyl-phenyl-sulfamoyl)-phenoxy]-acetic acid tert-butyl ester (27 mg, 0.046 mmol). MS [M+H−tBu+H]$^+$: 526.0; t$_R$=3.18 min. (method 1)

Step 19B: [5-Chloro-4-(4-cyano-6-trifluoromethyl-pyridin-3-yl)-2-(methyl-phenyl-sulfamoyl)-phenoxy]-acetic acid

[5-Chloro-4-(4-cyano-6-trifluoromethyl-pyridin-3-yl)-2-(methyl-phenyl-sulfamoyl)-phenoxy]-acetic acid tert-butyl ester (27 mg, 0.046 mmol) was dissolved in DCM (0.2 mL) and TFA (0.2 mL) and was stirred at r.t. for 1 h. The solvent was removed and purification by prep TLC eluting with 70% acetone/hexane gave [5-chloro-4-(4-cyano-6-trifluoromethyl-pyridin-3-yl)-2-(methyl-phenyl-sulfamoyl)-phenoxy]-acetic acid 19-1 (4 mg, 0.008 mmol). MS [M+H]$^+$: 526.0; t$_R$=7.98 min. (method 2)

It will be appreciated that, although specific embodiments of the invention have been described herein for purposes of illustration, various modifications may be made without departing from the spirit and scope of the invention. Accordingly, the invention is not limited except as by the appended claims.

We claim:
1. A compound having the following structure (I):

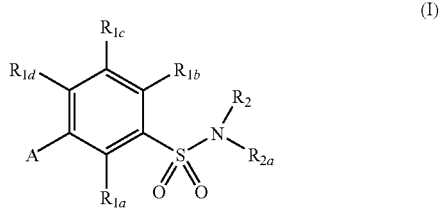

or a stereoisomer, or pharmaceutically acceptable salt thereof,
wherein:
A is pyridyl, phenyl, quinolinyl, naphthyridinyl, thienopyrimidinyl, or 2-oxo-pyrimidinyl, wherein the pyridyl, phenyl, quinolinyl, thienopyrimidinyl or 2-oxo-pyrimidinyl is substituted with 0-5 R$_4$;

R$_{1a}$ is H, halogen, C$_{1-4}$alkyl, C$_{1-4}$alkoxy or trifluoromethyl;

R$_{1b}$ and R$_{1c}$ are the same or different and are independently H, halogen, hydroxy, haloC$_{1-4}$alkyl, —C$_{1-6}$alkyl-(R$_5$)$_p$, —O—C$_{1-6}$alkyl-(R$_5$)$_p$, —C$_{1-6}$alkyl-O—C$_{1-6}$alkyl-(R$_5$)$_p$, —NR$_7$—C$_{1-6}$alkyl-(R$_5$)$_p$, or —S(O)$_m$—C$_{1-6}$alkyl-(R$_5$)$_p$;

R$_{1d}$ is F, Cl, methyl, CF$_3$ or cyano;

R$_2$ and R$_{2a}$ taken together with the nitrogen to which they are attached form a heterocycle which is substituted with 0-4 R$_3$, wherein the heterocycle is a 5- to 7-membered monocyclic ring or 7- to 14-membered polycyclic ring, containing from 1 to 4 heteroatoms independently selected from N, O, and S;

R$_3$ at each occurrence is independently halogen, cyano, halo-C$_{1-4}$alkyl, R$_5$, —C$_{1-6}$alkyl—(R$_5$)$_p$, —C$_{1-6}$alkyl-O—C$_{1-6}$alkyl-(R$_5$)$_p$, —O—C$_{1-6}$alkyl-(R$_5$)$_p$, —NR$_7$—C$_{1-6}$alkyl-(R$_5$)$_p$, —S(O)$_m$—C$_{1-6}$alkyl-(R$_5$)$_p$, —O—C$_{1-6}$alkyl-NR$_7$—C$_{1-6}$alkyl-(R$_5$)$_p$, heterocycle-(R$_5$)$_p$ wherein the heterocycle is a 5- to 7-membered monocyclic ring or 7- to 14-membered polycyclic ring, containing from 1 to 4 heteroatoms independently selected from N, O, and S;

R$_4$ at each occurrence is independently halogen, C$_{1-6}$alkyl, haloC$_{1-4}$alkyl, C$_{1-6}$alkoxy, hydroxy, cyano, thioC$_{1-6}$alkyl, —C(O)NR$_7$R$_8$, or 5 member heteroaryl wherein the heteroaryl has at least one heteroatom selected from N, O, and S;

R$_5$ at each occurrence is independently H, hydroxy, —OC(O)—C$_{1-6}$alkyl, —OC(O)O—C$_{1-6}$alkyl, —OC(O)—C$_{1-6}$alkyl-NR$_7$R$_8$, —COOR$_6$, —C(O)NR$_7$R$_8$, —NR$_7$C(O)NR$_7$R$_8$, —S(O)$_2$NR$_9$R$_9$, —S(O)$_m$—C$_{1-4}$alkyl, —NR$_7$R$_8$, C$_{1-6}$alkoxy, —O-heterocycle, or heterocycle wherein said heterocycle and said —O-heterocycle are substituted with 0-4 groups selected from halogen, $C_{1-6}$alkyl, $C_{1-4}$-haloalkyl, hydroxy, oxo, =S, —NH$_2$, —S(O)$_2$C$_{1-4}$alkyl and —COOH, and wherein the —O-heterocycle and the heterocycle are each independently a 5- to 7-membered monocyclic ring or 7- to 14-membered polycyclic ring, containing from 1 to 4 heteroatoms independently selected from N, O, and S;

$R_6$ at each occurrence is independently H, $C_{1-4}$alkyl, $C_{1-4}$alkyl-O—C(O)—$C_{1-6}$alkyl, or $C_{1-4}$alkyl-O—C(O)—O—$C_{1-6}$alkyl;

$R_7$ at each occurrence is independently H, $C_{1-4}$alkyl, hydroxy, or heterocycle where said heterocycle is substituted with 0-4 groups selected from halogen, $C_{1-6}$alkyl, hydroxy, oxo, —NH$_2$ and —COOH, and wherein the heterocycle is a 5- to 7-membered monocyclic ring or 7- to 14-membered polycyclic ring, containing from 1 to 4 heteroatoms independently selected from N, O, and S;

$R_8$ at each occurrence is independently H, $C_{1-4}$alkyl, haloC$_{1-4}$alkyl, —C(O)—$C_{1-4}$alkyl, —C(O)-haloC$_{1-4}$alkyl, —S(O)$_m$-haloC$_{1-4}$alkyl or —S(O)$_m$—$C_{1-4}$alkyl;

$R_9$ at each occurrence is independently H, $C_{1-4}$alkyl, or —C(O)C$_{1-4}$alkyl;

m is 0-2; and p at each occurrence is independently 1-3.

2. The compound of claim 1 having the following structure:

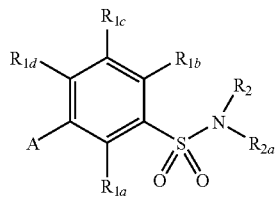

(I)

or a stereoisomer, or pharmaceutically acceptable salt thereof,
wherein:
A is pyridyl, phenyl, quinolinyl, thienopyrimidinyl, or 2-oxo-pyrimidinyl wherein the pyridyl, phenyl, quinolinyl, thienopyrimidinyl or 2-oxo-pyrimidinyl are substituted with 0-4 $R_4$;

$R_{1a}$ is H, halogen, $C_{1-4}$alkyl, $C_{1-4}$alkoxy or trifluoromethyl;

$R_{1b}$ and $R_{1c}$ are the same or different and are independently H, halogen, hydroxy, haloC$_{1-4}$alkyl, —$C_{1-6}$alkyl-(R$_5$)$_p$, —O—$C_{1-6}$alkyl-(R$_5$)$_p$, —NR$_7$—$C_{1-6}$alkyl-(R$_5$)$_p$, or —S(O)$_m$—$C_{1-4}$alkyl-(R$_5$)$_p$;

$R_{1d}$ is Cl, methyl, CF$_3$ or cyano;

$R_2$ is $C_{1-4}$alkyl-(R$_5$)$_p$;

$R_2$ and $R_{2a}$ taken together with the nitrogen to which they are attached form a heterocycle which is substituted with 0-4 $R_3$, wherein the heterocycle is a 5- to 7-membered monocyclic ring or 7- to 14-membered polycyclic ring, containing from 1 to 4 heteroatoms independently selected from N, O, and S;

$R_3$ at each occurrence is independently halogen, haloC$_{1-4}$ alkyl, hydroxy, —$C_{1-6}$alkyl-(R$_5$)$_p$, —$C_{1-6}$alkyl-O—$C_{1-6}$alkyl-(R$_5$)$_p$, —O—$C_{1-6}$alkyl-(R$_5$)$_p$, —NR$_5$—$C_{1-6}$alkyl-(R$_5$)$_p$, —S(O)$_m$—$C_{1-6}$alkyl-(R$_5$)$_p$, —CO$_2$R$_6$, or —C(O)NR$_7$R$_8$;

$R_4$ at each occurrence is independently halogen, $C_{1-6}$alkyl, haloC$_{1-4}$alkyl, $C_{1-4}$alkoxy, hydroxy, cyano, thioC$_{1-4}$alkyl, —C(O)NR$_7$R$_8$, or 5 member heteroaryl wherein the heteroaryl has at least one heteroatom selected from N, O, and S;

$R_5$ at each occurrence is independently H, hydroxy, —OC(O)—$C_{1-6}$alkyl, —OC(O)O—$C_{1-6}$alkyl, —OC(O)—$C_{1-6}$alkyl-NR$_7$R$_8$, —C(O)OR$_6$, —C(O)NR$_7$R$_8$, —S(O)$_2$NR$_9$R$_9$, —S(O)$_m$C$_{1-4}$alkyl, —NR$_7$R$_8$, $C_{1-6}$alkoxy, or a heterocycle selected from the group consisting of

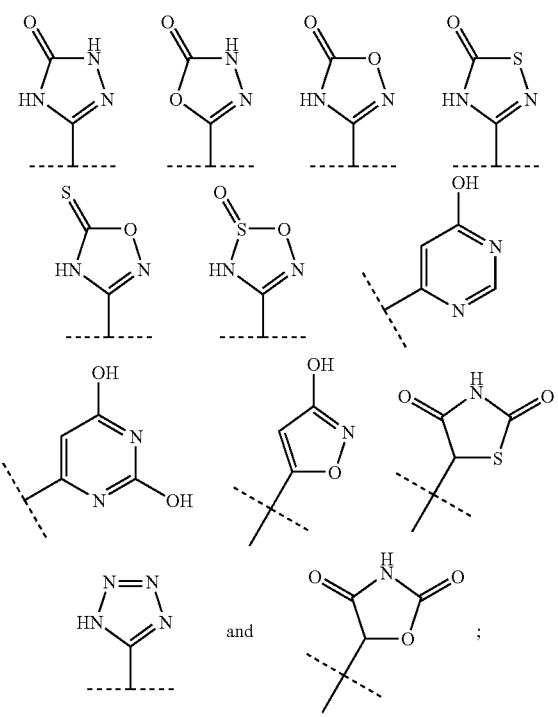

$R_6$ at each occurrence is independently H, $C_{1-4}$alkyl, $C_{1-4}$alkyl-O—C(O)—$C_{1-6}$alkyl, or $C_{1-4}$alkyl-O—C(O)—O—$C_{1-6}$alkyl;

$R_7$ is H, $C_{1-4}$alkyl or hydroxy;

$R_8$ is H, $C_{1-4}$alkyl, —C(O)—$C_{1-4}$alkyl, or —S(O)$_m$—$C_{1-4}$alkyl;

$R_9$ at each occurrence is independently H, $C_{1-4}$alkyl, or —C(O)C$_{1-4}$-alkyl;

m is 0-2; and p at each occurrence is independently 1-3.

3. The compound of claim 1 wherein A is pyridyl substituted with 0-4 $R_4$.

4. The compound of claim 3 wherein A is 2-pyridyl substituted with 0-4 $R_4$.

5. The compound of claim 3 wherein A is 3-pyridyl substituted with 0-4 $R_4$.

6. The compound of claim 1 wherein A is phenyl substituted with 0-4 $R_4$.

7. The compound of claim 1 wherein A is quinolinyl substituted with 0-4 $R_4$.

8. The compound of claim 1 wherein A is thienopyrimidinyl substituted with 0-4 $R_4$.

9. The compound of claim 1 wherein A is 2-oxo-pyrimidinyl substituted with 0-4 $R_4$.

10. The compound of claim 1 wherein $R_{1a}$ and $R_{1c}$ are H.

11. The compound of claim 1 wherein $R_{1b}$ is —$C_{1-6}$alkyl-$(R_5)_p$ or —O—$C_{1-6}$alkyl-$(R_5)_p$.

12. The compound of claim 1, wherein $R_2$ and $R_{2a}$ are taken together with the nitrogen to which they are attached to form a 9-12 membered heterocycle which is substituted with 0-4 $R_3$.

13. The compound of claim 1 wherein $R_3$ is —O—$C_{1-6}$ alkyl-$(R_5)_p$.

14. The compound of claim 1 wherein the compound is 4-[5-Chloro-4-(4-cyano-6-trifluoromethyl-pyridin-3-yl)-2-(2,3,4,5-tetrahydro-benzo[b]azepine-1-sulfonyl)-phenoxy]-butyric acid, [5-Chloro-4-(4-cyano-6-trifluoromethyl-pyridin-3-yl-2-(2,3,4,5-tetrahydro-benzo[b]azepine-1-sulfonyl)-phenoxy]-acetic acid, 5-[2-Chloro-5-(4,4-dimethyl-3,4-dihydro-2H-quinoline-1-sulfonyl)-4-(4-hydroxy-butoxy)-phenyl]-2-trifluoromethyl-isonicotinonitrile, 5-[2-Chloro-5-(4,4-dimethyl-3,4-dihydro-2H-quinoline-1-sulfonyl)-4-(2-hydroxy-ethoxy)-phenyl]-2-trifluoromethyl-isonicotinonitrile, 4-[5-Chloro-4-(4-cyano-6-trifluoromethyl-pyridin-3-yl)-2-(4,4-dimethyl-3,4-dihydro-2H-quinoline-1-sulfonyl)-phenoxy]-butyric acid, [5-Chloro-4-(4-cyano-6-trifluoromethyl-pyridin-3-yl)-2-(4,4-dimethyl-3,4-dihydro-2H-quinoline-1-sulfonyl)-phenoxy]-acetic acid, 3-[5-Chloro-4-(4-cyano-6-trifluoromethyl-pyridin-3-yl)-2-(4,4-dimethyl-3,4-dihydro-2H-quinoline-1-sulfonyl)-phenoxy]-propionic acid, 5-[2-Chloro-5-(4,4-dimethyl-3,4-dihydro-2H-quinoline-1-sulfonyl)-4-methoxy-phenyl]-2-trifluoromethyl-isonicotinonitrile, 5-[2-Chloro-4-methoxy-5-(2,3,4,5-tetrahydro-benzo[b]azepine-1-sulfonyl)-phenyl]-2-trifluoromethyl-isonicotinonitrile, or a pharmaceutically acceptable salt thereof.

15. A pharmaceutical composition comprising the compound of claim 1, or a pharmaceutically acceptable salt thereof, and a pharmaceutically acceptable carrier or diluent.

16. A method for treating a condition in a subject in need thereof, wherein said condition is endometriosis, uterine fibroids, polycystic ovarian disease, dysmenorrhea, dyspareunia, menorrhagia, premature ovarian failure due to chemotherapy or early menopause, hirsutism, precocious puberty, gonadal steroid-dependent neoplasia, cancers of the prostate, breast or ovary, gonadotroph pituitary adenomas, adenomyosis, premenstrual syndrome, benign prostatic hypertrophy, or infertility, said method comprising administering to the subject an effective amount of the pharmaceutical composition of claim 15.

17. The method of claim 16 wherein the condition is endometriosis, dysmenorrhea, polycystic ovarian disease or uterine fibroids.

18. The method of claim 16 wherein the condition is benign prostatic hypertrophy, myoma of the uterus, prostatic cancer, uterine cancer, breast cancer or pituitary gonadotroph adenomas.

* * * * *